(12) United States Patent
Dozeman et al.

(10) Patent No.: US 11,944,396 B2
(45) Date of Patent: Apr. 2, 2024

(54) SYSTEMS AND METHODS FOR CONTROLLING ROBOTIC MOVEMENT OF A TOOL BASED ON A VIRTUAL BOUNDARY

(71) Applicant: MAKO Surgical Corp., Weston, FL (US)

(72) Inventors: Michael Dale Dozeman, Portage, MI (US); Patrick Roessler, Merzhausen (DE); Gregory Garcia, Parkland, FL (US); Rishabh Khurana, Fort Lauderdale, FL (US); Jeremy L. Dunn, Portage, MI (US); David Gene Bowling, Los Ranchos De Albuquerque, NM (US)

(73) Assignee: MAKO Surgical Corp., Weston, FL (US)

( * ) Notice: Subject to any disclaimer, the term of this patent is extended or adjusted under 35 U.S.C. 154(b) by 290 days.

(21) Appl. No.: 17/212,568

(22) Filed: Mar. 25, 2021

(65) Prior Publication Data
US 2021/0298846 A1 Sep. 30, 2021

Related U.S. Application Data

(60) Provisional application No. 63/000,860, filed on Mar. 27, 2020.

(51) Int. Cl.
*A61B 34/00* (2016.01)
*A61B 34/20* (2016.01)
*A61B 34/32* (2016.01)

(52) U.S. Cl.
CPC .............. *A61B 34/25* (2016.02); *A61B 34/20* (2016.02); *A61B 34/32* (2016.02); *A61B 34/76* (2016.02)

(58) Field of Classification Search
CPC .......... A61B 34/10; A61B 34/20; A61B 34/30
See application file for complete search history.

(56) References Cited

U.S. PATENT DOCUMENTS

| 7,206,626 B2 | 4/2007 | Quaid, III |
| 7,747,311 B2 | 6/2010 | Quaid, III |

(Continued)

FOREIGN PATENT DOCUMENTS

| WO | 2000060571 A1 | 10/2000 |
| WO | 2016187290 A1 | 11/2016 |

(Continued)

OTHER PUBLICATIONS

Tamis, Marijn et al., "Constraint Based Physics Solver", http://www.mft-spirit.nl/files/MTamis_ConstraintBasedPhysicsSolver.pdf, Version 1.02, Jun. 15, 2015, 31 pages.

(Continued)

*Primary Examiner* — Boniface N Nganga
(74) *Attorney, Agent, or Firm* — Howard & Howard Attorneys PLLC

(57) ABSTRACT

Systems and methods are provided for controlling robotic movement of a tool based on one or more virtual boundaries. The system comprises a tool and a manipulator to support the tool. A control system controls operation of the manipulator and movement of the tool based on a relationship between the tool and the one or more virtual boundaries associated with a target site. The control system includes a boundary handler to determine whether the tool is in compliance with the one or more virtual boundaries or is in violation of the one or more virtual boundaries.

32 Claims, 28 Drawing Sheets

(56) References Cited

U.S. PATENT DOCUMENTS

| | | |
|---|---|---|
| 7,916,121 B2 | 3/2011 | Braun et al. |
| 8,010,180 B2 | 8/2011 | Quaid et al. |
| 8,287,522 B2 | 10/2012 | Moses et al. |
| 8,391,954 B2 | 3/2013 | Quaid, III |
| 9,008,757 B2 | 4/2015 | Wu |
| 9,119,655 B2 | 9/2015 | Bowling et al. |
| 9,308,050 B2 | 4/2016 | Kostrzewski et al. |
| 9,566,122 B2 | 2/2017 | Bowling et al. |
| 9,639,156 B2 | 5/2017 | Iorgulescu et al. |
| 9,707,043 B2 | 7/2017 | Bozung |
| 10,117,713 B2 | 11/2018 | Moctezuma de la Barrera et al. |
| 2004/0024311 A1 | 2/2004 | Quaid |
| 2006/0142657 A1 | 6/2006 | Quaid et al. |
| 2008/0010706 A1 | 1/2008 | Moses et al. |
| 2012/0176306 A1 | 7/2012 | Lightcap et al. |
| 2012/0330429 A1 | 12/2012 | Axelson, Jr. et al. |
| 2013/0006267 A1 | 1/2013 | Odermatt et al. |
| 2013/0169423 A1 | 7/2013 | Iorgulescu et al. |
| 2014/0039681 A1 | 2/2014 | Bowling et al. |
| 2014/0180290 A1 | 6/2014 | Otto et al. |
| 2014/0276943 A1 | 9/2014 | Bowling et al. |
| 2014/0276949 A1 | 9/2014 | Staunton et al. |
| 2014/0316434 A1 | 10/2014 | Simaan et al. |
| 2015/0265358 A1 | 9/2015 | Bowling et al. |
| 2015/0342691 A1 | 12/2015 | Otto et al. |
| 2016/0175054 A1 | 6/2016 | Kang et al. |
| 2016/0242858 A1 | 8/2016 | Moctezuma de la Barrera et al. |
| 2016/0338762 A1* | 11/2016 | Krastins ............. A61B 18/1485 |
| 2016/0338782 A1 | 11/2016 | Bowling et al. |
| 2017/0177191 A1* | 6/2017 | Lightcap ................ A61B 34/20 |
| 2018/0353253 A1 | 12/2018 | Bowling |
| 2019/0133790 A1* | 5/2019 | Viscardi ................ A61F 2/4612 |
| 2019/0223962 A1* | 7/2019 | Roldan .................. A61B 34/30 |
| 2019/0357918 A1 | 11/2019 | Otto et al. |
| 2020/0085513 A1 | 3/2020 | Bowling et al. |
| 2020/0170724 A1 | 6/2020 | Flatt et al. |
| 2020/0281676 A1 | 9/2020 | Rohs et al. |
| 2020/0289133 A1 | 9/2020 | Elbanna et al. |

FOREIGN PATENT DOCUMENTS

| | | |
|---|---|---|
| WO | 2017204832 A1 | 11/2017 |
| WO | 2021067438 A1 | 4/2021 |

OTHER PUBLICATIONS

Tamis, Marijn, "Comparison Between Projected Gauss-Seidel and Sequential Impulse Solvers for Real-Time Physics Simulations," http://www.mft-spirit.nl/files/MTamis_PGS_SI_Comparison.pdf, Version 1.01, Jul. 1, 2015, 11 pages.

U.S. Appl. No. 62/908,056, filed Sep. 30, 2019.

International Search Report for Application No. PCT/US2021/024135 dated Aug. 25, 2021, 6 pages.

* cited by examiner

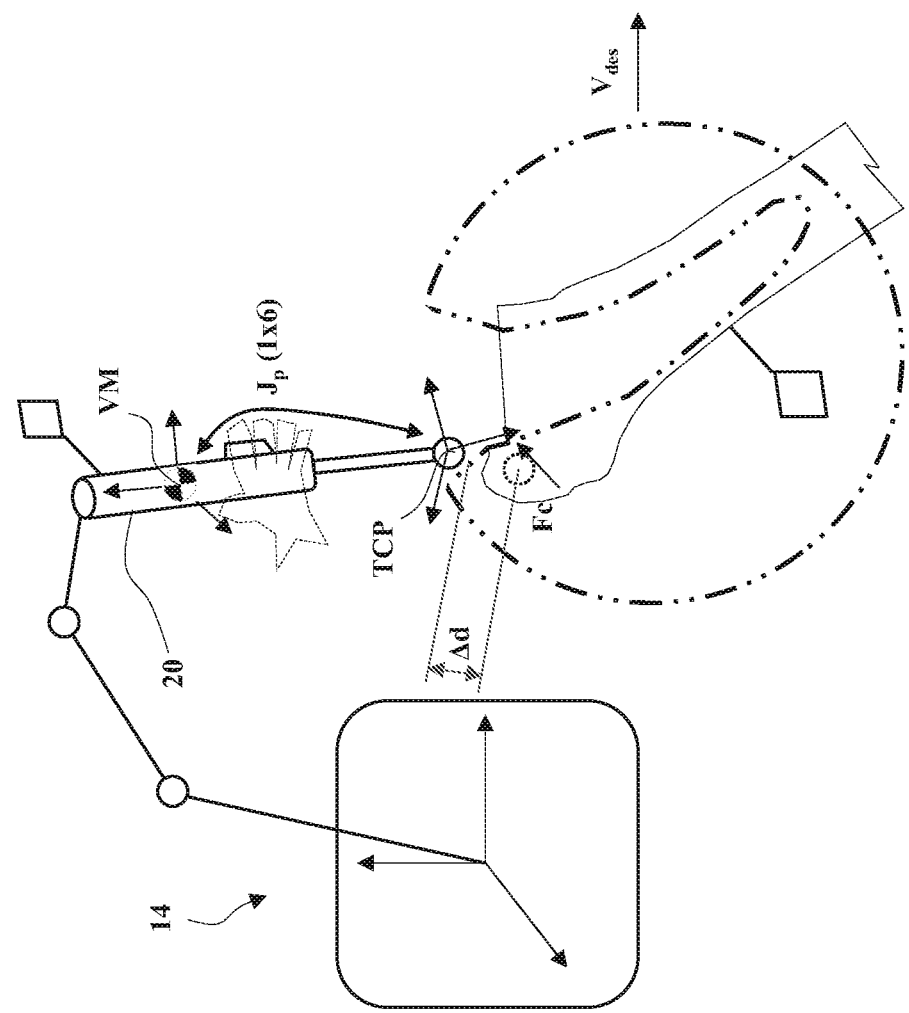
FIG. 10

Constraint Equation

- Calculate force for each constraint ($F_{p_i}$) in constraint space by solving system of n linear equations ($Ax = b \rightarrow x = A^{-1}b = F = (M^{-1})^{-1}a$)

$$F_p = \left(J_p M^{-1} J_p^T + \frac{C}{\Delta t}\right)^{-1} \left(\frac{v_{p_2}}{\Delta t} - \frac{J_p v_{cg_1}}{\Delta t} - \frac{\epsilon \Delta d}{\Delta t^2} - \left(J_p M^{-1} + \frac{C}{\Delta t} J_p^{-T}\right)\left(F_{inertial} + F_{damping} + F_{cg_{ext}}\right)\right) \geq 0$$

FIG. 12

Forward Dynamics Algorithm

Configuration Parameters :

Mass matrix, $M_{6DOF}$ [6 × 6] combination of Mass and Inertia [3 × 3] matrices Velocity Limits, $v_{max}$, $\omega_{max}$ Inputs :

initial pose, $^{0}_{n}T(t_{0})$ initial velocity, $^{n}v(t_{0})$ total force applied at CG, $^{n}F_{total}$ time interval, dT Outputs :

final pose, $^{0}_{n}T(t_{0} + dT)$ final velocity, $^{n}v(t_{0} + dT)$

FIG. 13

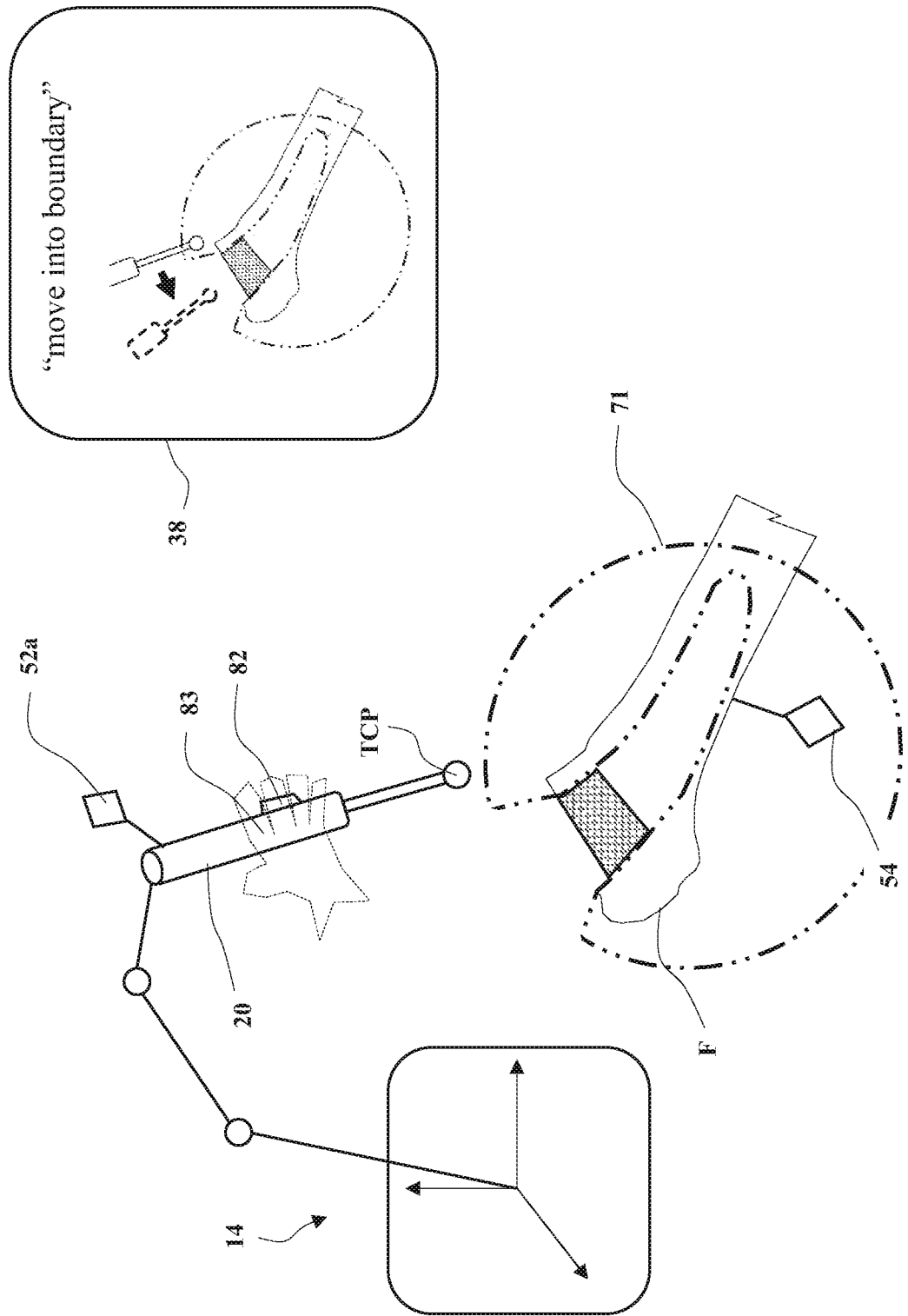

SYSTEMS AND METHODS FOR CONTROLLING ROBOTIC MOVEMENT OF A TOOL BASED ON A VIRTUAL BOUNDARY

CROSS-REFERENCE TO RELATED APPLICATIONS

The subject application claims priority to and all benefits of U.S. Provisional Patent Application No. 63/000,860, filed Mar. 27, 2020, the disclosure of which is hereby incorporated by reference in its entirety.

TECHNICAL FIELD

The present disclosure relates generally to systems and methods for controlling robotic movement of a tool based on a virtual boundary.

BACKGROUND

Surgical systems may include a robotic manipulator and a tool coupled to the manipulator to perform a surgical procedure on a patient. During operation, the surgical system may limit movement of the tool to avoid violating a virtual boundary established to protect portions of the patient's anatomy from the tool.

In some situations, the user may desire to adjust a position of the patient to improve access to a target site on the patient's anatomy or to improve the user's visualization of the patient's anatomy, or the patient's anatomy may move for some other reason. In order to maintain compliance with the virtual boundary when the patient's anatomy moves, the surgical system may command the manipulator to move the tool autonomously to compensate for such movement of the patient's anatomy. However, some users may prefer that such autonomous movement of the tool be limited. For instance, users may not want the tool to move unexpectedly, or users may want movement of the tool to only occur in response to input from a user.

SUMMARY

This Summary introduces a selection of concepts in a simplified form that are further described below in the Detailed Description below. This Summary is not intended to limit the scope of the claimed subject matter nor identify key features or essential features of the claimed subject matter.

According to a first aspect, a surgical system is provided that comprises a tool, a manipulator to support the tool, and a control system to control operation of the manipulator and movement of the tool based on a relationship between the tool and a virtual boundary associated with a target site. The control system includes a user input having a first input state and a second input state. The control system is configured to enable autonomous, boundary-complying movement of the tool when the user input is in the first input state so that the tool maintains compliance with the virtual boundary. The control system is configured to disable autonomous, boundary-complying movement of the tool when the user input is in the second input state. The control system includes a boundary handler to determine, in response to the user input transitioning from the second input state to the first input state, whether the tool is in violation of the virtual boundary.

According to a second aspect, a surgical system is provided that comprises a tool, a manipulator to support the tool, and a control system to control operation of the manipulator and movement of the tool based on a relationship between the tool and a first virtual boundary associated with a target site. The control system includes a virtual boundary selector to enable a user to select a second virtual boundary associated with the target site. The control system is configured to enable the user to select the second virtual boundary with the virtual boundary selector while the control system maintains compliance of the tool with the first virtual boundary. The control system includes a boundary handler to determine, in response to the user selecting the second virtual boundary, whether the tool is in compliance with the second virtual boundary.

According to a third aspect, a surgical system is provided that comprises a tool, a manipulator to support the tool, and a control system to control operation of the manipulator and movement of the tool based on a relationship between the tool and a virtual boundary associated with a target site. The manipulator is operable in a plurality of modes, including a manual mode in which the manipulator moves the tool in response to user forces and torques applied to the tool by a user and in a semi-autonomous mode in which the manipulator moves the tool along a tool path. The control system includes a path handler to generate a lead-in path from a current position of the tool to the tool path in response to the control system transitioning to the semi-autonomous mode. The control system also includes a boundary handler to determine, prior to movement of the tool along the lead-in path, whether movement of the tool along the lead-in path would maintain compliance with the virtual boundary by modeling motion of a plurality of stereotactic interaction features associated with the tool to determine if the stereotactic interaction features comply with the virtual boundary.

According to a fourth aspect, a method is provided for controlling operation of a manipulator supporting a tool based on a relationship between the tool and a virtual boundary associated with a target site. The method comprises initiating autonomous, boundary-complying movement of the tool when a user input is in a first input state and in response to the virtual boundary moving relative to the tool, such that the tool maintains compliance with the virtual boundary. The method also comprises disabling autonomous, boundary-complying movement of the tool when the user input is in a second input state and determining, in response to the user input transitioning from the second input state to the first input state, whether the tool is in violation of the virtual boundary.

According to a fifth aspect, a method is provided for controlling operation of a manipulator supporting a tool based on a relationship between the tool and a first virtual boundary associated with a target site. The method comprises enabling a user to select a second virtual boundary associated with the target site. The method also comprises enabling the user to select the second virtual boundary while maintaining compliance of the tool with the first virtual boundary and determining, in response to the user selecting the second virtual boundary, whether the tool is in compliance with the second virtual boundary.

According to a sixth aspect, a method is provided for controlling operation of a manipulator supporting a tool based on a relationship between the tool and a virtual boundary associated with a target site, wherein the manipulator is operable in a plurality of modes, including a manual mode in which the manipulator moves the tool in response to user forces and torques applied to the tool by a user and a semi-autonomous mode in which the manipulator moves the tool along a tool path. The method comprises transitioning the manipulator to the semi-autonomous mode and generating a lead-in path from a current position of the tool to the tool path in response to transitioning the manipulator to the semi-autonomous mode. The method also comprises determining, prior to movement of the tool along the lead-in path, whether movement of the tool along the lead-in path would maintain compliance with the virtual boundary by modeling motion of a plurality of stereotactic interaction features associated with the tool to determine if the stereotactic interaction features comply with the virtual boundary.

According to a seventh aspect, a surgical system is provided, comprising: a localization system configured to track a first object and a second object; and at least one controller configured to: associate a virtual boundary with one or more first objects; associate a first stereotactic interaction feature and a second stereotactic interaction feature with one or more second objects; define a first parameter for the first stereotactic interaction feature; define a second parameter for the second stereotactic interaction feature, wherein the first parameter is different from the second parameter; and generate a response based on interaction between at least one of the first and second stereotactic interaction features and the virtual boundary.

According to an eighth aspect, a method of operating a surgical system is provided, the surgical system including a localization system and at least one controller, the method comprising: tracking a first object and a second object with the localization system; and associating, with the at least one controller, a virtual boundary with one or more first objects; associating, with the at least one controller, a first stereotactic interaction feature and a second stereotactic interaction feature with one or more second objects; defining, with the at least one controller, a first parameter for the first stereotactic interaction feature; defining, with the at least one controller, a second parameter for the second stereotactic interaction feature, wherein the first parameter is different from the second parameter; and generating, with the at least one controller, a response based on interaction between at least one of the first and second stereotactic interaction features and the virtual boundary.

Any of the above aspects may be combined, in whole or in part.

Any of the above aspects may be utilized with any of the following implementations, whether such implementations are utilized in whole, or in part:

In some implementations, the manipulator is a surgical robotic manipulator comprising a base and a plurality of links and joints forming a robotic arm. In some implementations, the manipulator is a hand-held manipulator, freely supported in the hand of a user against the force of gravity, where the base is a base portion of a tool (e.g., a portion held free-hand by the user) and the tool tip is movable relative to the base portion. In some implementations, the tool is a rotary cutting bur, a saw, a cutting guide, an ultrasonic vibrating tool, a laser cutting tool, or the like.

In some implementations, the control system is configured to initiate a recovery mode in response to the tool being in violation of the virtual boundary. In some implementations, the violation occurs when the user input transitions from the second input state to the first input state. In some implementations, autonomous, boundary-complying movement of the tool remains disabled in the recovery mode when the user input is in the first input state.

In some implementations, the tool includes a tool drive and the control system is configured to disable operation of the tool drive in response to the tool being in violation of the virtual boundary. In some implementations, the violation occurs when the user input transitions from the second input state to the first input state.

In some implementations, the control system is configured to guide a user into placing the tool into compliance with the virtual boundary in the recovery mode. In some implementations, the guiding occurs by generating user feedback. In some implementations, the feedback includes one or more of audible feedback, visual feedback, and haptic feedback. In some implementations, the control system is configured to cease generating the user feedback when the tool is placed into compliance with the virtual boundary. In some implementations, the control system is configured to limit relative movement between the tool and the virtual boundary. In some implementations, limiting relative movement occurs when the user input is in the first input state and by generating boundary constraints with the boundary handler.

In some implementations, the control system comprises: a constraint solver to calculate a constraint force adapted to maintain the tool in compliance with the virtual boundary based on the boundary constraints. In some implementations, the control system comprises: a virtual simulator to simulate dynamics of the tool in a virtual simulation based on the constraint force, and to output a commanded pose. In some implementations, the control system is configured to command the manipulator to move the tool based on the commanded pose.

In some implementations, the boundary handler is operable between a boundary-enabled state and a boundary-disabled state. The boundary-enabled state is a state in which boundary constraints are being transmitted from the boundary handler to the constraint solver to thereby enable autonomous, boundary-complying movement of the tool. In some implementations, enabling autonomous, boundary-complying movement occurs when the virtual boundary moves relative to the tool in a manner that would otherwise cause the tool to violate the virtual boundary. In some implementations, the boundary-disabled state in which boundary constraints are no longer being transmitted from the boundary handler to the constraint solver to thereby disable autonomous, boundary-complying movement of the tool such that the virtual boundary is movable relative to the tool in a manner that causes the tool to violate the virtual boundary. In some implementations, the boundary handler is configured to: operate in the boundary-disabled state in response to the user input transitioning from the first input state to the second input state. In some implementations, the boundary handler is configured to: operate in the boundary-enabled state in response to the user input transitioning from the second input state to the first input state with the tool in compliance with the virtual boundary. In some implementations, the boundary handler is configured to: operate in the boundary-disabled state in response to the user input transitioning from the second input state to the first input state with the tool in violation of the virtual boundary.

In some implementations, the control system is configured to provide haptic feedback to the user to guide the user into placing the tool into compliance with the virtual boundary. In some implementations, feedback occurs by activating one or more guide constraints to guide the tool into compliance with the virtual boundary. In some implementations, the control system is configured to provide haptic feedback to the user to guide the user into placing the tool into compliance with the virtual boundary. In some implementations, the haptic feedback occurs by dampening movement of the tool. In some implementations, the control system is configured to switch the boundary handler from the boundary-disabled state to the boundary-enabled state when the tool is placed into compliance with the virtual boundary.

In some implementations, the user input is configured such that the first input state indicates that a user is actively engaging the tool and the second input state indicates that the user has released the tool.

In some implementations, the user input is located on the tool and the user input is configured such that the user input is actuated to place the user input in the first input state and the user input is released to place the user input in the second input state. In some implementations, the tool has a grip and the user input includes a presence detector to detect a hand of a user on the grip.

In some implementations, the control system comprises a pendant and the user input is located on the pendant. In some implementations, the user input is configured such that the user input is actuated to place the user input in the first input state and the user input is released to place the user input in the second input state.

In some implementations, the user input is further defined as a tool input located on the tool. In some implementations, the first and second input states are further defined as a tool input first state and a tool input second state. In some implementations, the control system comprises a pendant and a pendant input located on the pendant, the pendant input having a pendant input first state and a pendant input second state.

In some implementations, the manipulator is operable in a manual mode in which the manipulator moves the tool in response to user forces and torques applied to the tool by a user when the tool input is in the tool input first state. In some implementations, the manipulator is operable in a semi-autonomous mode in which the manipulator moves the tool along a tool path when the pendant input is in the pendant input first state. In some implementations, the boundary handler is configured to determine whether the tool is in compliance with the virtual boundary or is in violation of the virtual boundary in response to the control system switching operation of the manipulator from one of the manual and semi-autonomous modes to the other of the manual and semi-autonomous modes. In some implementations, the control system comprises a path handler configured to generate a lead-in path from a current position of the tool to the tool path. In some implementations, the lead-in path is generated when the manipulator switches from the manual mode to the semi-autonomous mode. In some implementations, the boundary handler is configured to determine whether movement of the tool along the lead-in path would maintain compliance with the virtual boundary or would violate the virtual boundary. In some implementations, the boundary handler is configured to determine whether movement of the tool along the lead-in path would maintain compliance with the virtual boundary or would violate the virtual boundary by modeling motion of a plurality of stereotactic interaction features associated with the tool to determine if the stereotactic interaction features would maintain compliance with the virtual boundary or would violate the virtual boundary. In some implementations, the boundary handler is configured to model motion of the plurality of stereotactic interaction features in three or more degrees of freedom. In some implementations, the control system comprises a guide handler configured to generate user feedback to the user in response to the boundary handler determining that the tool would violate the virtual boundary if the tool moved from the current position, along the lead-in path, to the tool path.

In some implementations, the control system is configured to disable autonomous, boundary-complying movement of the tool in response to one or more of the following: the tool coming to a stop; a predetermined time period elapsing following a transition of the user input from the first input state to the second input state; a linear velocity of the tool falling below one or more thresholds; or an angular velocity of the tool falling below one or more thresholds.

In some implementations, the control system is configured to determine whether the tool remains in compliance with the virtual boundary based on a tolerance defined for the virtual boundary.

In some implementations, the control system is configured to generate a recovery tool path in the recovery mode to move the tool into compliance with the virtual boundary.

In some implementations, the control system is configured to move the virtual boundary in the recovery mode from a starting location so that the tool returns to being in compliance with the virtual boundary and thereafter, moving the virtual boundary back to the starting location while enabling autonomous, boundary-complying movement of the tool.

In some implementations, the boundary handler, in response to the user selecting the second virtual boundary, is configured to: activate the second virtual boundary and deactivate the first virtual boundary if the boundary handler determines that the tool is in compliance with the second virtual boundary so that the control system transitions to controlling operation of the manipulator and movement of the tool based on a relationship between the tool and the second virtual boundary. In some implementations, the boundary handler, in response to the user selecting the second virtual boundary, is configured to: maintain the first virtual boundary as being active if the boundary handler determines that the tool is in violation of the second virtual boundary so that the control system continues to control operation of the manipulator and movement of the tool based on the relationship between the tool and the first virtual boundary. In some implementations, the control system is configured to generate user feedback to the user in response to the boundary handler determining that the tool is in violation of the second virtual boundary.

In some implementations, the control system comprises a user input having a first input state and a second input state, the user input located on the tool and configured such that the user input is actuated by the user to place the user input in the first input state and the user input is released by the user to place the user input in the second input state. In some implementations, the control system is configured to enable the user to select the second virtual boundary with the virtual boundary selector while the user input is in the first input state. In some implementations, the virtual boundary selector comprises a second user input located on the tool. In some implementations, the tool includes a tool drive and the control system is configured to continue operation of the tool drive when the user selects the second virtual boundary with the virtual boundary selector. In some implementations, the control system is configured to limit relative movement between the tool and the first virtual boundary when the user input is in the first input state and the first virtual boundary is active. In some implementations, the control system limits so by generating first boundary constraints with the boundary handler and the control system is configured to limit relative movement between the tool and the second virtual boundary when the user input is in the first input state and the second virtual boundary is active by generating second boundary constraints with the boundary handler. In some implementations, the control system comprises: a constraint solver to calculate a constraint force adapted to maintain the tool in compliance with the first virtual boundary based on the first boundary constraints or in compliance with the second virtual boundary based on the second boundary constraints. In some implementations, the control system comprises a virtual simulator to simulate dynamics of the tool in a virtual simulation based on the constraint force, and to output a commanded pose. In some implementations, the control system is configured to command the manipulator to move the tool based on the commanded pose. In some implementations, the virtual boundary selector is configured to enable a user to toggle between the first and second virtual boundaries, toggle sequentially from among a plurality of virtual boundaries, or select from a list of virtual boundaries.

In some implementations, the first and second parameters are each further defined as stiffness parameters, and wherein the first stereotactic interaction feature is stiffer than the second stereotactic interaction feature. In some implementations, the at least one controller is configured to: identify an event; and change at least one of the first parameter or the second parameter in response to identification of the event. In some implementations, the first and second parameters are each further defined as geometrical parameters defined as at least one of: size, area, volume, or shape of the stereotactic interaction feature; and wherein the first geometrical parameter is different from the second geometrical parameter. In some implementations, one or more of the first and second stereotactic interaction features are associated with the one or more second objects by being positioned at a location that is spaced apart from the one or more second objects by a distance. In some implementations, the at least one controller is configured to define one or more of the first and second parameters by being configured to: receive user input defining one or more of the first and second parameters; or automatically define one or more of the first and second parameters based on surgical information. In some implementations, to generate the response based on interaction between at least one of the first and second stereotactic interaction features and the virtual boundary the at least one controller is configured to: identify a collision or anticipated collision between one or more of the first and second stereotactic interaction features and the virtual boundary; and generate the response which is further defined as the at least one controller being configured to perform one or more of the following: adjust a pose of the one or more second objects; and generate an alert or notification regarding the collision or anticipated collision. In some implementations, the one or more second objects are further defined as a single second object, wherein the first stereotactic interaction feature and the second stereotactic interaction feature are associated with the single second object. In some implementations, the one or more second objects are further defined as a separate second objects, wherein the first stereotactic interaction feature is associated with one of the second objects and the second stereotactic interaction feature is associated with another one of the second objects. In some implementations, the one or more first objects is further defined as a bone; the virtual boundary is further defined as cutting boundary delineating anatomy to be removed from anatomy which should not be removed; the one or more second objects is further defined as a rotary cutting tool; the first and second stereotactic interaction features are associated with the rotary cutting tool and are located at different positions relative to the rotary cutting tool; and the first and second parameters are each further defined as stiffness parameters, and wherein the first stereotactic interaction feature is stiffer than the second stereotactic interaction feature. In some implementations, the one or more first objects comprise one or more of the following: an anatomy of a patient; any part of a kinematic chain that forms a robotic manipulator, including a base, link, joint, end effector, tool, sterile adapter, energy applicator; a hand-held tool or device; a surgical table; a head-mounted device; a hand-held display device or tablet; a surgical tracker; a retractor; an imaging device; a human in an operation room; and the one or more second objects comprise one or more of the following: an anatomy of a patient; any part of a kinematic chain that forms a robotic manipulator, including a base, link, joint, end effector, tool, sterile adapter, energy applicator; a hand-held tool or device; a surgical table; a head-mounted device; a hand-held display device or tablet; a surgical tracker; a retractor; an imaging device; a human in an operation room.

DESCRIPTION OF THE DRAWINGS

Advantages of the present disclosure will be readily appreciated as the same becomes better understood by reference to the following detailed description when considered in connection with the accompanying drawings.

FIG. 10 is an illustration of virtual constraints.

FIG. 12 shows a sample constraint equation.

FIGS. 13 and 14 show a sample forward dynamics algorithm for carrying out a virtual simulation.

FIGS. 18A-18G illustrate movements of a tool and virtual boundary during a surgical procedure on a femur.

DETAILED DESCRIPTION

I. Overview

Figure 1:
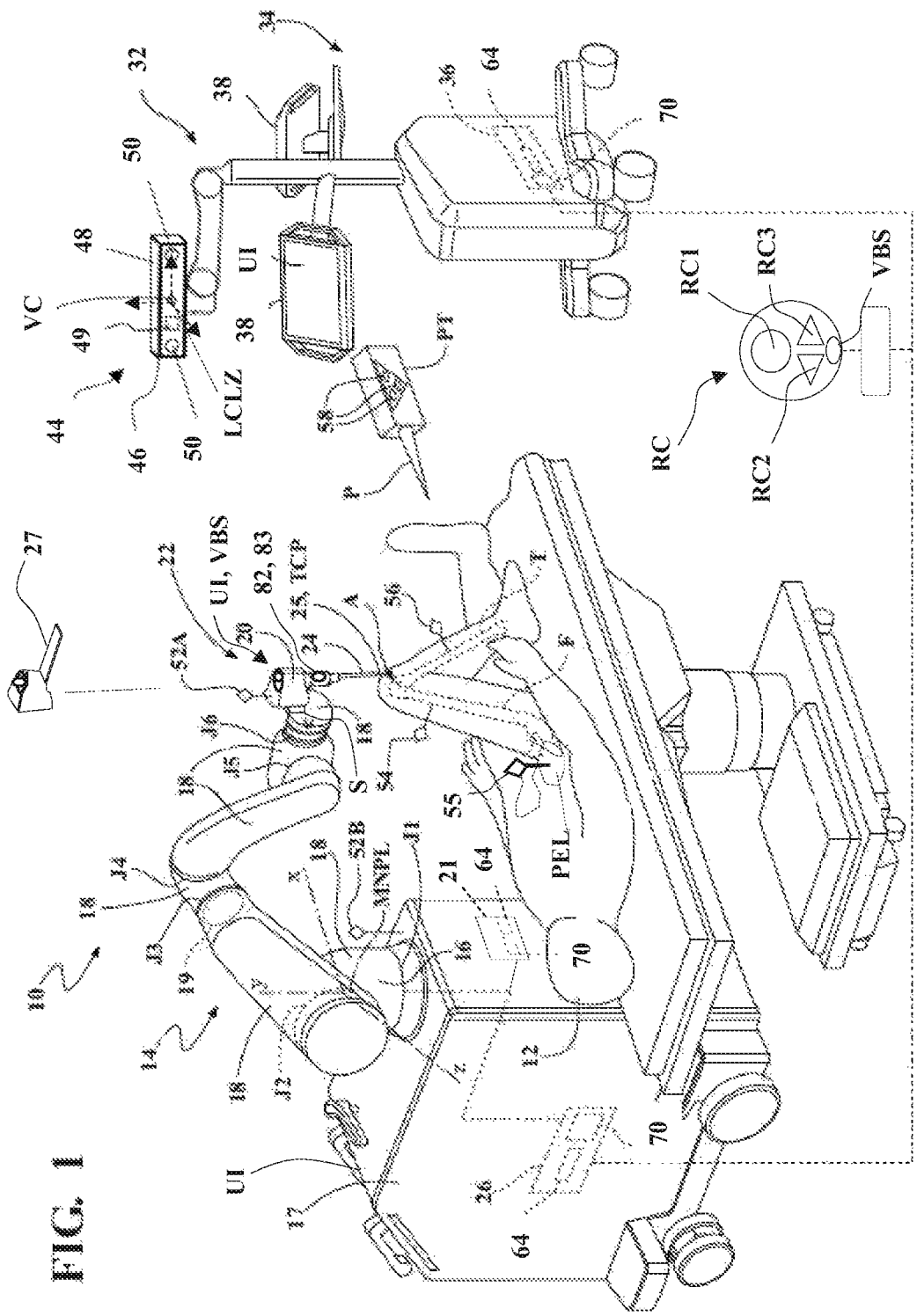
FIG. 1 is a perspective view of a surgical system.

Referring to FIG. 1, a surgical system 10 is illustrated. The system 10 is useful for treating a target site or anatomical volume A of a patient 12, such as treating bone or soft tissue. In FIG. 1, the patient 12 is undergoing a surgical procedure. The anatomy in FIG. 1 includes a femur F, pelvis PEL, and a tibia T of the patient 12. The surgical procedure may involve tissue removal or other forms of treatment. Treatment may include cutting, coagulating, lesioning the tissue, other in-situ tissue treatments, or the like. In some examples, the surgical procedure involves partial or total knee or hip replacement surgery, shoulder replacement surgery, spine surgery, or ankle surgery. In some examples, the system 10 is designed to cut away material to be replaced by surgical implants, such as hip and knee implants, including unicompartmental, bicompartmental, multicompartmental, or total knee implants, acetabular cup implants, femur stem implants, screws, anchors, other fasteners, and the like. Some of these types of implants are shown in U.S. Patent Application Publication No. 2012/0330429, entitled, "Prosthetic Implant and Method of Implantation," the disclosure of which is hereby incorporated by reference. The system 10 and techniques disclosed herein may be used to perform other procedures, surgical or non-surgical, or may be used in industrial applications or other applications.

The system 10 includes a robotic manipulator 14, also referred to as a surgical robot. The manipulator 14 has a base 16 and plurality of links 18. A manipulator cart 17 supports the manipulator 14 such that the manipulator 14 is fixed to the manipulator cart 17. The links 18 collectively form one or more arms of the manipulator 14 (e.g., robotic arms). The manipulator 14 may have a serial arm configuration (as shown in FIG. 1), a parallel arm configuration, or any other suitable manipulator configuration. In other examples, more than one manipulator 14 may be utilized in a multiple arm configuration.

In the example shown in FIG. 1, the manipulator 14 comprises a plurality of joints J and a plurality of joint encoders 19 located at the joints J for determining position data of the joints J. For simplicity, only one joint encoder 19 is illustrated in FIG. 1, although other joint encoders 19 may be similarly illustrated. The manipulator 14 according to one example has six joints J1-J6 implementing at least six-degrees of freedom (DOF) for the manipulator 14. However, the manipulator 14 may have any number of degrees of freedom and may have any suitable number of joints J and may have redundant joints.

The manipulator 14 need not require joint encoders 19 but may alternatively, or additionally, utilize motor encoders present on motors at each joint J. Also, the manipulator 14 need not require rotary joints, but may alternatively, or additionally, utilize one or more prismatic joints. Any suitable combination of joint types are contemplated.

The base 16 of the manipulator 14 is generally a portion of the manipulator 14 that provides a fixed reference coordinate system for other components of the manipulator 14 or the system 10 in general. Generally, the origin of a manipulator coordinate system MNPL is defined at the fixed reference of the base 16. The base 16 may be defined with respect to any suitable portion of the manipulator 14, such as one or more of the links 18. Alternatively, or additionally, the base 16 may be defined with respect to the manipulator cart 17, such as where the manipulator 14 is physically attached to the cart 17. In one example, the base 16 is defined at an intersection of the axes of joints J1 and J2. Thus, although joints J1 and J2 are moving components in reality, the intersection of the axes of joints J1 and J2 is nevertheless a virtual fixed reference pose, which provides both a fixed position and orientation reference and which does not move relative to the manipulator 14 and/or manipulator cart 17.

In some examples, the manipulator 14 can be a hand-held manipulator where the base 16 is a base portion of a tool (e.g., a portion held free-hand by the user) and the tool tip is movable relative to the base portion. The base portion has a reference coordinate system that is tracked and the tool tip has a tool tip coordinate system that is computed relative to the reference coordinate system (e.g., via motor and/or joint encoders and forward kinematic calculations). Movement of the tool tip can be controlled to follow the path since its pose relative to the path can be determined. Such a manipulator 14 is shown in U.S. Pat. No. 9,707,043, filed on Aug. 31, 2012, entitled, "Surgical Instrument Including Housing, A Cutting Accessory that Extends from the Housing and Actuators that Establish the Position of the Cutting Accessory Relative to the Housing," which is hereby incorporated herein by reference.

The manipulator 14 and/or manipulator cart 17 house a manipulator controller 26, or other type of control unit. The manipulator controller 26 may comprise one or more computers, or any other suitable form of controller that directs the motion of the manipulator 14. The manipulator controller 26 may have a central processing unit (CPU) and/or other processors, memory (not shown), and storage (not shown). The manipulator controller 26 is loaded with software as described below. The processors could include one or more processors to control operation of the manipulator 14. The processors can be any type of microprocessor, multi-processor, and/or multi-core processing system. The manipulator controller 26 may additionally, or alternatively, comprise one or more microcontrollers, field programmable gate arrays, systems on a chip, discrete circuitry, and/or other suitable hardware, software, or firmware that is capable of carrying out the functions described herein. The term processor is not intended to limit any embodiment to a single processor. The manipulator 14 may also comprise a user interface UI with one or more displays and/or input devices (e.g., push buttons, sensors, switches, keyboard, mouse, microphone (voice-activation), gesture control devices, touchscreens, joysticks, foot pedals, etc.).

A surgical tool 20 couples to the manipulator 14 and is movable relative to the base 16 to interact with the anatomy in certain modes. The tool 20 is or forms part of an end effector 22 supported by the manipulator 14 in certain embodiments. The tool 20 may be grasped by the user. One possible arrangement of the manipulator 14 and the tool 20 is described in U.S. Pat. No. 9,119,655, filed on Aug. 2, 2013, entitled, "Surgical Manipulator Capable of Controlling a Surgical Instrument in Multiple Modes," the disclosure of which is hereby incorporated by reference. The manipulator 14 and the tool 20 may be arranged in alternative configurations. The tool 20 can be like that shown in U.S. Patent Application Publication No. 2014/0276949, filed on Mar. 15, 2014, entitled, "End Effector of a Surgical Robotic Manipulator," hereby incorporated by reference.

The tool 20 includes an energy applicator 24 designed to contact the tissue of the patient 12 at the target site. In one example, the energy applicator 24 is a bur 25. The bur 25 may be substantially spherical and comprise a spherical center, radius (r) and diameter. Alternatively, the energy applicator 24 may be a drill bit, a saw blade 27 (see alternative tool in FIG. 1), an ultrasonic vibrating tip, or the like. The tool 20 and/or energy applicator 24 may comprise any geometric feature, e.g., perimeter, circumference, radius, diameter, width, length, volume, area, surface/plane, range of motion envelope (along any one or more axes), etc. The geometric feature may be considered to determine how to locate the tool 20 relative to the tissue at the target site to perform the desired treatment. In some of the embodiments described herein, a spherical bur having a tool center point (TCP) and a sagittal saw blade having a TCP will be described for convenience and ease of illustration, but is not intended to limit the tool 20 to any particular form.

The tool 20 may comprise a tool controller 21 to control operation of the tool 20, such as to control power to the tool 20 (e.g., to a tool drive such as a rotary motor of the tool 20), control movement of the tool 20, control irrigation/aspiration of the tool 20, and/or the like. The tool controller 21 may be in communication with the manipulator controller 26 or other components. The tool 20 may also comprise a user interface UI with one or more displays and/or input devices (e.g., push buttons, triggers, sensors, switches, keyboard, mouse, microphone (voice-activation), gesture control devices, touchscreens, joysticks, foot pedals, etc.) that are coupled to the tool controller 21, manipulator controller 26, and/or other controllers described herein. The manipulator controller 26 controls a state (e.g., position and/or orientation) of the tool 20 (e.g, of the TCP) with respect to a coordinate system, such as the manipulator coordinate system MNPL. The manipulator controller 26 can control velocity (linear or angular), acceleration, or other derivatives of motion of the tool 20.

The tool center point (TCP), in one example, is a predetermined reference point defined at the energy applicator 24. The TCP has a known, or able to be calculated (i.e., not necessarily static), pose relative to other coordinate systems. The geometry of the energy applicator 24 is known in or defined relative to a TCP coordinate system. The TCP may be located at the spherical center of the bur 25 of the tool 20 or at the distal end of the saw blade 27 such that only one point is tracked. The TCP may be defined in various ways depending on the configuration of the energy applicator 24. The manipulator 14 could employ the joint/motor encoders, or any other non-encoder position sensing method, to enable a pose of the TCP to be determined. The manipulator 14 may use joint measurements to determine TCP pose and/or could employ techniques to measure TCP pose directly. The control of the tool 20 is not limited to a center point. For example, any suitable primitives, meshes, etc., can be used to represent the tool 20.

The system 10 further includes a navigation system 32. One example of the navigation system 32 is described in U.S. Pat. No. 9,008,757, filed on Sep. 24, 2013, entitled, "Navigation System Including Optical and Non-Optical Sensors," hereby incorporated by reference. The navigation system 32 tracks movement of various objects. Such objects include, for example, the manipulator 14, the tool 20 and the anatomy, e.g., femur F, pelvis PEL, and tibia T. The navigation system 32 tracks these objects to gather state information of each object with respect to a (navigation) localizer coordinate system LCLZ. Coordinates in the localizer coordinate system LCLZ may be transformed to the manipulator coordinate system MNPL, to other coordinate systems, and/or vice-versa, using transformations.

The navigation system 32 includes a cart assembly 34 that houses a navigation controller 36, and/or other types of control units. A navigation user interface UI is in operative communication with the navigation controller 36. The navigation user interface includes one or more displays 38. The navigation system 32 is capable of displaying a graphical representation of the relative states of the tracked objects to the user using the one or more displays 38. The navigation user interface UI further comprises one or more input devices to input information into the navigation controller 36 or otherwise to select/control certain aspects of the navigation controller 36. Such input devices include interactive touchscreen displays. However, the input devices may include any one or more of push buttons, a keyboard, a mouse, a microphone (voice-activation), gesture control devices, foot pedals, and the like.

The navigation system 32 also includes a navigation localizer 44 coupled to the navigation controller 36. In one example, the localizer 44 is an optical localizer and includes a camera unit 46. The camera unit 46 has an outer casing 48 that houses one or more optical sensors 50. The localizer 44 may comprise its own localizer controller 49 and may further comprise a video camera VC.

The navigation system 32 includes one or more trackers. In one example, the trackers include a pointer tracker PT, one or more manipulator trackers 52A, 52B, a first patient tracker 54, a second patient tracker 55, and a third patient tracker 56. In the illustrated example of FIG. 1, the manipulator tracker is firmly attached to the tool 20 (i.e., tracker 52A), the first patient tracker 54 is firmly affixed to the femur F of the patient 12, the second patient tracker 55 is firmly affixed to the pelvis PEL of the patient 12, and the third patient tracker 56 is firmly affixed to the tibia T of the patient 12. In this example, the patient trackers 54, 55, 56 are firmly affixed to sections of bone. The pointer tracker PT is firmly affixed to a pointer P used for registering the anatomy to the localizer coordinate system LCLZ. The manipulator tracker 52A, 52B may be affixed to any suitable component of the manipulator 14, in addition to, or other than the tool 20, such as the base 16 (i.e., tracker 52B), or any one or more links 18 of the manipulator 14. The trackers 52A, 52B, 54, 55, 56, PT may be fixed to their respective components in any suitable manner. For example, the trackers may be rigidly fixed, flexibly connected (optical fiber), or not physically connected at all (ultrasound), as long as there is a suitable (supplemental) way to determine the relationship (measurement) of that respective tracker to the object with which it is associated.

Any one or more of the trackers may include active markers 58. The active markers 58 may include light emitting diodes (LEDs). Alternatively, the trackers 52A, 52B, 54, 55, 56, PT may have passive markers, such as reflectors, which reflect light emitted from the camera unit 46. Other suitable markers not specifically described herein may be utilized.

The localizer 44 tracks the trackers 52A, 52B, 54, 55, 56, PT to determine a state of each of the trackers 52A, 52B, 54, 55, 56, PT, which correspond respectively to the state of the object respectively attached thereto. The localizer 44 may perform known triangulation techniques to determine the states of the trackers 52, 54, 55, 56, PT, and associated objects. The localizer 44 provides the state of the trackers 52A, 52B, 54, 55, 56, PT to the navigation controller 36. In one example, the navigation controller 36 determines and communicates the state the trackers 52A, 52B, 54, 55, 56, PT to the manipulator controller 26. As used herein, the state of an object includes, but is not limited to, data that defines the position and/or orientation of the tracked object or equivalents/derivatives of the position and/or orientation. For example, the state may be a pose of the object, and may include linear velocity data, and/or angular velocity data, and the like.

The navigation controller 36 may comprise one or more computers, or any other suitable form of controller. Navigation controller 36 has a central processing unit (CPU) and/or other processors, memory (not shown), and storage (not shown). The processors can be any type of processor, microprocessor or multi-processor system. The navigation controller 36 is loaded with software. The software, for example, converts the signals received from the localizer 44 into data representative of the position and orientation of the objects being tracked. The navigation controller 36 may additionally, or alternatively, comprise one or more microcontrollers, field programmable gate arrays, systems on a chip, discrete circuitry, and/or other suitable hardware, software, or firmware that is capable of carrying out the functions described herein. The term processor is not intended to limit any embodiment to a single processor.

Although one example of the navigation system 32 is shown that employs triangulation techniques to determine object states, the navigation system 32 may have any other suitable configuration for tracking the manipulator 14, tool 20, and/or the patient 12. In another example, the navigation system 32 and/or localizer 44 are ultrasound-based. For example, the navigation system 32 may comprise an ultrasound imaging device coupled to the navigation controller 36. The ultrasound imaging device images any of the aforementioned objects, e.g., the manipulator 14, the tool 20, and/or the patient 12, and generates state signals to the navigation controller 36 based on the ultrasound images. The ultrasound images may be 2-D, 3-D, or a combination of both. The navigation controller 36 may process the images in near real-time to determine states of the objects. The ultrasound imaging device may have any suitable configuration and may be different than the camera unit 46 as shown in FIG. 1.

In another example, the navigation system 32 and/or localizer 44 are radio frequency (RF)-based. For example, the navigation system 32 may comprise an RF transceiver coupled to the navigation controller 36. The manipulator 14, the tool 20, and/or the patient 12 may comprise RF emitters or transponders attached thereto. The RF emitters or transponders may be passive or actively energized. The RF transceiver transmits an RF tracking signal and generates state signals to the navigation controller 36 based on RF signals received from the RF emitters. The navigation controller 36 may analyze the received RF signals to associate relative states thereto. The RF signals may be of any suitable frequency. The RF transceiver may be positioned at any suitable location to track the objects using RF signals effectively. Furthermore, the RF emitters or transponders may have any suitable structural configuration that may be much different than the trackers 52A, 52B, 54, 55, 56, PT shown in FIG. 1.

In yet another example, the navigation system 32 and/or localizer 44 are electromagnetically based. For example, the navigation system 32 may comprise an EM transceiver coupled to the navigation controller 36. The manipulator 14, the tool 20, and/or the patient 12 may comprise EM components attached thereto, such as any suitable magnetic tracker, electro-magnetic tracker, inductive tracker, or the like. The trackers may be passive or actively energized. The EM transceiver generates an EM field and generates state signals to the navigation controller 36 based upon EM signals received from the trackers. The navigation controller 36 may analyze the received EM signals to associate relative states thereto. Again, such navigation system 32 examples may have structural configurations that are different than the navigation system 32 configuration shown in FIG. 1.

The navigation system 32 may have any other suitable components or structure not specifically recited herein. Furthermore, any of the techniques, methods, and/or components described above with respect to the navigation system 32 shown may be implemented or provided for any of the other examples of the navigation system 32 described herein. For example, the navigation system 32 may utilize solely inertial tracking or any combination of tracking techniques, and may additionally or alternatively comprise, fiber optic-based tracking, machine-vision tracking, and the like.

Figure 2:
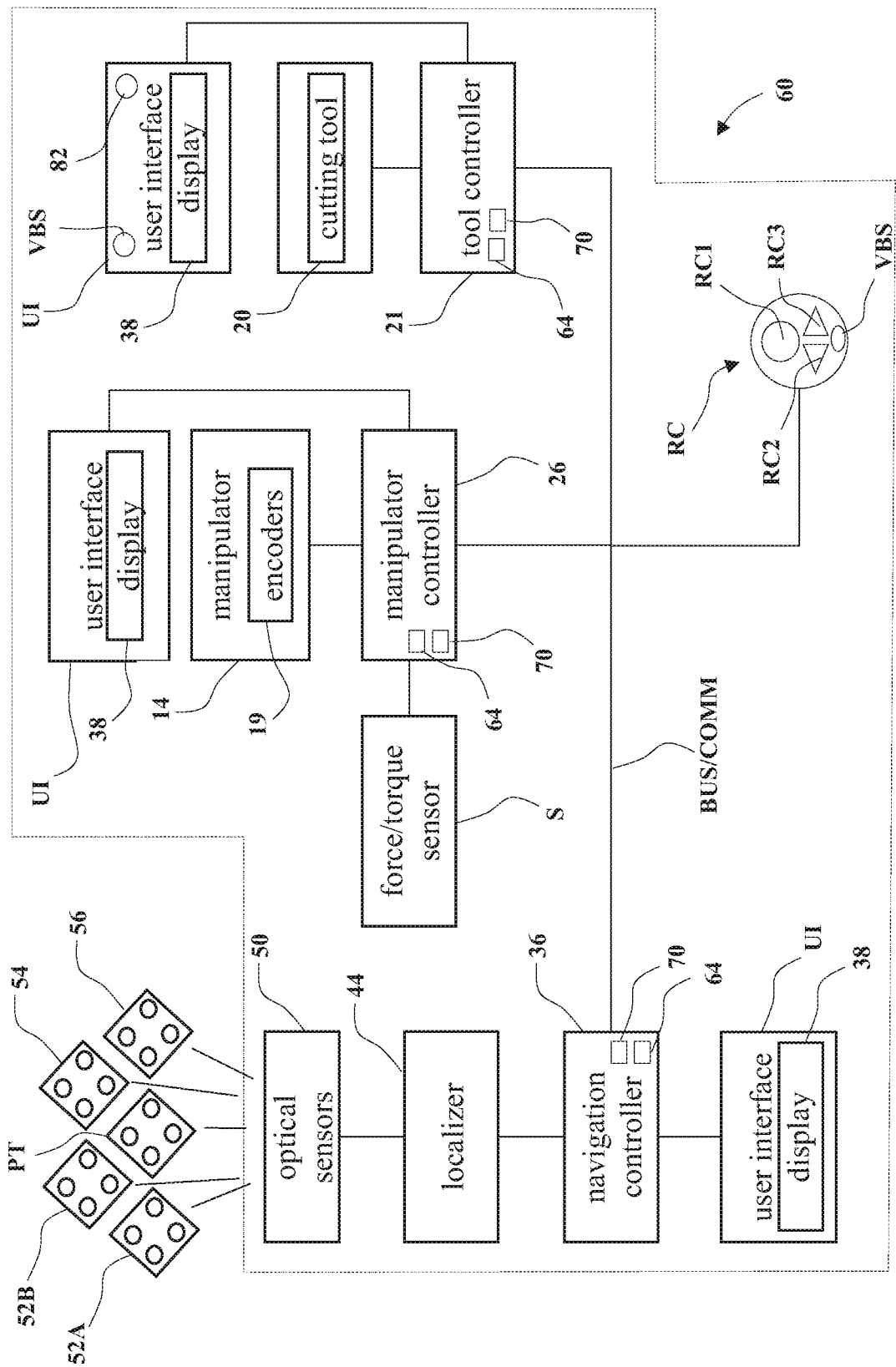
FIG. 2 is a block diagram of a control system for controlling the surgical system.

Referring to FIG. 2, the system 10 includes a control system 60 that comprises, among other components, the manipulator controller 26, the navigation controller 36, and the tool controller 21. The control system 60 further includes one or more software programs and software modules shown in FIG. 3. The software modules may be part of the program or programs that operate on the manipulator controller 26, navigation controller 36, tool controller 21, or any combination thereof, to process data to assist with control of the system 10. The software programs and/or modules include computer readable instructions stored in non-transitory memory 64 on the manipulator controller 26, navigation controller 36, tool controller 21, or a combination thereof, to be executed by one or more processors 70 of the controllers 21, 26, 36. The memory 64 may be any suitable configuration of memory, such as RAM, non-volatile memory, etc., and may be implemented locally or from a remote database. Additionally, software modules for prompting and/or communicating with the user may form part of the program or programs and may include instructions stored in memory 64 on the manipulator controller 26, navigation controller 36, tool controller 21, or any combination thereof. The user may interact with any of the input devices of the navigation user interface UI or other user interface UI to communicate with the software modules. The user interface software may run on a separate device from the manipulator controller 26, navigation controller 36, and/or tool controller 21.

The control system 60 may comprise any suitable configuration of input, output, and processing devices suitable for carrying out the functions and methods described herein. The control system 60 may comprise the manipulator controller 26, the navigation controller 36, or the tool controller 21, or any combination thereof, or may comprise only one of these controllers. These controllers may communicate via a wired bus or communication network as shown in FIG. 2, via wireless communication, or otherwise. The control system 60 may also be referred to as a controller. The control system 60 may comprise one or more microcontrollers, field programmable gate arrays, systems on a chip, discrete circuitry, sensors, displays, user interfaces, indicators, and/or other suitable hardware, software, or firmware that is capable of carrying out the functions described herein.

II. Virtual Boundaries and Tool Paths

Figure 3:
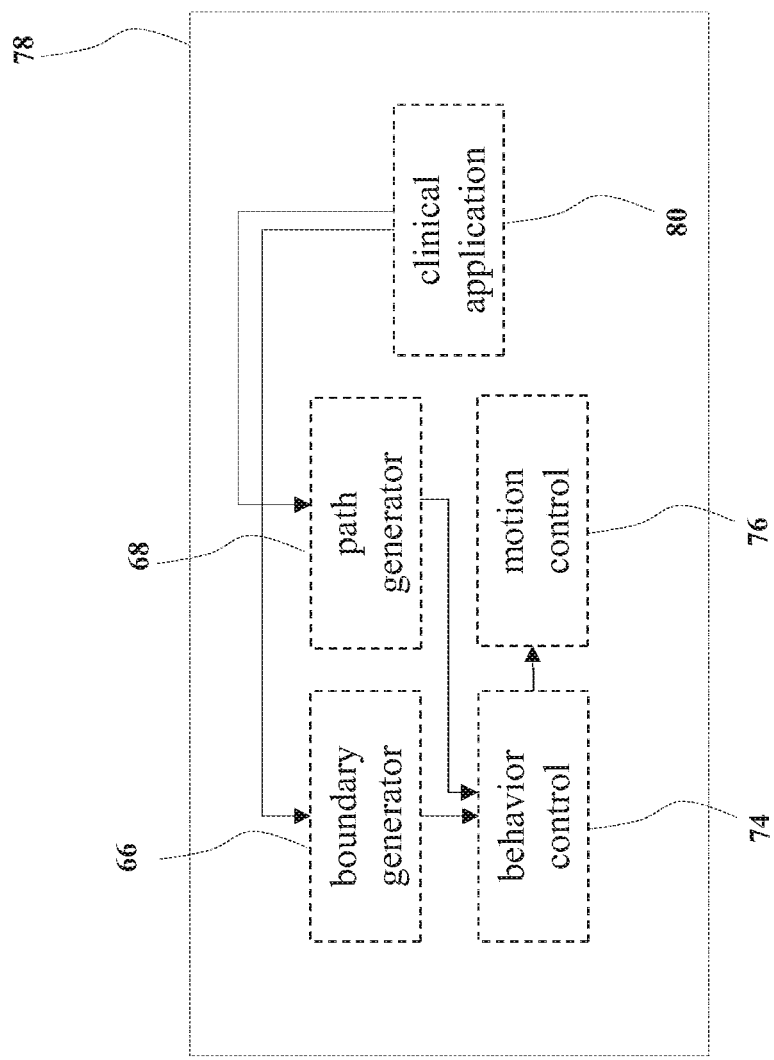
FIG. 3 is a functional block diagram of a software program.
Figure 4:
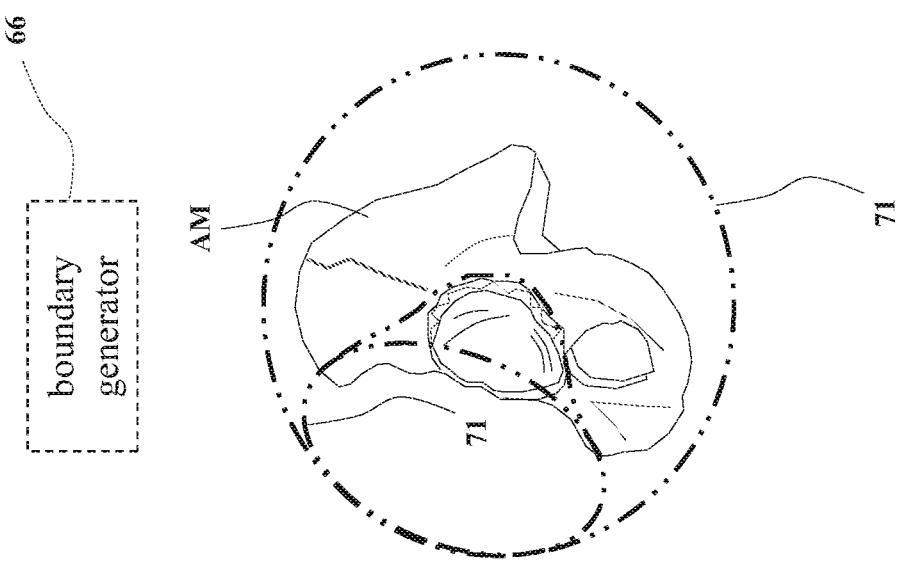
FIG. 4 illustrates output of a boundary generator for a surgical procedure on an acetabulum.

Referring to FIG. 3, the software employed by the control system 60 includes a boundary generator 66. As shown in FIG. 4, the boundary generator 66 is a software program or module that generates a virtual boundary 71 for constraining movement and/or operation of the tool 20. The virtual boundary 71 may be one-dimensional, two-dimensional, three-dimensional, and may comprise a point, line, axis, trajectory, plane, volume, triangle mesh, or the like. The virtual boundary 71 may have a simple shape or complex geometric shape. In some embodiments, the virtual boundary 71 is a surface defined by a triangle mesh. The virtual boundaries 71 may also be referred to as virtual objects. The virtual boundaries 71 may be, for example, keep-in boundaries where it's desirable for the tool 20 to be kept within a volume defined by the boundary, or keep-out boundaries where it's desirable for the tool 20 to be kept out of a volume defined by the boundary. The virtual boundaries 71 may also be keep-on boundaries where it's desirable for the tool 20 to be kept on a point, line, plane, surface, etc. defining the boundary, or keep-off boundaries where it's desirable for the tool 20 to be kept off a point, line, plane, surface, etc. defining the boundary. The virtual boundaries 71 may also be combinations of these types of boundaries. Other types of boundaries are also contemplated.

The virtual boundaries 71 may be defined with respect to an anatomical model AM, such as a 3-D bone model. The anatomical model AM is associated with the real patient anatomy by virtue of the anatomical model AM being mapped to the patient's anatomy via registration or other process. In the example of FIG. 4, the virtual boundary 71 comprises a generally spherical mesh substantially surrounding an acetabulum with an entry portion 71a (opening) that provides access to the acetabulum. The entry portion has a funnel or conical shape. This virtual boundary 71 is associated with a 3-D model of the acetabulum.

The anatomical model AM and associated virtual boundaries 71 are registered to the one or more patient trackers 54, 55, 56. Thus, the anatomical model AM (and associated real patient anatomy) and the virtual boundaries 71 fixed to the anatomical model AM can be tracked by the patient trackers 54, 55, 56. The virtual boundaries 71 may be implant-specific, e.g., defined based on a size, shape, volume, etc. of an implant and/or patient-specific, e.g., defined based on the patient's anatomy. The virtual boundaries 71 may be boundaries that are created pre-operatively, intra-operatively, or combinations thereof. In other words, the virtual boundaries 71 may be defined before the surgical procedure begins, during the surgical procedure (including during tissue removal), or combinations thereof. In any case, the control system 60 obtains the virtual boundaries 71 by storing/retrieving the virtual boundaries 71 in/from memory, obtaining the virtual boundaries 71 from memory, creating the virtual boundaries 71 pre-operatively, creating the virtual boundaries 71 intra-operatively, or the like.

The manipulator controller 26 and/or the navigation controller 36 track the state of the tool 20 relative to one or more virtual boundaries 71. In one example, the state of the TCP is measured relative to a virtual boundary 71 for purposes of determining forces to be applied to a virtual rigid body model of the tool 20 via a virtual simulation so that the tool 20 remains in compliance with the virtual boundary. The tool 20 remains in compliance with the virtual boundary by remaining in a desired relationship to the virtual boundary 71, such as not being moved beyond it, and/or maintaining a desired position and/or orientation relative to the virtual boundary 71. It should be appreciated that a predefined, configurable tolerance may also be established for any virtual boundary 71 such that some penetrations of the virtual boundary 71 by the tool 20 or deviations from perfect compliance with the virtual boundary 71 are not considered violations of the virtual boundary 71. For instance, a small tolerance could be set at 0.1 millimeters (mm) such that the tool 20 remains in compliance with the virtual boundary 71 so long as the tool 20 penetrates less than 0.1 mm into the virtual boundary 71 (i.e., this would not be considered a violation of the virtual boundary 71). In some cases, larger tolerances may be appropriate. The results of the virtual simulation are commanded to the manipulator 14. The control system 60 controls/positions the manipulator 14 in a manner that emulates the way a physical handpiece would respond in the presence of physical boundaries/barriers. The boundary generator 66 may be implemented on the manipulator controller 26. Alternatively, the boundary generator 66 may be implemented on other components, such as the navigation controller 36.

Figure 5:
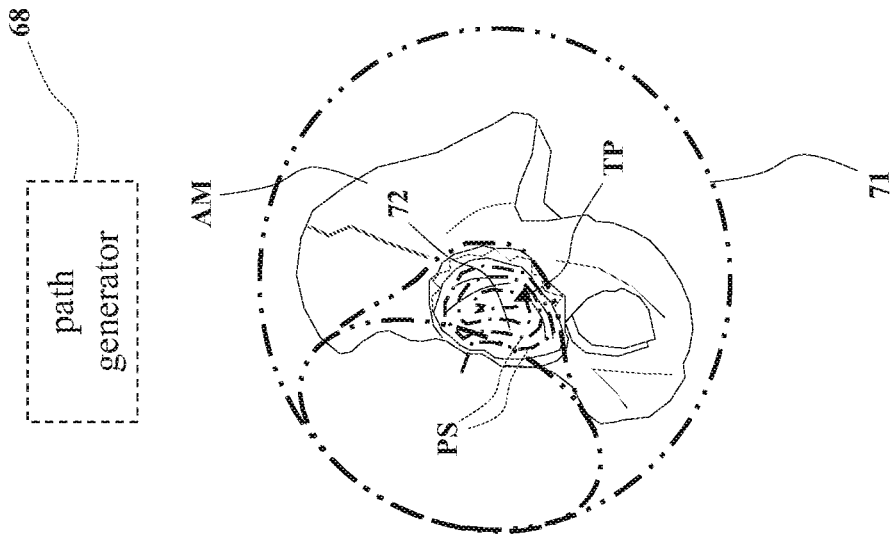
FIG. 5 illustrates output of a path generator for the surgical procedure on the acetabulum.

Referring to FIGS. 3 and 5, a path generator 68 is another software program or module run by the control system 60. In one example, the path generator 68 is run by the manipulator controller 26. The path generator 68 generates a tool path TP for the tool 20 to traverse, such as for removing sections of the anatomy to receive an implant. The tool path TP may comprise a plurality of path segments PS, or may comprise a single path segment PS. The path segments PS may be straight segments, curved segments, combinations thereof, or the like. The tool path TP may also be defined with respect to the anatomical model AM and may be tracked via one or more of the patient trackers 54, 55, 56. The tool path TP may be implant-specific, e.g., defined based on a size, shape, volume, etc. of an implant and/or patient-specific, e.g., defined based on the patient's anatomy. The tool path TP may be a 3-D path along which the TCP of the tool 20 is intended to move during certain operations of the system 10.

In one version described herein, the tool path TP is defined as a tissue removal path, but, in other versions, the tool path TP may be used for treatment other than tissue removal. One example of the tissue removal path described herein comprises a milling path 72. It should be understood that the term "milling path" generally refers to the path of the tool 20 in the vicinity of the target site for milling the anatomy and is not intended to require that the tool 20 be operably milling the anatomy throughout the entire duration of the path. For instance, the milling path 72 may comprise sections or segments where the tool 20 transitions from one location to another without milling Additionally, other forms of tissue removal along the milling path 72 may be employed, such as tissue ablation, and the like. The milling path 72 may be a predefined path that is created pre-operatively, intra-operatively, or combinations thereof. In other words, the milling path 72 may be defined before the surgical procedure begins, during the surgical procedure (including during tissue removal), or combinations thereof. In any case, the control system 60 obtains the milling path 72 by storing/retrieving the milling path 72 in/from memory, obtaining the milling path 72 from memory, creating the milling path 72 pre-operatively, creating the milling path 72 intra-operatively, or the like. The milling path 72 may have any suitable shape, or combinations of shapes, such as circular, helical/corkscrew, linear, curvilinear, combinations thereof, and the like. The milling path 72 shown in FIG. 5, when traversed by the tool 20, is intended to remove material from the acetabulum to make room for an acetabular cup implant to be fitted to the acetabulum.

Example virtual boundaries 71 and/or milling paths 72 are shown in FIGS. 4-9. The particular shapes and arrangements of the virtual boundaries 71 and/or milling paths 72 shown are for illustrative purposes. Other shapes and arrangements are possible. As previously described, FIGS. 4 and 5 illustrate a virtual boundary 71 and a milling path 72 that are generated for use in a surgical procedure in which the acetabulum is being prepared (e.g., milled) to receive an acetabular cup implant.

Figure 6:
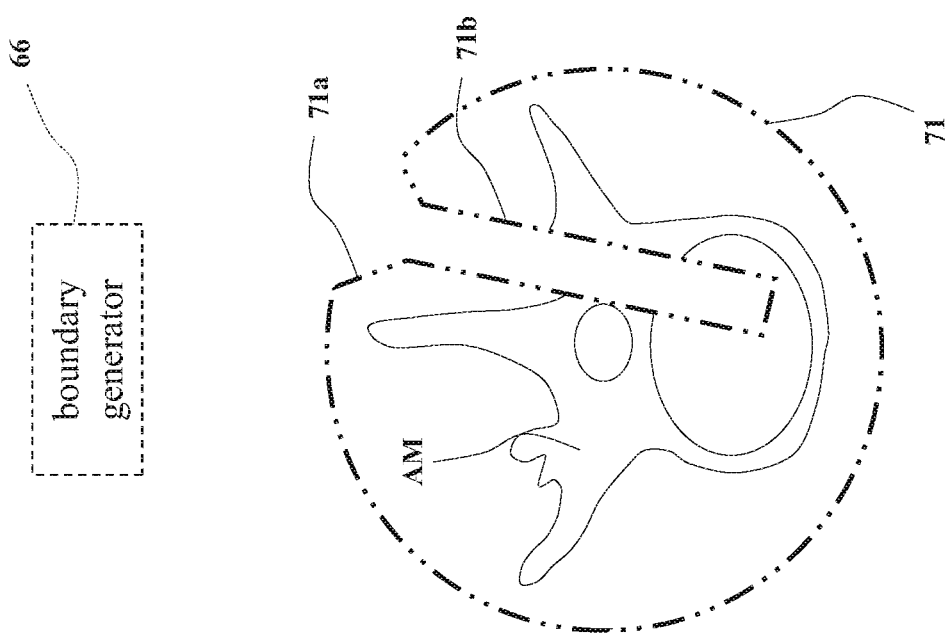
FIG. 6 illustrates output of a boundary generator for a surgical procedure on a vertebral body.

FIG. 6 illustrates a virtual boundary 71 comprising a generally spherical mesh substantially surrounding a vertebral body with an entry portion 71a (opening) that provides access to the vertebral body. The entry portion 71a has a funnel or conical shape and extends into a cylindrical portion 71b. This virtual boundary 71 is associated with a 3-D model of the vertebral body. This virtual boundary 71 is generated for use in a surgical procedure in which the vertebral body is being prepared (e.g. milled) to receive a screw or other implant.

Figure 8:
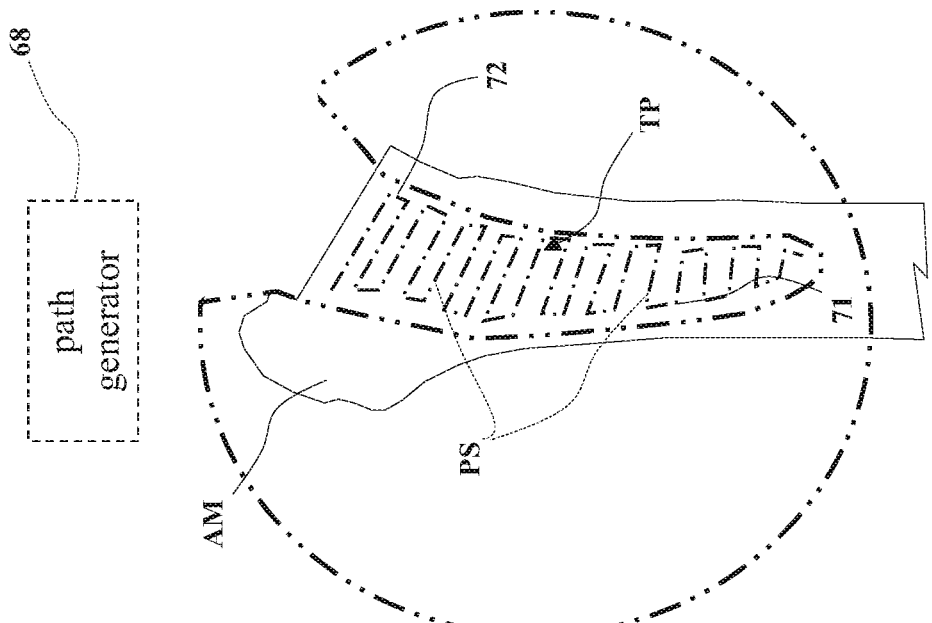
FIG. 8 illustrates output of a path generator for the surgical procedure on the femur.
Figure 7:
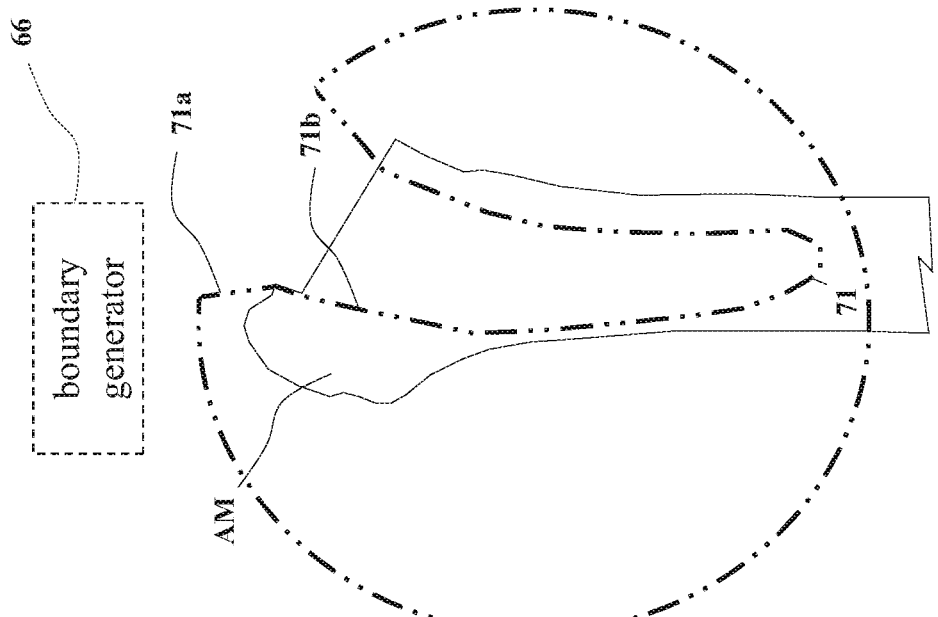
FIG. 7 illustrates output of a boundary generator for a surgical procedure on a femur.

FIG. 7 illustrates a virtual boundary 71 comprising a generally spherical mesh substantially surrounding one end of a femur with an entry portion 71a (opening) providing access to the femur. The entry portion 71a has a funnel or conical shape and extends to a canal portion 71b continuing down a medullary canal of the femur. This virtual boundary 71 is associated with a 3-D model of the femur. FIG. 8 illustrates a milling path 72 defined so that the tool 20 is able to remove material from the femur to make way for a femur stem implant. Thus, FIGS. 7 and 8 illustrate a virtual boundary 71 and a milling path 72 that are generated for use in a surgical procedure in which the femur F is being prepared (e.g., milled) to receive the femur stem implant.

Figure 9:
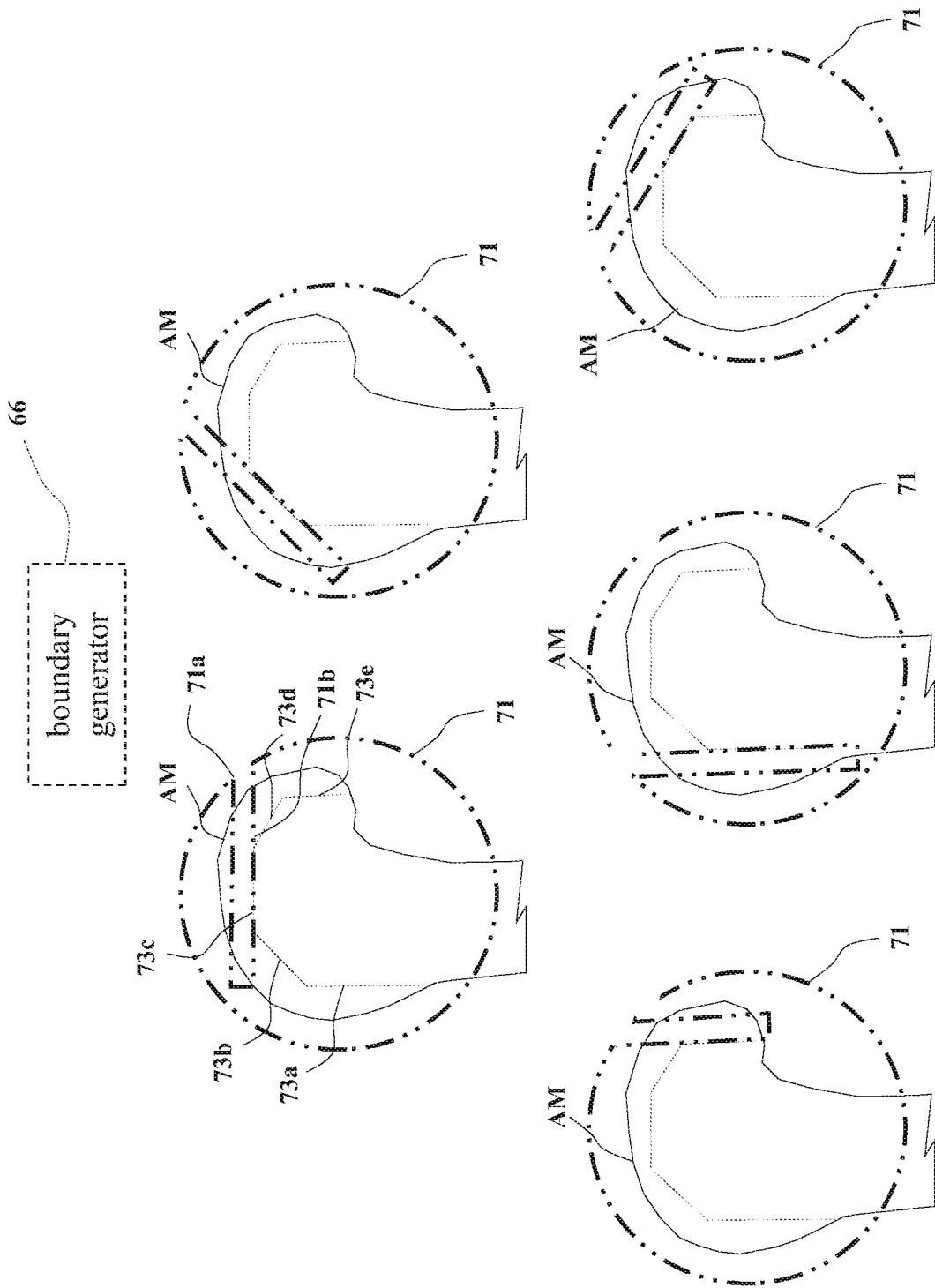
FIG. 9 illustrates output of a boundary generator for a surgical procedure on a femur.

FIG. 9 illustrates a series of virtual boundaries 71 that are generated for five cutting planes through a distal end of a femur. Each of the virtual boundaries 71 in FIG. 9 comprises a generally spherical mesh substantially surrounding the distal end of the femur with an entry portion 71a (opening) that provides access to the femur. The entry portion 71a continues into a cutting slot 71b defined along one of the five cutting planes 73a-73e. These virtual boundaries 71 are generated for use in a surgical procedure in which the femur F is being prepared (e.g., via planar resections) to receive a total knee implant. Other types/shapes of virtual boundaries and/or milling paths 72 are contemplated for use in other surgical procedures.

One example of a system and method for generating the virtual boundaries 71 and/or the milling path 72 is described in U.S. Pat. No. 9,119,655, entitled, "Surgical Manipulator Capable of Controlling a Surgical Instrument in Multiple Modes," the disclosure of which is hereby incorporated by reference. In some examples, the virtual boundaries 71 and/or milling paths 72 may be generated offline rather than on the manipulator controller 26 or navigation controller 36. Thereafter, the virtual boundaries 71 and/or milling paths 72 may be utilized at runtime by the manipulator controller 26.

Referring back to FIG. 3, two additional software programs or modules run on the manipulator controller 26 and/or the navigation controller 36. One software module performs behavior control 74. Behavior control 74 is the process of computing data that indicates the next commanded position and/or orientation (e.g., pose) for the tool 20. In some cases, only the position of the TCP is output from the behavior control 74, while in other cases, the position and orientation of the tool 20 is output. Output from the boundary generator 66, the path generator 68, and one or more sensors, such as a force/torque sensor S, may feed as inputs into the behavior control 74 to determine the next commanded position and/or orientation for the tool 20. The behavior control 74 may process these inputs, along with one or more virtual constraints described further below, to determine the commanded pose.

The second software module performs motion control 76. One aspect of motion control is the control of the manipulator 14. The motion control 76 receives data defining the next commanded pose from the behavior control 74. Based on these data, the motion control 76 determines the next position of the joint angles of the joints J of the manipulator 14 (e.g., via inverse kinematics and Jacobian calculators) so that the manipulator 14 is able to position the tool 20 as commanded by the behavior control 74, e.g., at the commanded pose. In other words, the motion control 76 processes the commanded pose, which may be defined in Cartesian space, into joint angles of the manipulator 14, so that the manipulator controller 26 can command the joint motors accordingly, to move the joints J of the manipulator 14 to commanded joint angles corresponding to the commanded pose of the tool 20. In one version, the motion control 76 regulates the joint angle of each joint J and continually adjusts the torque that each joint motor outputs to, as closely as possible, ensure that the joint motor drives the associated joint J to the commanded joint angle.

The boundary generator 66, path generator 68, behavior control 74, and motion control 76 may be sub-sets of a software program 78. Alternatively, each may be software programs that operate separately and/or independently in any combination thereof. The term "software program" is used herein to describe the computer-executable instructions that are configured to carry out the various capabilities of the technical solutions described. For simplicity, the term "software program" is intended to encompass, at least, any one or more of the boundary generator 66, path generator 68, behavior control 74, and/or motion control 76. The software program 78 can be implemented on the manipulator controller 26, navigation controller 36, or any combination thereof, or may be implemented in any suitable manner by the control system 60.

A clinical application 80 may be provided to handle user interaction. The clinical application 80 handles many aspects of user interaction and coordinates the surgical workflow, including pre-operative planning, implant placement, registration, bone preparation visualization, and post-operative evaluation of implant fit, etc. The clinical application 80 is configured to output to the displays 38. The clinical application 80 may run on its own separate processor or may run alongside the navigation controller 36. In one example, the clinical application 80 interfaces with the boundary generator 66 and/or path generator 68 after implant placement is set by the user, and then sends the virtual boundary 71 and/or tool path TP returned by the boundary generator 66 and/or path generator 68 to the manipulator controller 26 for execution. Manipulator controller 26 executes the tool path TP as described herein. The manipulator controller 26 may additionally create certain segments (e.g., lead-in segments) when starting or resuming machining to smoothly get back to the generated tool path TP. The manipulator controller 26 may also process the virtual boundaries 71 to generate corresponding virtual constraints as described further below.

III. Modes of Operation

The system 10 may operate in a manual mode, such as described in U.S. Pat. No. 9,119,655, incorporated herein by reference. Here, the user manually directs, and the manipulator 14 executes movement of the tool 20 and its energy applicator 24 at the target site. The user physically contacts the tool 20 to cause movement of the tool 20 in the manual mode. In one version, the manipulator 14 monitors forces and torques placed on the tool 20 by the user in order to position the tool 20. For example, the manipulator 14 may comprise the one or more sensors (e.g., the force/torque sensor S) that detects and measures the forces and torques applied by the user to the tool 20 and generates corresponding input used by the control system 60 (e.g., one or more corresponding input/output signals). The forces and torques applied by the user at least partially define an external force $F_{ext}$ that is used to determine how to move the tool 20 in the manual mode. The external force $F_{ext}$ may comprise other forces and torques, aside from those applied by the user, such as gravity-compensating forces, backdrive forces, and the like, as described in U.S. Pat. No. 9,119,655, incorporated herein by reference. Thus, the forces and torques applied by the user at least partially define the external force $F_{ext}$, and in some cases may fully define the external force $F_{ext}$ that influences overall movement of the tool 20 in the manual mode.

The force/torque sensor S may comprise a 6-DOF force/torque transducer, as disclosed, for example, in U.S. Pat. No. 9,119,655, incorporated herein by reference. The force/torque sensor S may form part of the tool 20, the manipulator 14, or both. The force/torque sensor S may form part of an interface between the tool 20 and the manipulator 14, or may be placed in any suitable location so that forces and torques applied by the user to the tool 20 are transmitted to the force/torque sensor S. The manipulator controller 26 and/or the navigation controller 36 receives the input (e.g., signals) from the force/torque sensor S. In response to the forces and torques applied by the user, the manipulator 14 moves the tool 20 in a manner that emulates the movement that would have occurred based on the forces and torques applied by the user.

Movement of the tool 20 in the manual mode may also be constrained (e.g., limited) in relation to the one or more virtual boundaries 71 generated by the boundary generator 66. In some versions, measurements taken by the force/torque sensor S are transformed from a force/torque coordinate system FT of the force/torque sensor S to another coordinate system, such as a virtual mass coordinate system VM in which a virtual simulation is carried out on the virtual rigid body model of the tool 20 so that the forces and torques can be virtually applied to the virtual rigid body in the virtual simulation to ultimately determine how those forces and torques (among other inputs) would affect movement of the virtual rigid body, as described below.

The system 10 may also operate in a semi-autonomous mode in which the manipulator 14 autonomously moves the tool 20 along the milling path 72 (e.g., the active joints J of the manipulator 14 operate to move the tool 20 without requiring force/torque on the tool 20 from the user). An example of operation in the semi-autonomous mode is also described in U.S. Pat. No. 9,119,655, incorporated herein by reference. In some embodiments, when the manipulator 14 operates in the semi-autonomous mode, the manipulator 14 is capable of moving the tool 20 free of user assistance. Free of user assistance may mean that a user does not physically contact the tool 20 to move the tool 20. Instead, the user may use a remote control RC (see FIG. 1) that is in communication with the manipulator 14 (e.g., wired or wireless) to control starting and stopping of movement. The remote control RC may be in the form of a pendant that is held in the hand of the user or otherwise gripped or supported by the user. The pendant may have any suitable size and/or shape to enable the user to hold and operate the pendant. In some versions, the pendant is a portable electronic device.

The user interface UI of the tool 20 and the remote control RC may each include one or more user input devices (e.g., push buttons, sensors, switches, keyboard, mouse, microphone (voice-activation), gesture control devices, touchscreens, joysticks, foot pedals, etc.) that are coupled to the tool controller 21, manipulator controller 26, and/or navigation controller 36, to control operation of the manipulator 14. For example, one of the user input devices on the user interface UI of the tool 20 may be a tool input 82 (e.g., switch or other form of user input device) that has first and second input states (see FIG. 1). The tool input 82 can be actuated (e.g., pressed and held) by the user to be placed in the first input state and can be released to be placed in the second input state. The tool 20 may have a grip 83 on which the tool input 82 is located. In some versions, the tool input 82 is a presence detector that detects the presence of a hand of the user, such as a momentary contact switch that switches between on/off states, a capacitive sensor, an optical sensor, or the like. The tool input 82 is thus configured such that the first input state indicates that a user is actively engaging the tool 20 and the second input state indicates that the user has released the tool 20.

One of the input devices on the remote control RC may be a pendant input RC1 (e.g., switch or other form of user input device) that has first and second input states. Like the tool input 82, the pendant input RC1 can be actuated (e.g., pressed and held) by the user to be placed in the first input state and can be released to be placed in the second input state. When the pendant input RC1 is actuated, secondary pendant inputs RC2, RC3 on the remote control RC (e.g., switches or other forms of user input devices) may then cause movement of the manipulator 14 by controlling a feed rate of the manipulator 14, e.g., a speed at which the manipulator 14 moves the tool 20. For instance, secondary pendant input RC2 may slow the feed rate and secondary pendant input RC3 may increase the feed rate in the semi-autonomous mode. Such a remote control RC embodied as a user pendant is disclosed in U.S. Pat. No. 10,117,713 to Moctezuma de La Barrera et al., entitled "Robotic Systems and Methods for Controlling a Tool Removing Material from a Workpiece," which is hereby incorporated herein by reference.

The tool input 82 and the pendant input RC1 may be forms of continuous activation devices, i.e., inputs that must be continually actuated to allow motion of the tool 20 in the manual mode or the semi-autonomous mode, depending on which user input is actuated. For example, while the user is continually actuating the tool input 82, and the manual mode is enabled, the manipulator 14 will move in response to the input forces and torques applied by the user and the control system 60 will enforce the virtual boundary 71 to protect the patient anatomy. When the tool input 82 is released, input from the force/torque sensor S may be disabled such that the manipulator 14 no longer responds to the forces and torques applied by the user to the tool 20.

Under normal operating conditions, when the tool input 82 is in the first input state (e.g., actuated), and regardless of the state of the pendant input RC1 (tool input 82 has priority), the manipulator 14 is operated in the manual mode and the control system 60 operates in a boundary-enabled state to maintain the tool 20 in compliance with the virtual boundary 71 (or boundaries) being employed by the control system 60 at the time. Similarly, under normal operating conditions, when the tool input 82 is in the second input state (e.g., released) and the pendant input RC1 is in the first input state (e.g., actuated), the manipulator 14 is operated in the semi-autonomous mode and the control system 60 operates in the boundary-enabled state to maintain the tool 20 in compliance with the virtual boundary 71 and in compliance with the tool path TP.

In the boundary-enabled state, the control system 60 controls operation of the manipulator 14 to maintain the tool 20 in compliance with the virtual boundary 71. As a result, in the boundary-enabled state, the control system 60 is capable of controlling the manipulator 14 to cause autonomous movement of the tool 20 so that if the virtual boundary 71 moves relative to the tool 20 in a manner that would otherwise cause the tool 20 to violate the virtual boundary 71, the control system 60 can compensate for such movement of the virtual boundary 71 by moving the tool 20. Such autonomous movement may be referred to as autonomous, boundary-complying movement. For example, if the manipulator 14 is operating in the manual mode, but the user has ceased causing any movement of the tool 20, e.g., the user is still actuating the tool input 82, but is not applying any user forces or torques on the tool 20, and the patient's anatomy is moved in such a way that the virtual boundary 71 (which is fixed relative to the patient's anatomy) moves slightly beyond the TCP of the tool 20, then the control system 60 will react by actuating one or more of the joint motors on the manipulator 14 in a manner that provides compensating movement of the tool 20 to keep the TCP of the tool 20 in compliance with the virtual boundary 71.

When the tool input 82 and the pendant input RC1 are both in the second input state (e.g., neither have been actuated), then the manipulator 14 operates in a hold mode and in a boundary-disabled state. In the hold mode, movement of the tool 20 is effectively disabled. In this case, the manipulator 14 may still be energized and operating to actively hold the current position and/or orientation of the tool 20 relative to the manipulator coordinate system MNPL by monitoring the encoders 19 and actively driving the joint motors to resist external forces due to gravity or forces that are inadvertently applied on the manipulator 14 or tool 20 by the user. In some versions, a braking system may be engaged to hold the tool 20 in the current position and/or orientation. In the hold mode, the user may desire to adjust positioning of the patient's anatomy and the target site without resulting in any unexpected movement of the tool 20, e.g., so that movement of the tool 20 occurs only in response to input from the user. The user may want to adjust the patient's anatomy for various reasons, such as visualization, to improve access to the target site, to allow cleaning of the target site, to remove or clean soft tissue, etc. In any case, if the patient's anatomy has moved, so too has any virtual boundary 71 that is fixed in pose relative to the patient's anatomy.

In the hold mode and the boundary-disabled state, the control system 60 disables any autonomous, boundary-complying movement of the tool 20. As a result, once the user has finished moving the patient's anatomy to improve visualization, access, or otherwise, and is ready to restart operation of the manipulator 14 in the manual mode or the semi-autonomous mode, the system 10 first checks to see if the virtual boundary 71 has moved in a manner in which the tool 20 is now in violation of the virtual boundary 71 (e.g., outside the virtual boundary 71, inside the virtual boundary 71, deviating from the virtual boundary 71, etc.). Accordingly, when switching back to the manual mode or the semi-autonomous mode by switching the tool input 82 or the pendant input RC1 to the first input state, the control system 60 performs a collision check to determine if the TCP of the tool 20 is now in violation of the virtual boundary 71.

If a collision is detected, then the manual mode or the semi-autonomous mode (depending on which input was actuated), remains disabled and the control system 60 acts to provide guidance to the user on the situation and how the tool 20 could be moved to place the tool 20 back in compliance with the virtual boundary 71. Otherwise, if the manual mode or the semi-autonomous mode were enabled, this could result in abrupt and unexpected movement of the tool 20, particularly when the tool 20 has fallen well out of compliance with the virtual boundary 71. The guidance to the user may be in the form of user feedback, such as visual feedback (on displays 38, visual indicator LEDs on tool 20, etc.), audible feedback (via speakers on manipulator 14, tool 20, etc.), and/or haptic feedback (e.g., by haptically guiding the user to place the tool 20 into a desired relationship with the virtual boundary 71). The collision check can be periodically or continually repeated, and if the tool 20 is returned to being in compliance with the virtual boundary 71, the manual or semi-autonomous modes can be enabled and the user feedback will cease. The control system 60 may automatically switch the manipulator 14 from the boundary-disabled state to the boundary-enabled state upon detecting that the tool 20 has returned to compliance with the virtual boundary 71. In some versions, automated guidance may be provided by the control system 60 to autonomously move the tool 20 to a location in compliance with the virtual boundary 71. In this case, a recovery tool path may be generated by the path generator 68 (or other module) and may be generated based on the current pose of the tool 20 (e.g., from the current pose to a known pose in compliance with the virtual boundary 71), or the recovery path may be predefined.

The system 10 may also operate in a guided-haptic mode, as described in U.S. Provisional Patent Application No. 62/908,056, filed on Sep. 30, 2019, entitled, "Systems and Methods for Guiding Movement of a Tool," which is hereby incorporated herein by reference. The guided-haptic mode may be used to help haptically guide the user into placing the tool 20 at a target state that is in compliance with the virtual boundary 71 in the event, for example, that the tool 20 violates the virtual boundary 71 when in the hold mode and the boundary-disabled state. In the guided-haptic mode, aspects of control used in both the manual mode and the semi-autonomous mode are utilized. For example, forces and torques applied by the user are still detected by the force/torque sensor S to determine the external force $F_{ext}$ that is fed into the virtual simulation to at least partially influence overall movement of the tool 20. Additionally, in the guided-haptic mode, the system 10 generates virtual attractive (or repulsive) forces and torques embodied in a virtual constraint force $F_c$ that is fed, along with the external force $F_{ext}$, into the virtual simulation.

IV. Solving Constraints and Virtual Simulation

Figure 11:
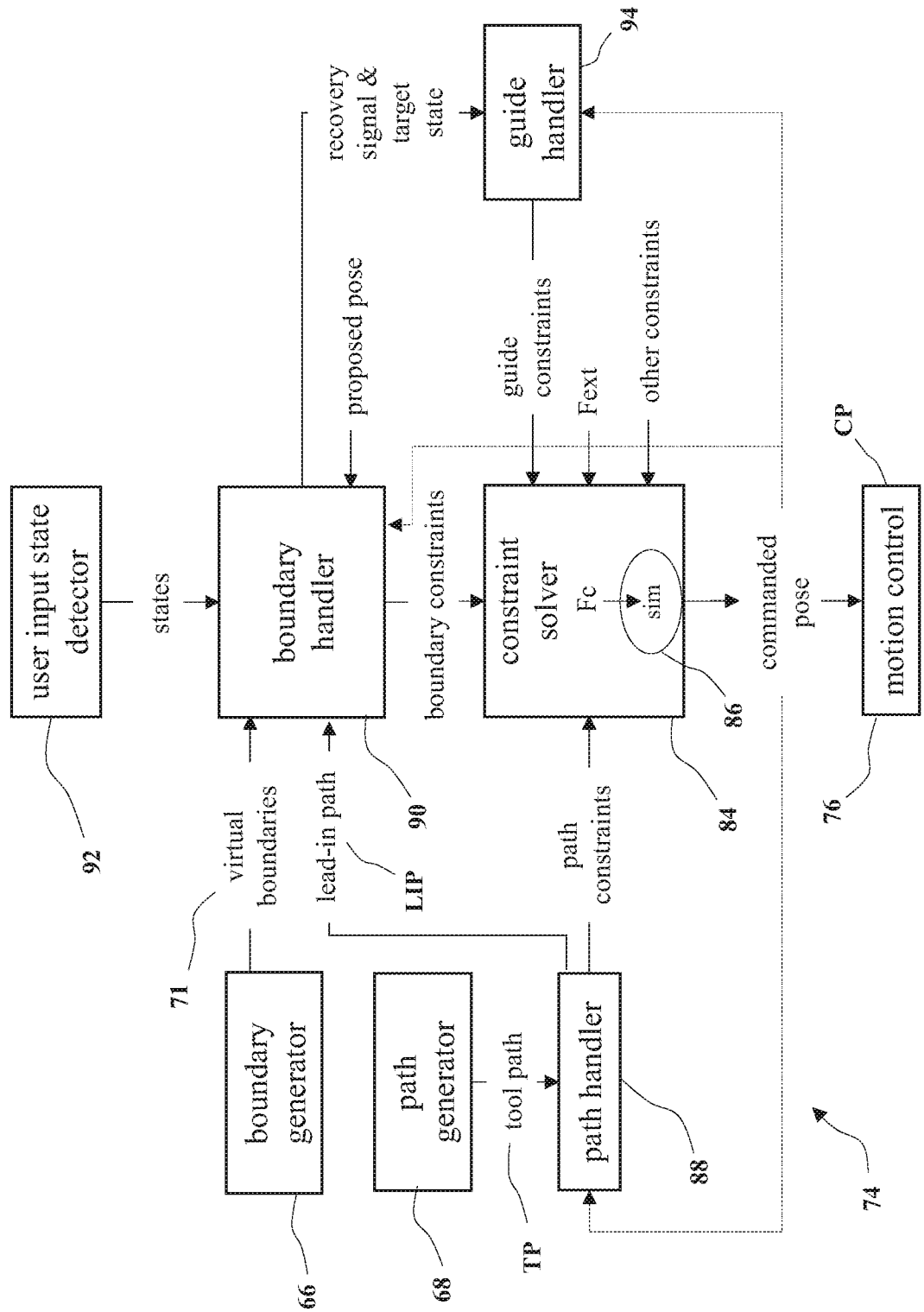
FIG. 11 is a block diagram of modules operable by the control system.

Referring to FIG. 11, one or more virtual constraints, such as path constraints, boundary constraints, guide constraints, and other constraints may be used by the control system 60 in the various modes to control movement of the tool 20. Generally, virtual constraints are restrictions on the motion of rigid bodies that are considered by the control system 60, along with other motion-related information, to determine how to command the manipulator 14 to move the tool 20. These virtual constraints may affect a position of the tool 20 and/or an orientation of the tool 20. As described in more detail below, the control system 60 comprises a constraint solver 84 that operates to calculate the constraint force $F_c$ that satisfies, or attempts to satisfy, the virtual constraints. The constraint force $F_c$ incorporates forces and torques that are defined to affect movement of the tool 20.

The path constraints may be generated based on the tool path TP provided by the path generator 68. Effectively, the path constraints cause virtual forces and/or torques to be calculated by the constraint solver 84 and used in the virtual simulation to pull the tool 20 along the tool path TP so that the TCP of the tool 20 follows along the tool path TP, while the tool 20 keeps a desired orientation. Thus, path constraints can also include orientation constraints, but orientation can also be adjusted based on forces/torques applied by the user. See, for example, the user reorientation methods described in U.S. Pat. No. 9,119,655, incorporated herein by reference. The path constraints may be generated in certain modes of operation, such as in the semi-autonomous mode, but may not be generated in other modes, such as in the manual mode.

The boundary constraints may be defined to inhibit the tool 20 from violating the one or more virtual boundaries 71. Each of the boundary constraints may be considered unidirectional, virtual constraints that operate to maintain the TCP of the tool 20 in compliance with the one or more virtual boundaries 71. For example, the boundary constraints may cause virtual forces and/or torques to be calculated and used in the virtual simulation so that the TCP of the tool 20 has zero velocity (or near zero velocity) at a virtual boundary 71 to prevent the TCP from penetrating (or penetrating too far) into the virtual boundary 71. The boundary constraints may be active in certain modes, such as in the manual mode and the semi-autonomous mode. However, the boundary constraints may be disabled in certain situations, such as when the control system 60 is operating in the boundary-disabled state as previously described. For example, when detecting a collision of the tool 20 with the virtual boundary 71 after moving the anatomy in the hold mode, the manual mode or the semi-autonomous mode are disabled by virtue of the boundary constraints no longer being output to the constraint solver 84.

In some cases, even though the boundary constraints are no longer output, the user is still allowed to move the tool 20 in a free mode or other, similar mode by applying forces and torques to the tool 20. In the free mode, the tool 20 moves relatively freely in response to forces and torques applied to the tool 20 by the user, which can enable the user to move the tool 20 back to compliance with the virtual boundary 71. The external force $F_{ext}$, which includes user applied forces and torques, is an input into the constraint solver 84 and fed into the virtual simulator 86 so that, when enabled, the external force $F_{ext}$ at least partially influences overall movement of the tool 20. The external force $F_{ext}$ is normally enabled, for example, in the manual mode when the tool input 82 is in the first input state (e.g., actuated). The external force $F_{ext}$ can also be enabled in the free mode to respond to user applied forces and torques to allow the user to move the tool 20 back to compliance with the virtual boundary 71. The external force $F_{ext}$ is disabled when the user inputs, e.g., the tool input 82 and the pendant input RC1, are both in the second input state (e.g., neither have been actuated).

The guide constraints are defined to yield the virtual attractive (or repulsive) forces and torques employed in the virtual simulation to guide the user into placing the tool 20 at the target state, in compliance with the virtual boundary 71. The guide constraints are defined to ultimately influence movement of the tool 20 toward the target state so that the user is provided with one or more haptic interaction effects that guide the user into causing desired movement of the tool 20. The guide constraints may be active in certain modes, such as in the guided-haptic mode, but may be inactive in other modes. The guide constraints may also provide other forms of haptic feedback to the user, such as a dampened feel to movement of the tool 20, to indicate an error or abnormal condition, such as when the user is moving the tool 20 further away from the target state.

In some versions, the virtual constraints are velocity impulse constraints in which forces and/or torques are calculated to apply a virtual impulse to an object in the virtual simulation to cause a change in the object's velocity in accordance with desired constraint parameters. In some versions, the constraints are similar to those used in the impulse modeling described in U.S. Pat. No. 9,119,655, incorporated herein by reference. In some versions, virtual constraints are used in all modes.

The virtual constraints that are employed by the control system 60 are defined primarily by three runtime parameters: a constraint Jacobian $J_p$, which maps each virtual constraint to a coordinate system employed for the virtual simulation; a desired velocity $V_{des}$ (or Vp2) which is a scalar velocity of the virtual constraint in the coordinate system (e.g., the desired velocity may be zero when the patient is immobile and the associated virtual constraint defined relative to the patient is not moving, but may be other than zero when the patient moves since the virtual constraint may be tied to the patient); and a constraint distance $\Delta d$, which is how close the TCP, for example, is to the constraint and which dictates whether the virtual constraint is being violated. $\Delta d$ may also be referred to as a penetration depth, i.e., the error distance along the direction of the constraint.

The virtual constraints are not infinitely rigid, but instead each of the virtual constraints has tuning parameters to adjust the stiffness of the virtual constraints, e.g., by incorporating spring and damping parameters into the constraints. Such parameters may include a constraint force mixing parameter (C) and an error reduction parameter (E). The spring and damping parameters may be adjusted during operation. In some versions, values for the tuning parameters may change based on certain relationships, e.g., a curvature of the tool path TP (for path constraints), a relationship between the virtual boundary 71 and the TCP (for boundary constraints), a relationship between the current state and the target state (for guide constraints), etc. The tuning parameters may be different for different virtual constraints. For example, the boundary constraints may be stiffer than the other constraints. The virtual constraints may comprise a first virtual constraint that has a first value for a tuning parameter and a second virtual constraint that has a second value for the tuning parameter, the first value being greater than the second value so that the resulting virtual forces and/or torques embodied in the constraint force $F_c$ are adapted to effect movement of the tool 20 more strongly as a result of the first virtual constraint as compared to the second virtual constraint. The values of the tuning parameters may be greater (e.g., stiffer) for position constraints than for orientation constraints, or vice versa.

The tuning parameters may also be set to: remain constant; rise/fall exponentially with constraint distance; vary linearly with constraint distance; vary with constraint direction; take gravitational effects into account; and the like. The tuning parameters can also be scaled depending on the constraint force $F_c$ that is ultimately computed based on the virtual constraints, such as by increasing/decreasing the stiffness depending on the magnitude of the constraint force $F_c$, or any components thereof. The tuning parameters and their values, their correlation to a particular relationship, and the manner in which they may be scaled, may be stored in one or more look-up tables in any suitable memory in the control system 60 for later retrieval.

Each virtual constraint also has configuration settings. The configuration settings may comprise: information regarding the tuning parameters, such as the constraint force mixing parameter (C) and the error reduction parameter (E);

upper and/or lower force limits; and/or upper and lower constraint distance offsets. The upper and lower force limits refer to limits on the forces computed for each virtual constraint that are ultimately solved by the constraint solver 84 to produce the constraint force $F_e$, as described further below. The virtual constraints may be unidirectional constraints (e.g., the forces computed to satisfy the constraints are positive only or negative only) or bidirectional constraints (e.g., the forces computed to satisfy the constraints may be positive or negative). For unidirectional constraints, the upper force limit can be set high in a positive direction (e.g., +100,000 Newtons) and the lower force limit can be set to zero, but the force limits can be set at any desired limit. For bidirectional constraints, the upper and lower force limits can be set high in opposite directions (e.g., +/−100,000 Newtons). The upper and lower constraint distance offsets dictate when the constraint is active. Some constraints may always be active in certain modes. With respect to the boundary constraints, the upper constraint distance offset may be zero and the lower constraint distance offset may be a large negative value (e.g., −100,000 mm) so that effectively any boundary violation falls within the limits. The upper and lower constraint distance offsets can be set so that the boundary constraint is active when the virtual simulation indicates that a proposed state of the TCP of the tool 20 would violate a virtual boundary 71, as described further below.

The various virtual constraints may be fed into the constraint solver 84, including the guide constraints, the path constraints, the boundary constraints, and other constraints. These constraints may be turned on/off by the control system 60. For example, in some cases, there may be no path constraints (e.g., such as in the manual mode), no boundary constraints (such as in the hold mode, the guided-manual mode, or in the free mode), and no other constraints being generated. Similarly, there may be no guide constraints being generated unless needed to guide the user to place the tool 20 back into compliance with the virtual boundary 71. All of the virtual constraints employed in the behavior control 74 may affect movement of the tool 20.

The constraint solver 84 calculates the constraint force $F_c$ to be virtually applied to the tool 20 in the virtual simulation performed by a virtual simulator 86 based on the virtual constraints fed into the constraint solver 84. The constraint solver 84 is ultimately tasked with providing a solution for the constraint force $F_c$ that satisfies, or attempts to satisfy, all the constraints, and thus other constraints may also influence the magnitude/direction of the constraint force $F_c$. For example, when boundary constraints are actively transmitted to the constraint solver 84, the constraint solver 84 calculates the constraint force $F_c$ to have components of force and/or torque adapted to maintain the tool 20 in compliance with the virtual boundary 71 based on the boundary constraints.

Referring to the constraint equation shown in FIG. 12, the constraint solver 84 places the constraint data for each virtual constraint into a corresponding row of a constraint equation, in matrix form, to solve for $F_p$. Here, $F_p$ is a force vector in the selected coordinate system, i.e., each component of $F_p$ is a scalar constraint force acting in the corresponding constraint direction. In order to solve for $F_p$, as described below, the equation shown in FIG. 12 is converted into a matrix equation where each row represents a single, one-dimensional constraint. The constraint data is placed in the constraint equation, along with other information known by the constraint solver 84, such as the external force $F_{cgext}$, a damping force $F_{damping}$, an inertial force $F_{inertial}$, the virtual mass matrix M, a virtual mass velocity $V_{cg1}$, and the time step $\Delta t$ (e.g., set to $t_{frame}$ of 125 microseconds).

The virtual mass matrix M combines 3×3 mass and inertia matrices. The damping and inertial forces $F_{damping}$ and $F_{inertial}$ are calculated/known by the virtual simulator 86 and are based on the virtual mass velocity $V_{cg1}$ (e.g., the velocity of the virtual mass coordinate system VM) output by the virtual simulator 86 in a prior time step. The virtual mass velocity $V_{cg1}$ is a 6-DOF velocity vector comprising linear and angular velocity components. The damping force $F_{damping}$ is a 6-DOF force/torque vector computed as a function of the virtual mass velocity $V_{cg1}$ and a damping coefficient matrix (linear and rotational coefficients may not be equal). Damping is applied to the virtual mass to improve its stability. The inertial force $F_{inertial}$ is also a 6-DOF force/torque vector computed as a function of the virtual mass velocity $V_{cg1}$ and the virtual mass matrix M. The damping and inertial forces, $F_{damping}$ and $F_{inertial}$, can be determined in the manner described in U.S. Pat. No. 9,566,122 to Bowling et al., hereby incorporated herein by reference.

The constraint solver 84 may be configured with any suitable algorithmic instructions (e.g., an iterative constraint solver, Projected Gauss-Seidel solver, etc.) to solve this system of constraint equations in order to provide a solution satisfying the system of equations (e.g., satisfying the various constraints). In some cases, all constraints may not simultaneously be met. For example, in the case where motion is overconstrained by the various constraints, the constraint solver 84 will essentially find a 'best fit' solution given the relative stiffness/damping of the various constraints. The constraint solver 84 solves the system of equations and ultimately outputs the constraint force $F_p$.

When a Projected Gauss-Seidel solver is employed, the constraint solver 84 constructs A and b matrices based on the constraints, uses Projected Gauss-Seidel to solve the system of equations to determine the resulting force vector $F_p$, takes the output of Projected Gauss-Seidel and transforms it from the selected coordinate system (e.g., the constraint coordinate system) to the virtual mass coordinate system VM. For example, using the equation $F_c = J_p^T F_p$, wherein $F_c$ is the constraint force, the components of force vector $F_p$ are converted to an equivalent force/torque vector $F_c$ applied to the virtual mass coordinate system VM.

Methods of using Project Gauss-Seidel to solve a system of equations for multiple constraints is shown, for example, in "Constraint based physics solver" by Marijn Tamis and Giuseppe Maggiore, dated Jun. 15, 2015 (v1.02), which can be found at http://www.mft-spirit.nl/files/MTamis_ConstraintBasedPhysicsSolver.pdf, or in "Comparison between Projected Gauss-Seidel and Sequential Impulse Solvers for Real-Time Physics Simulations," by Marijn Tamis, dated Jul. 1, 2015 (v1.01), which can be found at http://www.mft-spirit.nl/files/MTamis_PGS_SI_Comparison.pdf, both of which are hereby incorporated herein by reference in their entirety.

The Projected Gauss-Seidel method addresses Linear Complementarity Problems (LCP). Inequality associated with LCP arises since some constraint types (e.g., one-sided constraints, such as the boundary constraints) can only push (apply force) in one direction. If the calculated force for such a constraint is outside its allowed range for a given iteration of the constraint solver 84, which is invalid, the given constraint must be pruned (or alternately limited/capped at its upper or lower allowed value) and the remaining constraints solved, until a suitable result (i.e., convergence) is found. In this manner, the constraint solver 84 determines the active set of constraints for a given time step, and then solves for their values. Other constraint types can apply forces in both positive and negative directions, e.g., two-sided constraints. Such constraints include the guide constraints used to guide the user into moving the tool toward the target state. Such two-sided constraints, when enabled, are usually active and not pruned/limited during the constraint solver 84 iterations.

The constraint force $F_c$ calculated by the constraint solver 84 comprises three components of force along x, y, z axes and three components of torque about the x, y, z axes. The virtual simulator 86 utilizes the constraint force $F_c$, along with the external force $F_{cgext}$, the damping force $F_{damping}$, and the inertial force $F_{inertial}$ (all of which may comprise six components of force/torque), in its virtual simulation. In some cases, these components of force/torque are first transformed into a common coordinate system (e.g., the virtual mass coordinate system VM) and then summed to define a total force $F_T$. The resulting 6-DOF force (i.e., force and torque) is applied to the virtual rigid body and the resulting motion is calculated by the virtual simulator 86. The virtual simulator 86 thus acts to effectively simulate how the various constraints, all of which are reflected in the total force $F_T$, affects motion of the virtual rigid body. The virtual simulator 86 performs forward dynamics to calculate the resulting 6-DOF pose and velocity of the virtual rigid body based on the given total force $F_T$ being applied to the virtual rigid body. In one example, the virtual simulator 86 comprises a physics engine, which is executable software stored in a non-transitory memory of any one or more of the aforementioned controllers 21, 26, 36 and implemented by the control system 60.

For the virtual simulation, the virtual simulator 86 models the tool 20 as the virtual rigid body in the virtual mass coordinate system VM typically with the origin of the virtual mass coordinate system VM being located at the center of mass of the virtual rigid body, and with the coordinate axes being aligned with the principal axes of the virtual rigid body. The virtual rigid body is a dynamic object and a rigid body representation of the tool 20 for purposes of the virtual simulation. The virtual rigid body is free to move according to six degrees of freedom (6-DOF) in Cartesian space according to the virtual simulation. The virtual simulation may be processed computationally without visual or graphical representations. Thus, it is not required that the virtual simulation display dynamics of the virtual rigid body. In other words, the virtual rigid body need not be modeled within a graphics application executed on a processing unit. The virtual rigid body may exist only for the virtual simulation.

The virtual rigid body and its properties (mass, inertia matrix, center of mass, principal axes, etc.) define how the tool 20 will move in response to applied forces and torques (e.g., from the total force $F_T$, which incorporates forces and torques applied by the user and constraint forces and torques). It governs whether the tool 20 will feel heavy or light and how it will move (e.g., accelerate in translation and rotation) in response to applied forces and torques. By adjusting the properties of the virtual rigid body, the control system 60 can adjust how the tool 20 feels to the user. It may be desirable to have the properties of the virtual rigid body modeled to be reasonably close to the actual properties of the tool 20, for as realistic motion/feel as possible, but that is not required. For control stability reasons (given the finite acceleration of the manipulator 14, control latencies, etc.), the virtual mass and inertia may be modeled to be somewhat higher than that of the physical tool 20.

The virtual rigid body may correspond to components, which may be on or within the tool 20. Additionally or alternatively, the virtual rigid body may extend, in part, beyond the physical tool 20. The virtual rigid body may take into account the tool 20 with the energy applicator 24 or may take into account the tool 20 without the energy applicator 24. Furthermore, the virtual rigid body may be based on the TCP. In one example, the center of mass of the virtual rigid body is understood to be the point around which the virtual rigid body would rotate if a virtual force is applied to another point of the virtual rigid body and the virtual rigid body were otherwise unconstrained, i.e., not constrained by the manipulator 14. The center of mass of the virtual rigid body may be close to, but need not be the same as, the actual center of mass of the tool 20. The center of mass of the virtual rigid body can be determined empirically. Once the tool 20 is attached to the manipulator 14, the position of the center of mass can be reset to accommodate the preferences of the individual practitioners.

The virtual simulator 86 effectively simulates rigid body dynamics of the tool 20 by virtually applying forces and/or torques on the virtual rigid body in the virtual simulation, i.e., by virtually applying the components of force and torque from the total force $F_T$ on the center of mass of the virtual rigid body in the virtual mass coordinate system VM. Thus, the forces/torques virtually applied to the virtual rigid body may comprise forces/torques associated with the external force $F_{cgext}$ (e.g., which is based on input from the one or more sensors), the damping force $F_{damping}$, the inertial force $F_{inertial}$, and the forces/torques from the constraint force $F_c$ associated with the various constraints (by virtue of being embodied in the constraint force $F_c$).

Rigid body Jacobians can be used to transform velocities and forces from one coordinate system (reference frame) to another on the same virtual rigid body and may be employed here to transform the forces and torques of $F_{ext}$ to the virtual mass coordinate system VM as well (e.g., to yield $F_{cgext}$ used in the constraint equation). The virtual simulator 86 then internally calculates the damping force $F_{damping}$ and the inertial force $F_{inertial}$ to determine the total force $F_T$, and also to output the damping force $F_{damping}$ and the inertial force $F_{inertial}$ for use by the constraint solver 84 in its system of equations in the next time step.

Figure 14:
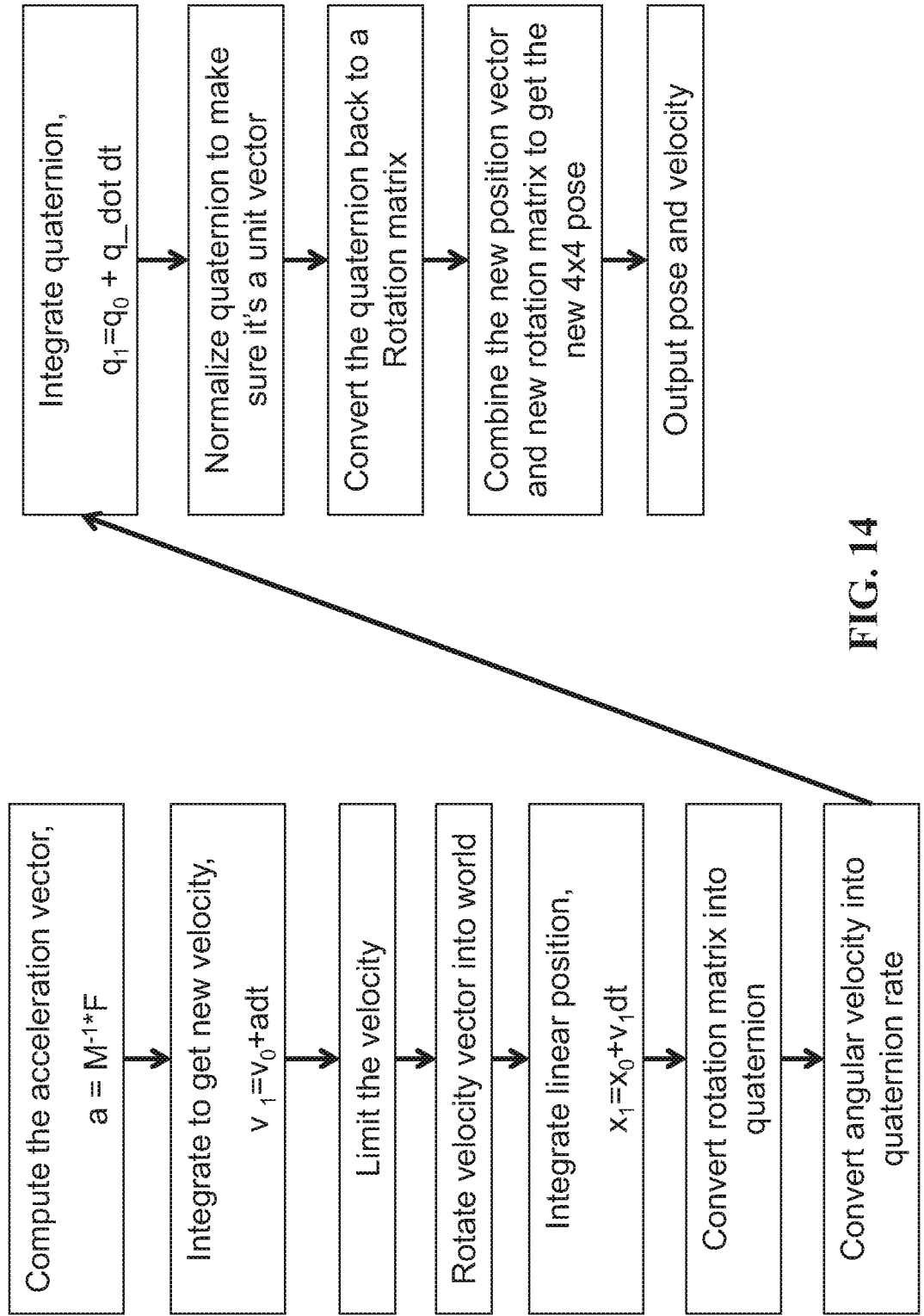

A virtual forward dynamics algorithm, as shown in FIGS. 13 and 14, may be employed in the virtual simulation to simulate the motion of the virtual rigid body as it would move upon application of the total force $F_T$. Effectively, the virtual forward dynamics algorithm solves the equation F=ma (or a=F/m) in 6-DOF and integrates the acceleration to yield velocity, which is then used to determine a new pose, as shown in FIG. 14. The control system 60 inputs the virtual forces and/or torques (e.g., the total force $F_T$) into the virtual simulator 86 and these virtual forces and/or torques are applied to the virtual rigid body at the center of mass (e.g., the CG) in the virtual simulation when the virtual rigid body is in the initial pose with the initial velocity. The virtual rigid body is moved to a final pose having a different state (i.e., position and/or orientation) and with a final velocity within Cartesian space in response to the control system 60 satisfying the inputted virtual forces and/or torques. The next commanded pose to be sent to the motion control 76 is based on the final pose calculated by the virtual simulator 86. Thus, the virtual simulator 86 operates to determine the next commanded pose by simulating the effects of applying the total force $F_T$ on the virtual rigid body using virtual forward dynamics as shown in FIG. 14.

Velocity limits may be imposed on the virtual rigid body in the simulation. In some cases, the velocity limits may be set high so that they generally don't affect the simulation, or they may be set at any desired value. The virtual rigid body is in an initial pose (initial state) and has an initial velocity at commencement of each iteration of the virtual simulation (e.g., at each time step/interval dt). The initial pose and initial velocity may be defined as the final pose and the final velocity output by the virtual simulator 86 in the previous time step. Thereafter, the virtual simulator 86 calculates and outputs the next commanded pose based on its virtual simulation. The control system 60 is configured to command the manipulator 14 to move the tool 20 based on the commanded pose.

Referring back to FIG. 11, a block diagram shows processes carried out to control operation of the manipulator 14 and movement of the tool 20 using the constraints previously described. In the version shown, the behavior control 74 comprises a path handler 88. The path handler 88 operates to generate/output the path constraints in accordance with the tool path TP provided by the path generator 68. The tool path TP is an input into the path handler 88. The path handler 88 generates the path constraints based on the constraint parameters previously described, including determining the constraint runtime parameters (e.g., the constraint Jacobian $J_p$, the desired velocity $V_{des}$ (or Vp2), and the constraint distance $\Delta d$). The path handler 88, in the version described with reference to FIG. 11, is enabled and active in the semi-autonomous mode, but disabled in the other modes.

The behavior control 74 further comprises a boundary handler 90 to generate the boundary constraints based on the one or more virtual boundaries 71 generated by the boundary generator 66. The boundary constraints ultimately allow the control system 60 to control operation of the manipulator 14 and movement of the tool 20 based on a relationship between the tool 20 and the one or more virtual boundaries 71 associated with the target site. For example, the control system 60 limits relative movement between the tool 20 and a virtual boundary 71 via the boundary constraints. Inputs into the boundary handler 90 include the last commanded pose of the tool 20 (e.g., treated as the current pose), the virtual boundary 71, and the user input states of the tool input 82 and the pendant input RC1. The boundary handler 90 generates the boundary constraints based on the constraint parameters previously described, including determining the constraint runtime parameters (e.g., the constraint Jacobian $J_p$, the desired velocity $V_{des}$ (or Vp2), and the constraint distance $\Delta d$).

The behavior control 74 also comprises a guide handler 94. In certain situations, it may be desirable to guide the user into manipulating the tool 20 in a manner that guides the tool 20 to a desired position and/or orientation. For example, in some situations, the TCP of the tool 20 may be in a position in which it violates the virtual boundary 71. In this case, certain modes of operation, such as the manual mode or the semi-autonomous mode, may be disabled (e.g., no boundary constraints or path constraints are generated to influence movement of the tool 20) until the TCP of the tool 20 complies with the virtual boundary 71. The guide handler 94 may obtain a target state for the tool 20 that puts the tool 20 in compliance with the virtual boundary 71 and generate one or more guide constraints based on the target state and a current state of the tool 20. As previously mentioned, the user may also be able to move the tool 20 back to compliance with the virtual boundary 71 in the free mode, i.e., without generating any guide constraints, or the control system 60 may automatically move the tool 20 back to compliance with the virtual boundary 71 via a recovery path. Other ways of achieving compliance with the virtual boundary 71 are also contemplated, as described further below.

Input into the guide handler 94 comprises a recovery signal and the last commanded pose (current state). A target state (e.g., pose) may be part of the recovery signal from the boundary handler 90, as the boundary handler 90 may identify a target position and/or orientation of the tool 20 that is not in violation of the virtual boundary 71. The target state may be defined in the anatomical coordinate system, anatomy tracker coordinate system, or the like, and transformed to a common coordinate system with the last commanded pose. The guide handler 94 defines the one or more guide constraints based on the relationship between the last commanded pose and the target state. The guide constraints are output from the guide handler 94 into the constraint solver 84. The guide handler 94 is configured to activate the guide constraints to provide haptic feedback to the user to guide the user into placing the tool 20 into compliance with the virtual boundary 71, the constraint solver 84 being configured to calculate the constraint force $F_c$ adapted to attract the tool 20 into compliance with the virtual boundary 71 based on the guide constraints.

V. Collision Checks and Boundary-Enabled and Boundary-Disabled States

The boundary handler 90 performs various collision checks depending on the mode of operation, user input state, etc. A first type of collision check involves checking whether/how a current state (e.g., current pose) of the tool 20 or a proposed state (e.g., proposed pose) of the tool 20 generated in the virtual simulation by the virtual simulator 86 violates the virtual boundary 71. This collision check is performed to determine the boundary constraints that need to be generated by the boundary handler 90 and applied by the constraint solver 84 so that the current state/proposed state is altered in a way to prevent, or at least to limit, the violation of the virtual boundary 71 by the tool 20 during normal operation in the manual mode or the semi-autonomous mode. In some versions, this type of collision check is performed in each frame during operation in the manual mode or the semi-autonomous mode and occurs before the generation of a new commanded pose by the virtual simulator 86 so that the commanded pose that is ultimately generated and carried out by the motion control 76 limits violations of the virtual boundary 71 by the tool 20. In some versions, this type of collision check could be performed by the boundary handler 90 based on the commanded pose computed in the prior iteration (e.g., the commanded pose of the prior time frame is set as the current pose). In that case, the boundary handler 90 determines boundary constraints that need to be generated to at least limit violation of the virtual boundary 71. For example, the commanded pose from the prior frame may be one that results in the tool 20 being moved slightly across the virtual boundary 71, but the boundary handler 90 generates boundary constraints in the current frame to bring the tool 20 back.

A method for performing the first type of collision check is described in U.S. Patent Application Pub. No. 2018/0353253 to Bowling, entitled, "Robotic Surgical System And Method For Producing Reactive Forces To Implement Virtual Boundaries," which is hereby incorporated herein by reference. Other collision detection methods may also be employed. For instance, if the virtual boundary 71 is defined by a triangle mesh, then collision detection using broad phase and narrow phase searches may be conducted as described in U.S. Pat. No. 9,119,655, incorporated herein by reference.

The boundary handler 90 performs a second type of collision check when the tool input 82 or the pendant input RC1 switches to the first input state from the second input state, e.g., when the system 10 is being switched from the hold mode to the manual mode, or from the hold mode to the semi-autonomous mode. The current state of the user inputs and switching thereof can be detected by a user input state detector 92. The user input state detector 92 feeds the current state of the user inputs (e.g., the tool input 82 and the pendant input RC1) and indicates any state changes thereof to the boundary handler 90. The second type of collision check may be a subroutine performed each time any of the user inputs switch from one state to another state.

To perform the second type of collision check, the boundary handler 90 checks the geometric definition of the virtual boundary 71 against the current state of the tool 20 (e.g., the last commanded pose) to check whether the tool (e.g., the TCP of the tool 20) is in compliance with the virtual boundary 71 or in violation of the virtual boundary 71. As previously noted, a predefined, configurable tolerance may be established for the virtual boundary 71 such that some penetrations of the tool 20 into the virtual boundary 71 or deviations of the tool 20 from perfect compliance with the virtual boundary 71 are not considered violations of the virtual boundary 71, so the second type of collision check would need to take these tolerances into account as well. This may simply require checking a bounded volume of the virtual boundary 71 and comparing the current position of the TCP of the tool 20 to the bounded volume. In some versions, positions of one or more virtual, stereotactic interaction features SIFs attributed to the tool 20, in addition to the TCP, may be compared to the bounded volume. These stereotactic interaction features SIFs may be points corresponding to actual points on the tool 20, spheres with unique origins and radii, or other suitable geometric shapes. Each of the stereotactic interaction features SIFs is compared to the bounded volume to check for collisions. The bounded volume may, for example, be defined by voxels and the boundary handler 90 could perform collision detection to determine if the tool 20 falls within any of the voxels. Other methods of collision detection may utilize ray-tracing methods, configuration space searches, bounding volume hierarchies, point-membership classification (PMC), etc. The boundary handler 90 may detect a collision of the tool 20 with the virtual boundary 71 using any suitable method.

If the second type of collision check indicates that the tool 20 is in violation of the virtual boundary 71, then a recovery mode is enabled and a recovery signal and associated target state is sent to the guide handler 94 that can then generate the user feedback previously described to guide the user into placing the tool 20 into compliance with the virtual boundary 71. While the tool 20 is in violation of the virtual boundary 71, the desired operational mode of the manipulator 14 (e.g., the manual mode or the semi-autonomous mode) may be disabled. Autonomous, boundary-complying movement of the tool 20 remains disabled in the recovery mode when the user input (e.g., the tool input 82 or the pendant input RC1) are in the first input state.

If the collision check indicates that the tool 20 is already in compliance with the virtual boundary 71, then the desired mode of operation of the manipulator 14 can be enabled. If the collision check passes (e.g., the TCP and/or other SIFs are fully in an allowed region of the virtual boundary 71, or not penetrating the virtual boundary 71 more than a configured distance (e.g., 0.1 mm)), then the boundary constraints are activated and movement of the tool 20 is enabled. The second type of collision check and activation of the boundary constraints is done atomically (in the same time step), to avoid race conditions of movement between the check and activation.

If the second type of collision check fails, the boundary constraints are not enabled and a recovery sequence is initiated via the recovery mode. The recovery sequence may comprise a user message being displayed on one or more of the displays 38 requesting the user to move the tool 20 away from a resection area. The tool drive is also disabled (e.g., no machining is allowed). In some versions, in the recovery mode, high damping movement may be enabled (e.g., damping constraints may be employed by the guide handler 94 to provide highly damped movement of the tool 20). Damping coefficients used in the virtual simulation carried out by the virtual simulator 86 may also be adjusted to change the damping force $F_{damping}$ to cause increased damping. Such movement may be enabled by allowing the manipulator 14 to respond to user forces and torques applied to the tool 20, but in a relatively dampened manner. The high damping movement allows the user to immediately feel through haptic interaction (via the damping constraints), that an abnormal condition is present if the user is not directly watching the displays 38 at the time.

The recovery mode may cause activation of the guided-haptic mode to help guide the user during recovery. Alternatively, the free mode may be activated in the recovery mode to allow the user to freely move the tool 20 into compliance with the virtual boundary 71. A recovery path, as previously noted, may additionally, or alternatively, be generated in the recovery mode and used to autonomously move the tool 20 back into compliance with the virtual boundary 71. In this case, the pendant input RC1 could be used to control movement of the tool 20 along the recovery path. In some versions, in the recovery mode, the boundary handler 90 or the guide handler 94 may generate recovery constraints associated with the virtual boundary 71 that have tuning parameters lower than the tuning parameters of the original boundary constraints such that the tool 20 can more gradually recover from being in violation of the virtual boundary 71 (i.e., the virtual boundary 71 is effectively altered to be less stiff). In some versions, in the recovery mode, the control system 60 may move the virtual boundary 71 (e.g., change its position/orientation) from its starting location such that the tool 20 is no longer in violation of the virtual boundary 71. Once the tool 20 is back in compliance with the virtual boundary 71, then autonomous, boundary-complying movement of the tool 20 may be enabled by the control system 60 and the virtual boundary 71 then slowly transitioned back to its starting location while gently pushing the tool 20 along with it such that the tool 20 remains in compliance with the virtual boundary 71.

The steps performed in the recovery mode are carried out relatively quickly, so that there is no noticeable delay in commencement of tool motion in response to the user's original activation of the tool input 82 or the pendant input RC1. For instance, this allows the user/manipulator 14 to move the tool 20 back to an allowed region relative to the virtual boundary 71 relatively efficiently. While the tool 20 moves in the recovery mode, the control system 60 periodically or continually performs the second type of collision check, to detect when the tool 20 returns to compliance with the virtual boundary 71. At that point, without requiring the user to release the tool input 82 or the pendant input RC1, the previously described activation of the boundary constraints is performed, the damping (if employed) is reverted to its normal setting (providing an indication, based on user feel, that the condition is resolved), the ability to use the tool drive and operate the tool 20 is enabled, and the message on the displays 38 is updated/cleared.

The recovery sequence may also be initiated for cases in which one of the trackers is not valid (i.e., not visible or below a quality threshold) during activation. Once the trackers are visible and the second type of collision check is clear, then the control system 60 switches to the boundary-enabled state to allow operation in the manual mode or the semi-autonomous mode.

Figure 15:
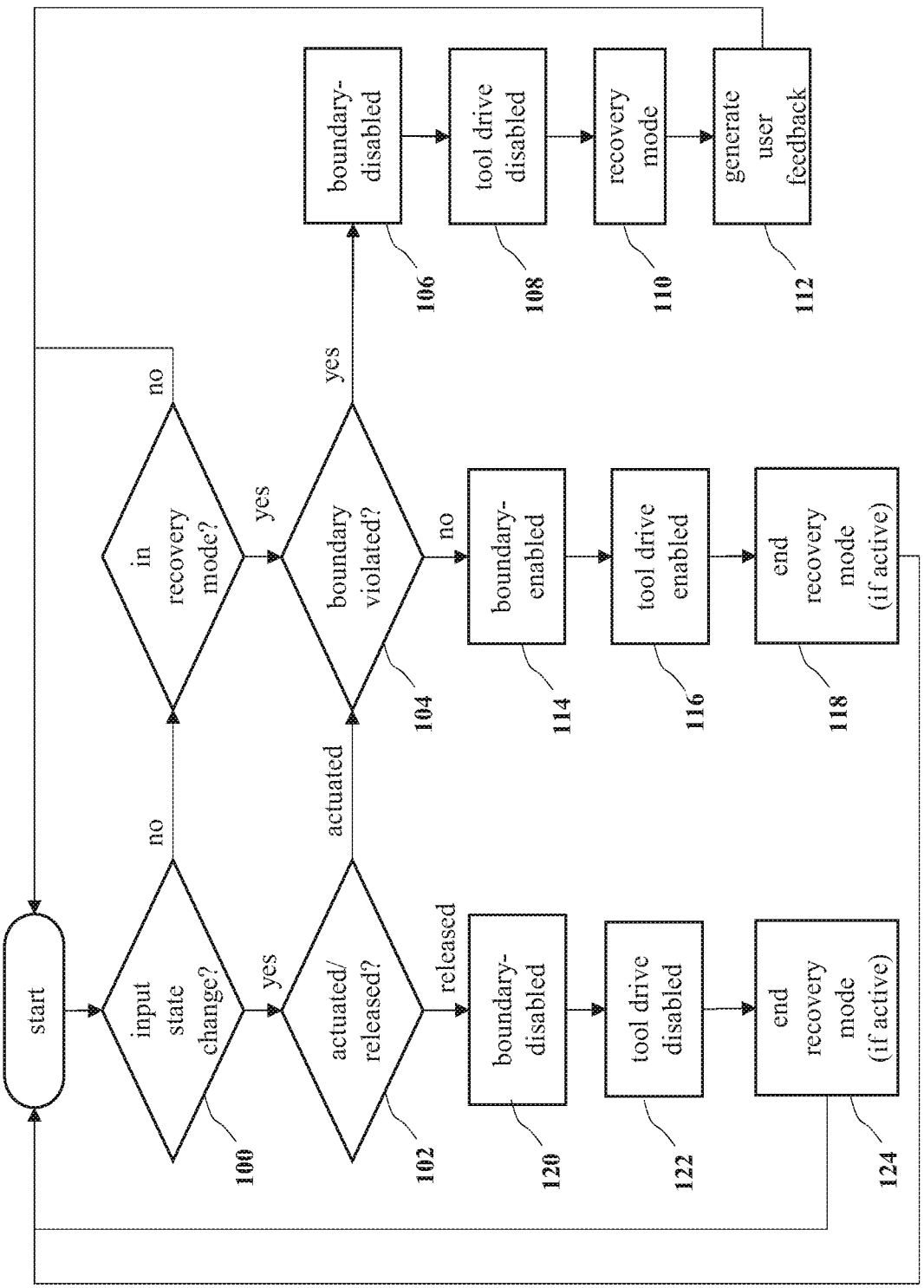
FIG. 15 shows an example set of steps carried out by the control system to switch between boundary-enabled and boundary-disabled modes.

FIG. 15 illustrates a subroutine performed by the boundary handler 90 and associated components to perform the second type of collision check. In step 100, the boundary handler 90 determines whether there has been an input state change, i.e., has the tool input 82 or the pendant input RC1 switched from one state to another. If not, and if the boundary handler 90 is not already in the recovery mode, then the boundary handler 90 returns to checking for state changes. If there has been a state change, the boundary handler 90 then determines in step 102 the nature of the state change, i.e., is it a change/transition from the second input state to the first input state (e.g., a user input has been actuated), or vice versa (e.g., released). If the tool input 82 or the pendant input RC1 have been actuated, then the boundary handler 90 performs the collision check in step 104 to determine whether the tool 20 is in compliance with the virtual boundary 71 or is in violation of the virtual boundary 71.

If the virtual boundary 71 is violated, then: (i) the control system 60 is switched to the boundary-disabled state in step 106; (ii) the tool drive that controls operation of the tool 20 is disabled in step 108 meaning that the control system 60 effectively ignores any input from the user normally associated with operation of the tool 20; and (iii) the recovery mode is initiated in step 110. It should be noted that these steps may occur nearly simultaneous and the order presented in FIG. 15 is merely for illustration purposes. In step 112, the guide handler 94 is instructed via the recovery signal, to generate user feedback to inform the user that the virtual boundary 71 is violated and/or to guide the user into placing the tool 20 into compliance with the virtual boundary 71. Once in the recovery mode, the subroutine continues to check for any later state changes, and if there is no state change (e.g., user is still actuating the tool input 82 or the pendant input RC1), the boundary handler 90 continues in the recovery mode to check if the tool 20 remains in violation of the virtual boundary 71.

If the virtual boundary 71 is not violated, then: (i) the control system 60 is switched to the boundary-enabled state in step 114; (ii) the tool drive that controls operation of the tool 20 is enabled in step 116; and (iii) the recovery mode (if active) is ended in step 118. Although not shown, the manual mode or the semi-autonomous mode selected by the user is enabled when the recovery mode ends. It should be noted that these steps may occur nearly simultaneous and the order presented in FIG. 15 is merely for illustration purposes. It should also be noted that when the tool drive is enabled in step 116, after being in the recovery mode, the tool 20 may not be immediately activated, but tool control returns to the user to allow tool operation via the associated user interface UI (e.g., via button, footswitch, trigger, etc.). In cases where the recovery mode ended while the user was actuating an input of the user interface UI to cause tool operation (e.g., motorized cutting, etc.), the control system 60 may ignore this input until the user releases the input and re-engages it so that there is no unexpected operation of the tool 20 after leaving the recovery mode.

If the tool input 82 or the pendant input RC1 have been released, then: (i) the control system 60 is switched to the hold mode and the boundary-disabled state in step 120; (ii) the tool drive that controls operation of the tool 20 is disabled in step 122; and (iii) the recovery mode (if active) is ended in step 124. It should be noted that these steps may occur nearly simultaneous and the order presented in FIG. 15 is merely for illustration purposes.

In some versions, the control system 60 may be configured to disable autonomous, boundary-complying movement of the tool 20 after a predetermined time period elapses following a transition of the user input from the first input state to the second input state. For instance, it may be desirable to leave the virtual boundary 71 enabled for a short time period (e.g., 100-500 ms) after the tool input 82 or the pendant input RC1 is released, to allow time for the manipulator 14/tool 20 to come to a stop. Otherwise, if the boundary constraints are disabled immediately, the tool 20 may coast through the virtual boundary 71 and cut or move in undesired ways. In some cases, when the tool input 82 or the pendant input RC1 is released, the control system 60 may switch to highly dampened movement as previously described so that the tool 20 more quickly comes to a stop. After a fixed time interval, or once the tool 20 comes to a stop, then the virtual boundary 71 can be disabled. This delay can be predetermined/preconfigured as noted, or it could also be controlled automatically by the control system 60 by monitoring the tool 20 (e.g., the virtual rigid body) and its velocity (linear, rotational) and keeping the boundary constraints enabled until the magnitude of the velocity (linear, rotational) is below a certain threshold (or below a set of thresholds defined for each degree of freedom and/or each type of velocity). In some cases, the virtual boundary 71 may remain active until the one or more velocities fall below the one or more thresholds or a maximum time is reached, whichever comes first.

The process outlined in FIG. 15 illustrates how the boundary handler 90 is operable between the boundary-enabled state in which the boundary constraints are being transmitted from the boundary handler 90 to the constraint solver 84 and the boundary-disabled state in which boundary constraints are no longer being transmitted from the boundary handler 90 to the constraint solver 84 to thereby disable autonomous, boundary-complying movement of the tool 20. The boundary handler 90: (i) operates in the boundary-disabled state in response to the tool input 82 or the pendant input RC1 transitioning from the first input state to the second input state, with a possible delay in the transition to the boundary-disabled state after the tool input 82 or the pendant input RC1 are switched to allow movement of the manipulator 14 to settle; (ii) operates in the boundary-enabled state in response to the tool input 82 or the pendant input RC1 transitioning from the second input state to the first input state so long as the tool 20 is in compliance with the virtual boundary 71; (iii) operates in the boundary-disabled state in response to the tool input 82 or the pendant input RC1 transitioning from the second input state to the first input state if the tool 20 is in violation of the virtual boundary 71 at the time of transition, or shortly thereafter; and (iv) switches from the boundary-disabled state to the boundary-enabled state once the tool 20 is placed into compliance with the virtual boundary 71 if the tool input 82 or the pendant input RC1 are still in the first input state.

The constraint solver 84, virtual simulator 86, path handler 88, boundary handler 90, user input state detector 92, and guide handler 94 each comprise executable software stored in a non-transitory memory of any one or more of the aforementioned controllers and implemented by the control system 60. The constraint solver 84, virtual simulator 86, path handler 88, boundary handler 90, user input state detector 92, and guide handler 94 may be embodied in one or more software modules stored in any suitable location for implementation by the control system 60.

VI. Behavior Control

Figure 16:
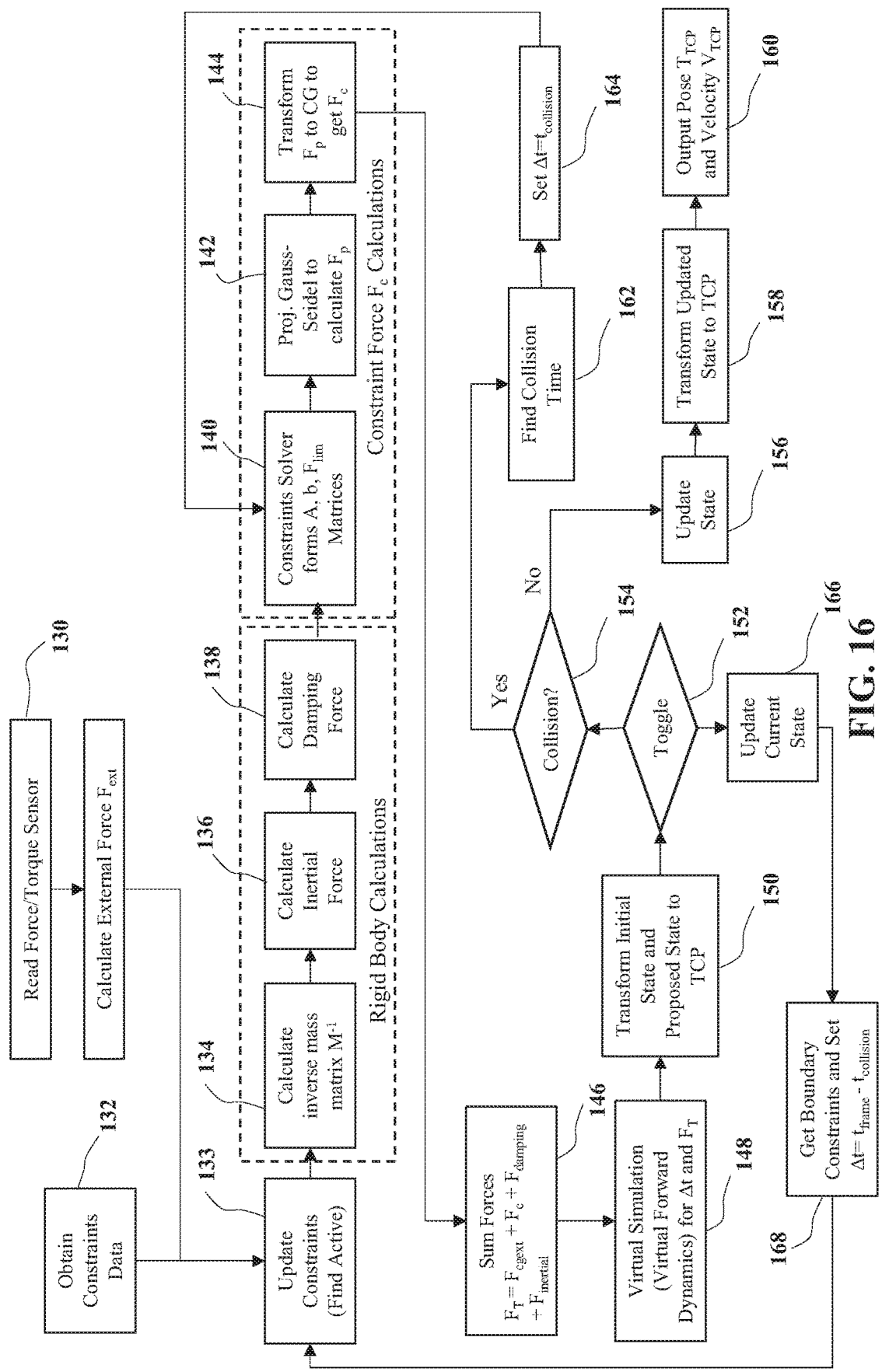
FIG. 16 shows an example set of steps carried out by the control system to solve constraints, perform forward dynamics, and determine a commanded pose.

FIG. 16 summarizes various steps carried out by the behavior control 74. These include steps performed by the constraint solver 84, the virtual simulator 86, the path handler 88, the boundary handler 90, and the guide handler 94, as described above. In step 130, the external force $F_{ext}$ is calculated based on readings taken from the force/torque sensor S. In steps 132 and 133, constraints data associated with the various virtual constraints are obtained and active constraints are identified. In step 133, constraints, such as the boundary constraints may be updated depending on the outcome of the virtual simulation, as described further below. FIG. 16 represents embodiments in which a proposed state output by the virtual simulation is evaluated for collisions before a final, updated state is calculated, but in some versions, the output from the virtual simulation is set as the final, updated state without checking for further collisions (see FIG. 16A described further below).

In steps 134-138, rigid body calculations are carried out by the virtual simulator 86 to determine the inverse mass matrix $M^{-1}$, the inertial force $F_{inertial}$, and the damping force $F_{damping}$ of the virtual rigid body. In steps 140-144, the constraint solver 84 utilizes the output from the rigid body calculations performed in steps 134-138 and the constraints data provided in steps 132 and 133 to perform the constraint force calculations previously described to ultimately yield the constraint force $F_c$. In step 146, the constraint force $F_c$ is summed with the external force $F_{ext}$ transformed to the virtual mass coordinate system VM ($F_{cgext}$), the damping force $F_{damping}$, and the inertial force $F_{inertial}$ to yield the total force $F_T$. In step 148, the total force $F_T$ is applied to the virtual rigid body in the virtual simulation conducted by the virtual simulator 86 to determine a proposed state (e.g., pose and velocity) of the virtual rigid body, and ultimately to transform the initial state and the proposed state to the TCP in step 150.

In step 152, a software toggle is employed that initially follows one path, and then in the next execution, follows the other path. In the first path, the boundary handler 90 performs the first type of collision check in step 154 to determine whether the proposed state would result in a collision with the virtual boundary 71. If no collision is detected, then the proposed state is verified and saved as the updated state in step 156 and transformed to the TCP in step 158. The new commanded pose ($T_{TCP}$), and velocity ($V_{TCP}$) are output by the virtual simulator 86 in step 160. If no collision detected, then the toggle (step 152) remains in its current state, i.e., the toggle is not switched to follow the other path.

Figure 17A:
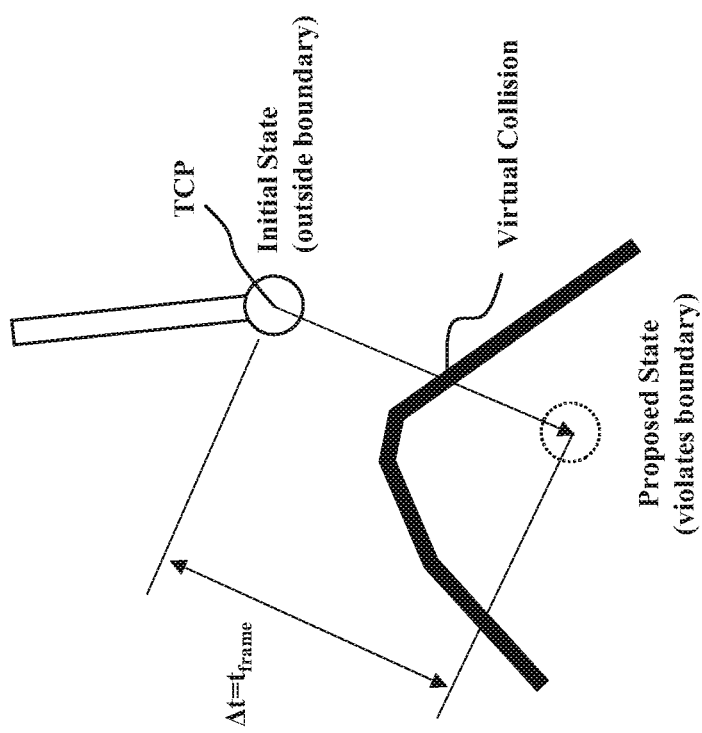
FIGS. 17A-17D illustrate how the control system accounts for collisions when determining the commanded pose.
Figure 17B:
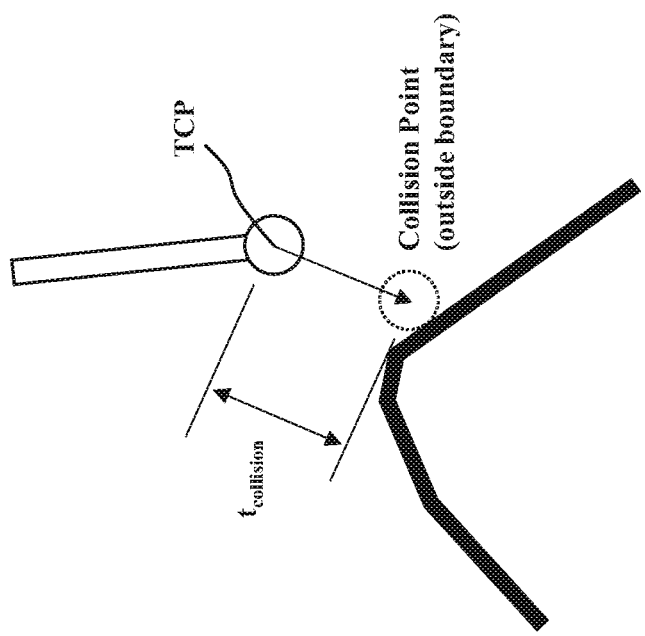
Figure 17C:
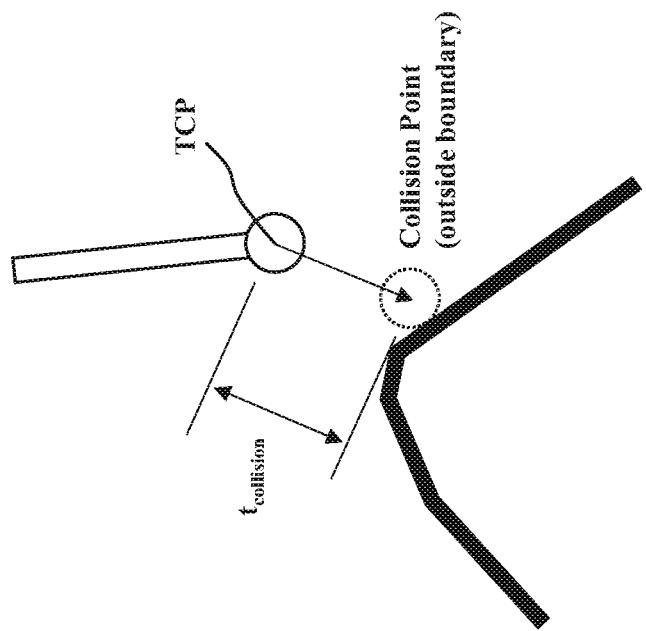

If there is a collision detected, then the boundary handler 90 calculates the collision time $t_{collision}$ in step 162 and the toggle is switched. Referring to FIGS. 17A and 17B, the collision time $t_{collision}$ can be determined by calculating a first distance between the current state and the proposed state calculated in the virtual simulation (FIG. 17A), calculating a second distance between the current state and the virtual boundary 71 (FIG. 17B) and multiplying the ratio of the second distance over the first distance by the overall time frame $t_{frame}$. So, for example, if the virtual boundary 71 is crossed at 50% of the distance to the proposed state, then the collision time $t_{collision}$ is 50% of the time frame $t_{frame}$. The time $\Delta t$ used for the constraint force calculations in steps 140-144 is then reset to the collision time $t_{collision}$ in step 164 (also see FIG. 17C) and a new proposed state is calculated. Accordingly, the virtual simulation is trimmed to the time before the collision occurs. The virtual simulation then determines a new proposed state. Once the new proposed state is determined, the toggle (step 152) causes the other path to be followed (since a collision was detected), and the new proposed state becomes the updated current state in step 166. The toggle is automatically reset to follow the first path once the transition to step 166 occurs.

Figure 17D:
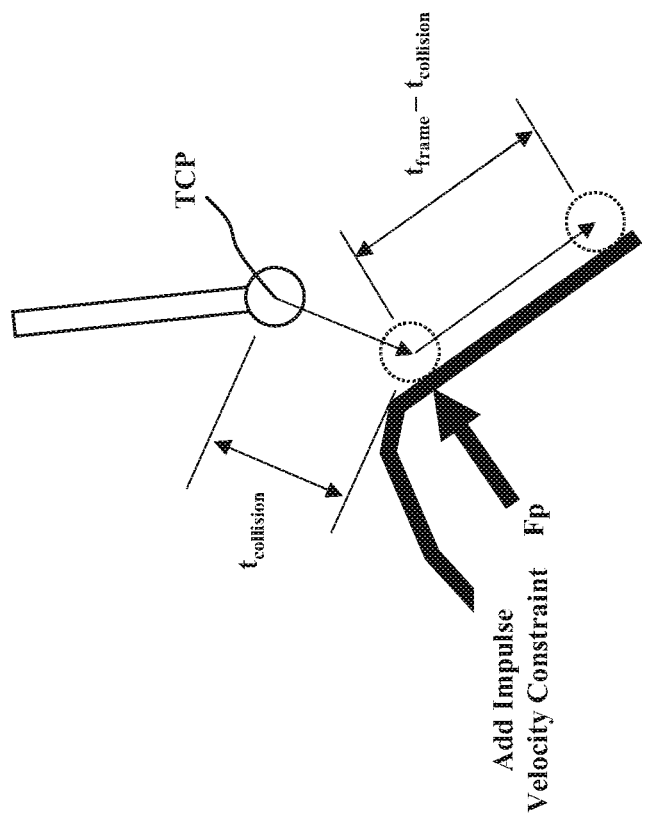

Next, referring to FIG. 16 and FIG. 17D, the control system 60 accounts for the time from when the collision occurs, collision time $t_{collision}$, until the end of the original time frame $t_{frame}$. In other words, the control system 60 performs a new virtual simulation for the time period $\Delta t = t_{frame} - t_{collision}$. The boundary constraints are obtained for this next round of virtual simulation in step 168 to effectively generate the virtual impulse needed to keep the tool 20 from crossing the virtual boundary 71 (or so the tool 20 only minimally crosses the virtual boundary 71). The boundary constraints obtained in step 168 are then used to update the constraints in step 133 and the virtual simulation is carried out for the new time period $t_{frame} - t_{collision}$ (see step 148). A new proposed state is determined and again transformed to the TCP in step 150. The toggle of step 152, being reset, again follows the first path, and a collision check is again performed in step 154. For some virtual boundaries 71, once a collision is detected, the steps described above will result in the next collision check always being negative, and a new commanded pose and velocity is output at step 160. However, for complex geometric shapes, even when the first collision is detected and addressed, the next round of virtual simulation may result in yet another collision. In this case, other steps to account for multiple collisions could be performed, but the processes shown in FIG. 16 are for the simpler case for purposes of illustration. In some cases, a maximum number of iterations of the virtual simulation may be set so that the process stops once the maximum number of iterations has been reached. If there is still a collision once the maximum number of iterations has been reached, this could be handled in a variety of ways: (i) output the latest proposed state as the final, updated state; (ii) output the prior frame's state (i.e., initial state) as the final, updated state; or (iii) signal an error and halt motion of the manipulator 14, tool 20, etc.

Figure 16A:
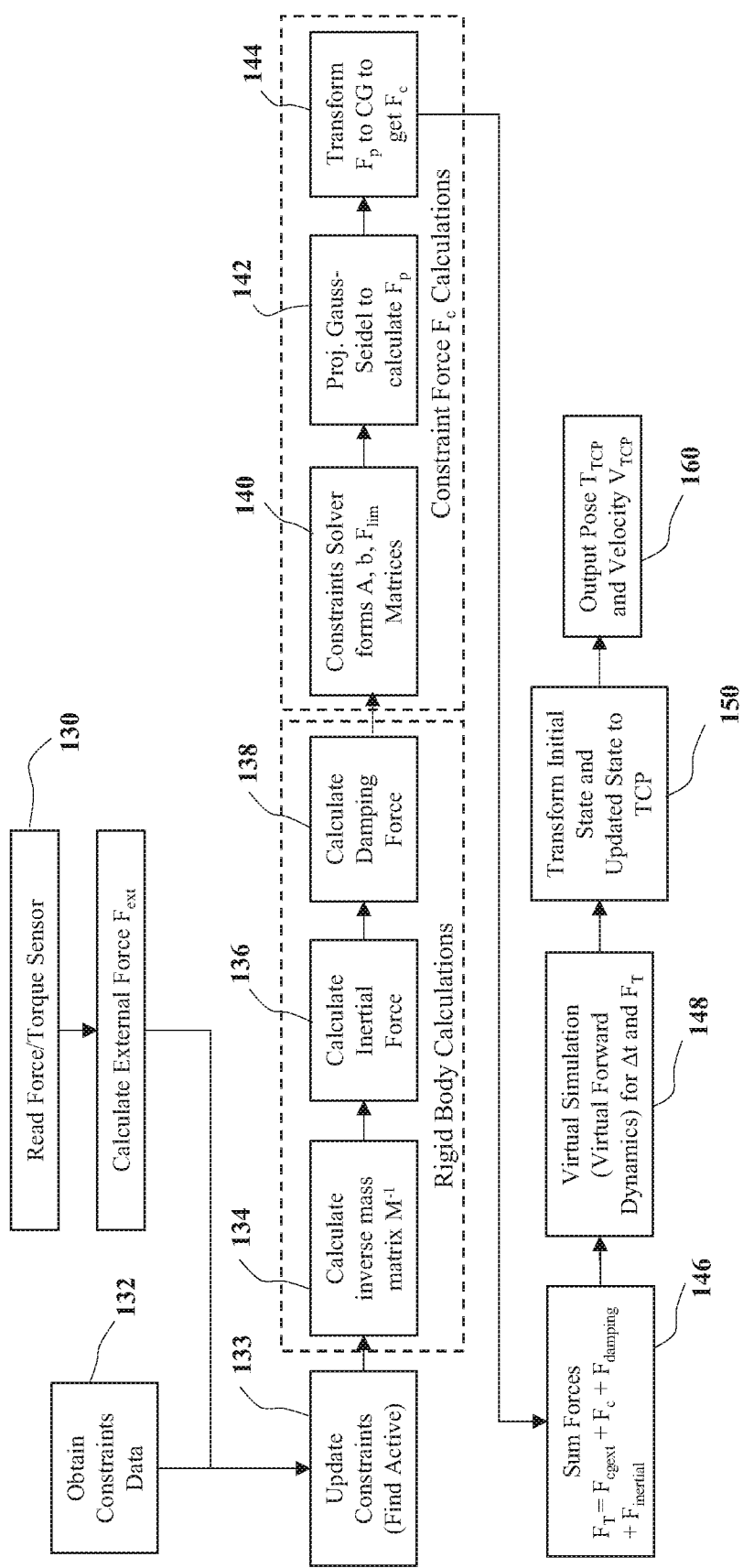
FIG. 16A shows an example set of steps carried out by the control system to solve constraints, perform forward dynamics, and determine a commanded pose.

Referring to FIG. 16A, in some versions, steps 152, 154, 156, 162, 164, 166, and 168 from FIG. 16 are removed and the output from the virtual simulation is instead set as the new, updated state that ultimately yields the new commanded pose. In this version, the first collision check is part of step 132 in which the boundary handler 90 determines the boundary constraints (if any) to feed into the constraint solver 84 (along with the other constraints).

VII. Example Operation

Figure 18A:
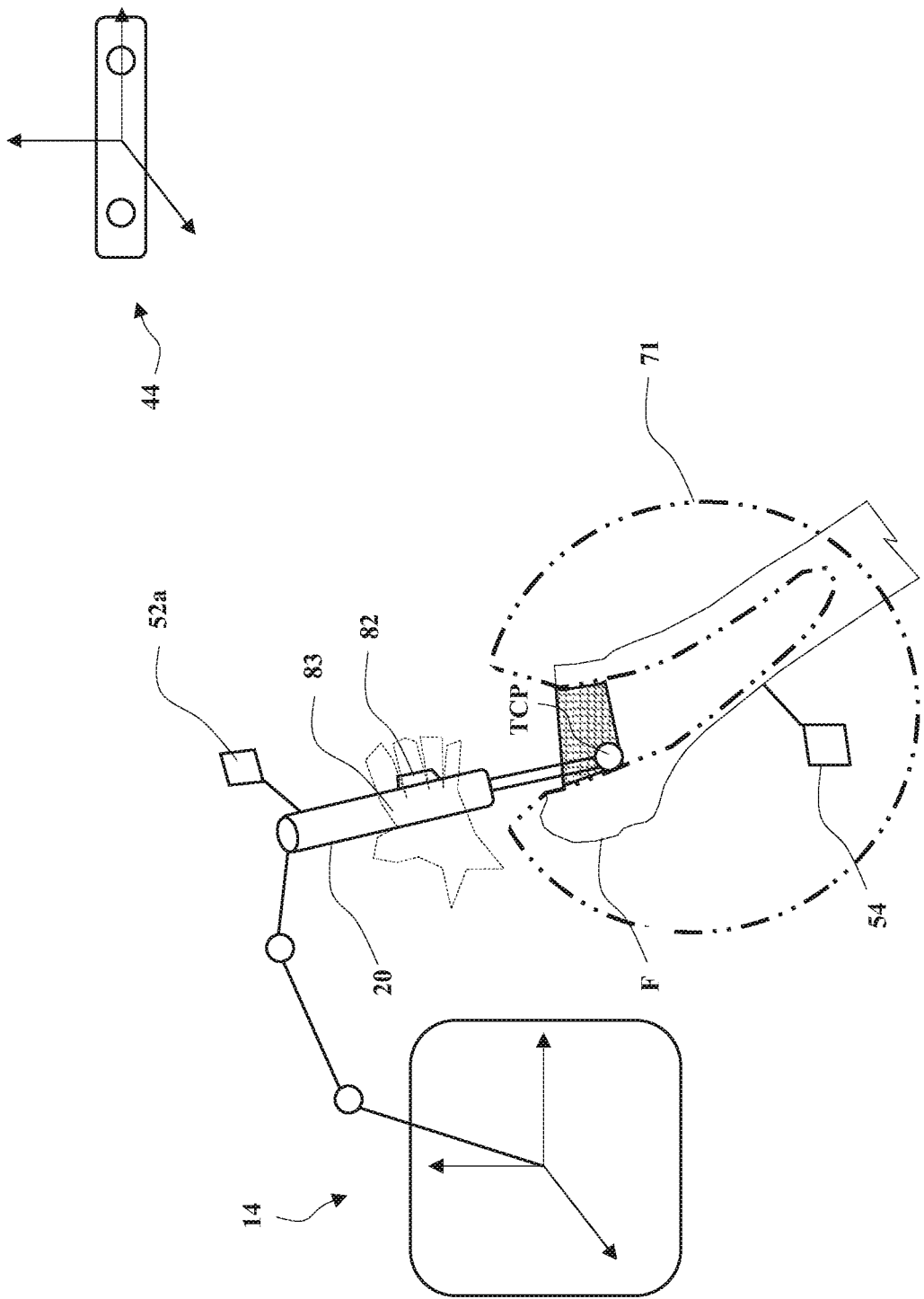

FIGS. 18A-18G illustrate one example of operation of the system 10. In FIG. 18A, the user is shown grasping the grip 83 of the tool 20 at the tool input 82 such that the tool input 82 has been actuated and is in the first input state. The user operates the manipulator 14 in the manual mode and in the boundary-enabled state to remove material from the target site (in this case from the femur F). The virtual boundary 71 is illustrated as being overlaid on the femur F, which may be visually shown to the user via the displays 38. In FIG. 18A, the user has already removed a small volume of tissue from the femur F with the tool 20, but there remains a substantial volume of material within the virtual boundary 71 that is yet to be removed. In this configuration, the control system 60 maintains the tool 20 within the virtual boundary 71 by enabling autonomous, boundary-complying movement of the tool 20, if needed, to account for any movement of the virtual boundary 71 that may otherwise cause the tool 20 to be in violation of the virtual boundary 71.

Figure 18B:
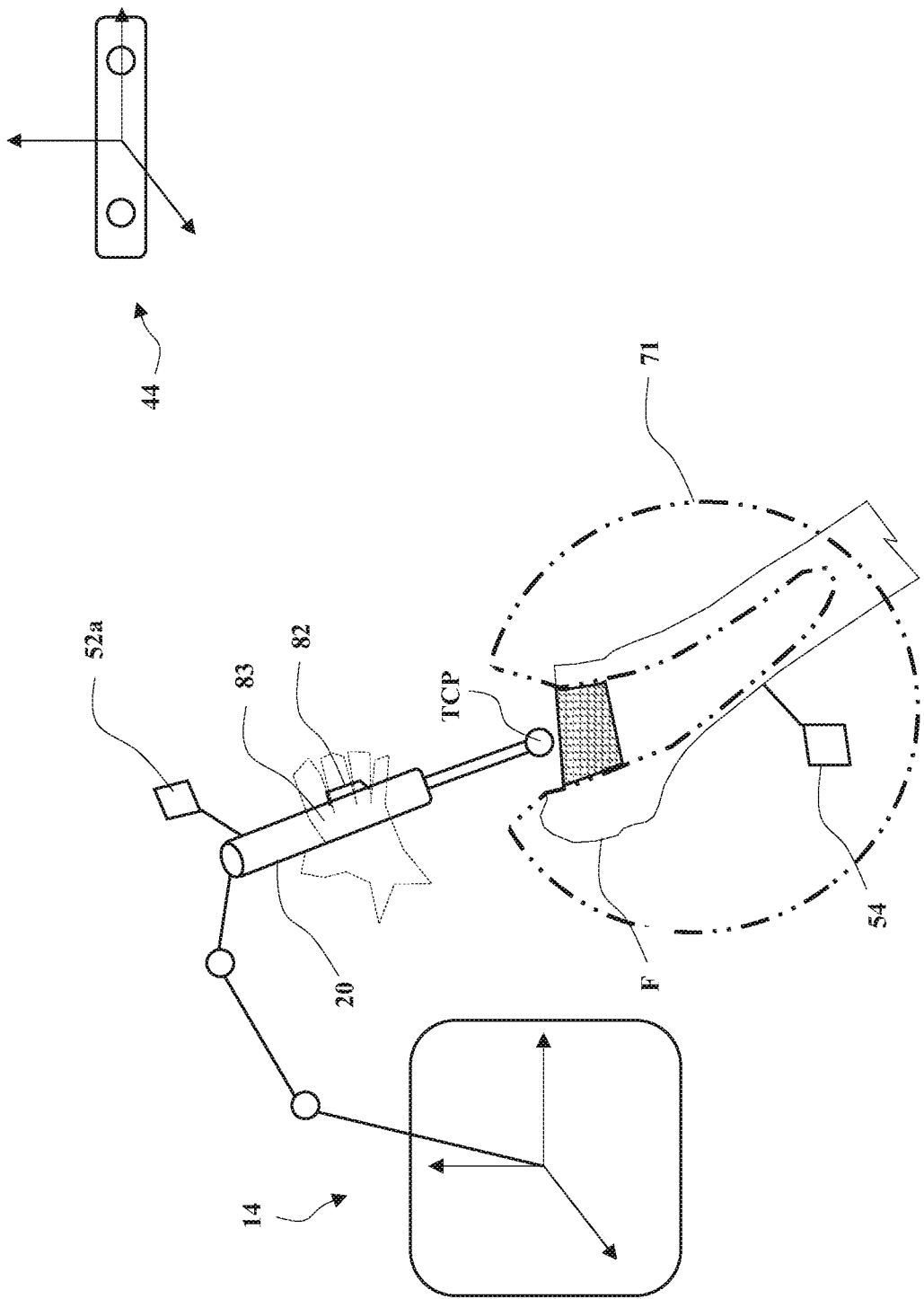

FIG. 18B illustrates the user moving the TCP of the tool 20 to above the femur F in preparation for moving the femur to make access to the femur F easier for the user.

Figure 18C:
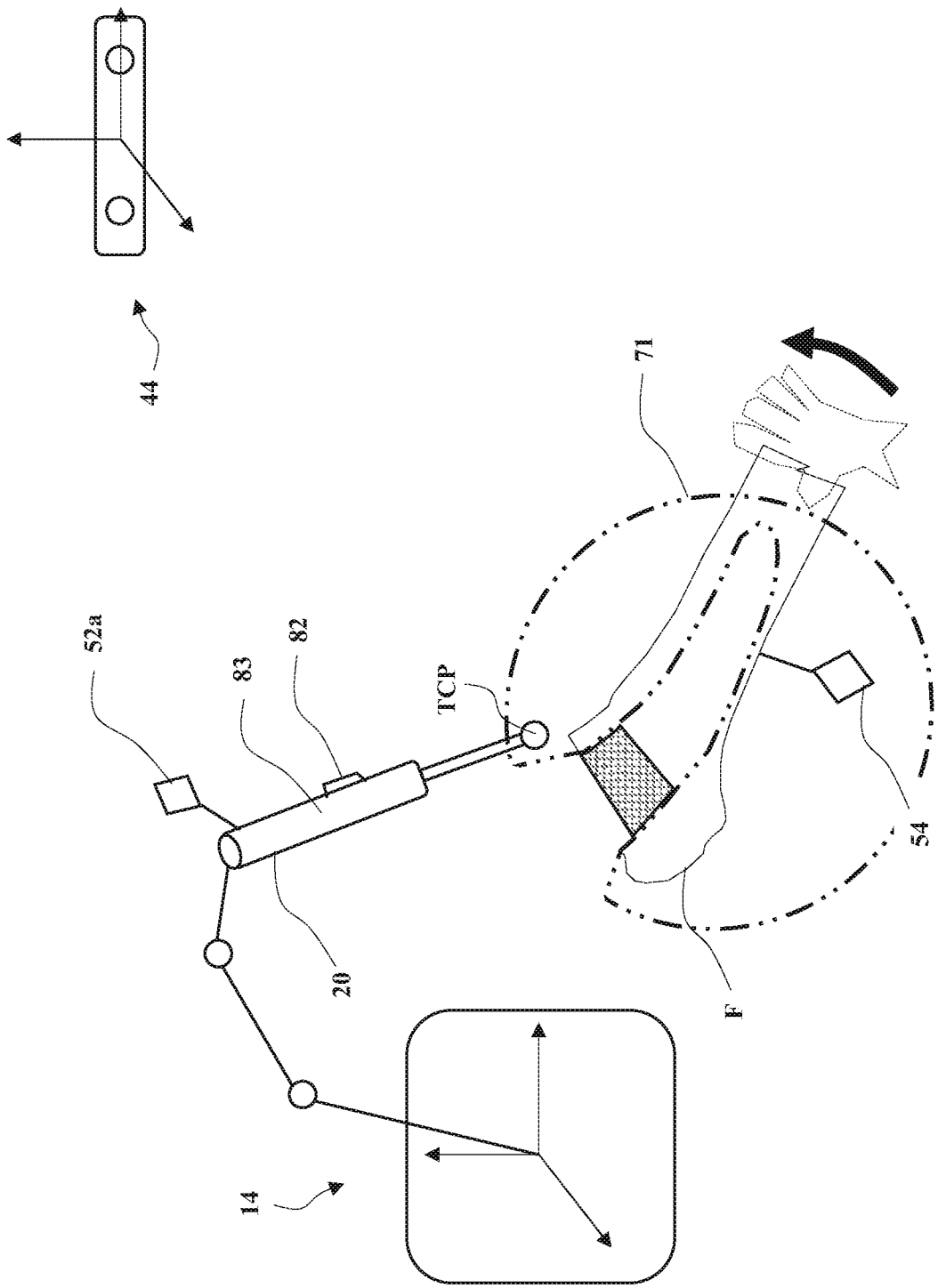

FIG. 18C illustrates the user's movement of the femur F. The user has removed their hand from the grip 83 of the tool 20 and the tool input 82 has been released. Accordingly, the tool input 82 is now in the second input state and the control system 60 is now switched to the hold mode and the boundary-disabled state. Accordingly, autonomous, boundary-complying movement of the tool 20 is disabled and the femur F can be moved by the user without causing any corresponding movement of the tool 20. Movement of the femur F is detected by the navigation system 32 by virtue of the localizer 44 tracking movement of the femur F via the first patient tracker 54 that is firmly affixed to the femur F. As shown, the tool 20 has moved to being outside of the virtual boundary 71.

Figure 18D:
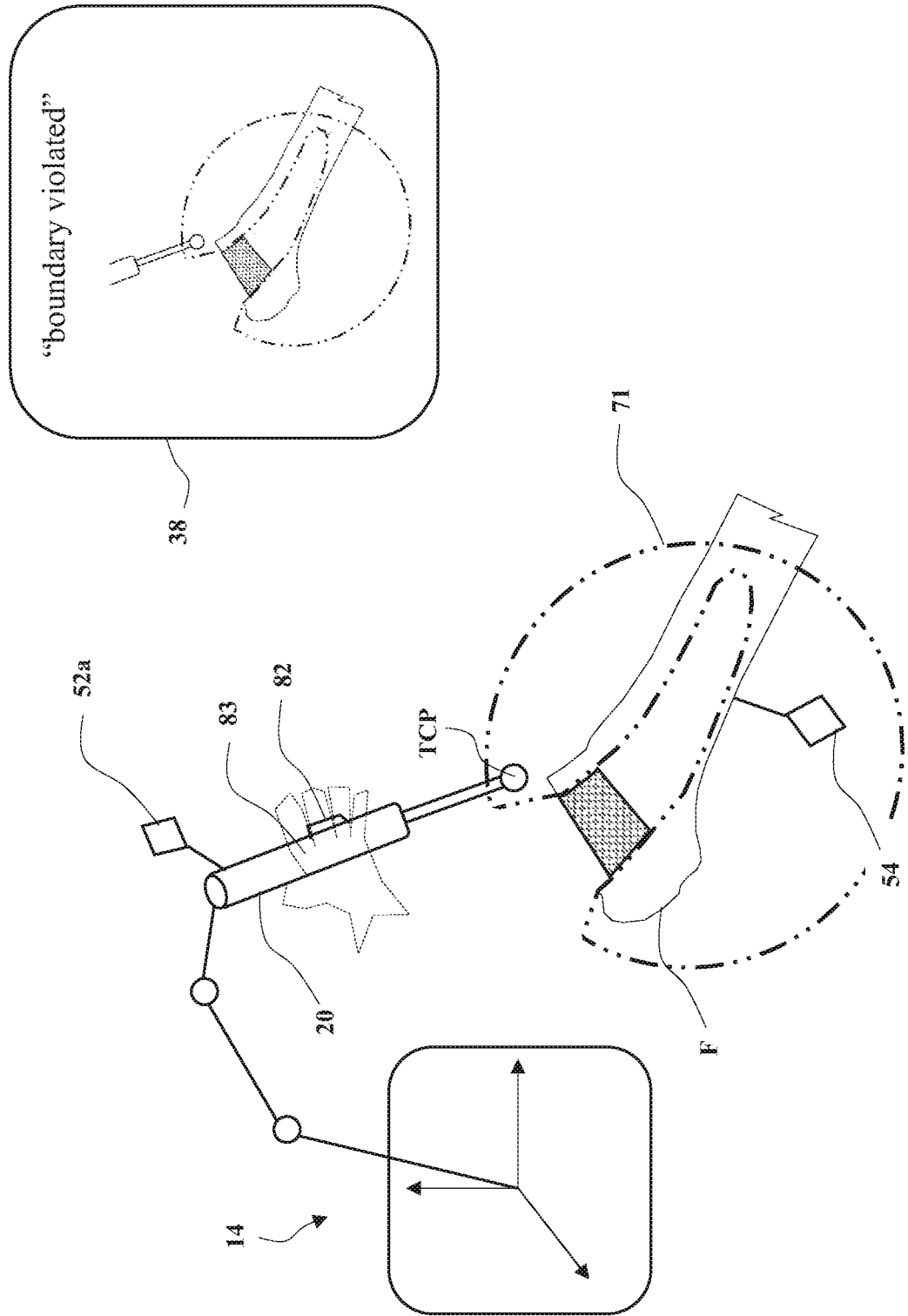

FIG. 18D illustrates the user again engaging the tool 20 to continue operation in the manual mode. More specifically, the user again actuates the tool input 82 to place the tool input 82 into the first input state. As previously discussed, this transition from the second input state to the first input state causes the boundary handler 90 to perform the second type of collision check. The result of this collision check is that the tool 20 is in violation of the virtual boundary 71. Accordingly, the guide handler 94 may provide user feedback of one or more forms to indicate this state of the tool 20 to the user and/or to guide the user into moving the tool 20 back into compliance with the virtual boundary 71. An alert and associated guidance is illustrated as being provided on one or more displays in FIGS. 18D and 18E. In FIG. 18E, the user has moved the tool 20 in the guided-haptic mode or in the free mode to be in compliance with the virtual boundary 71.

Figure 18F:
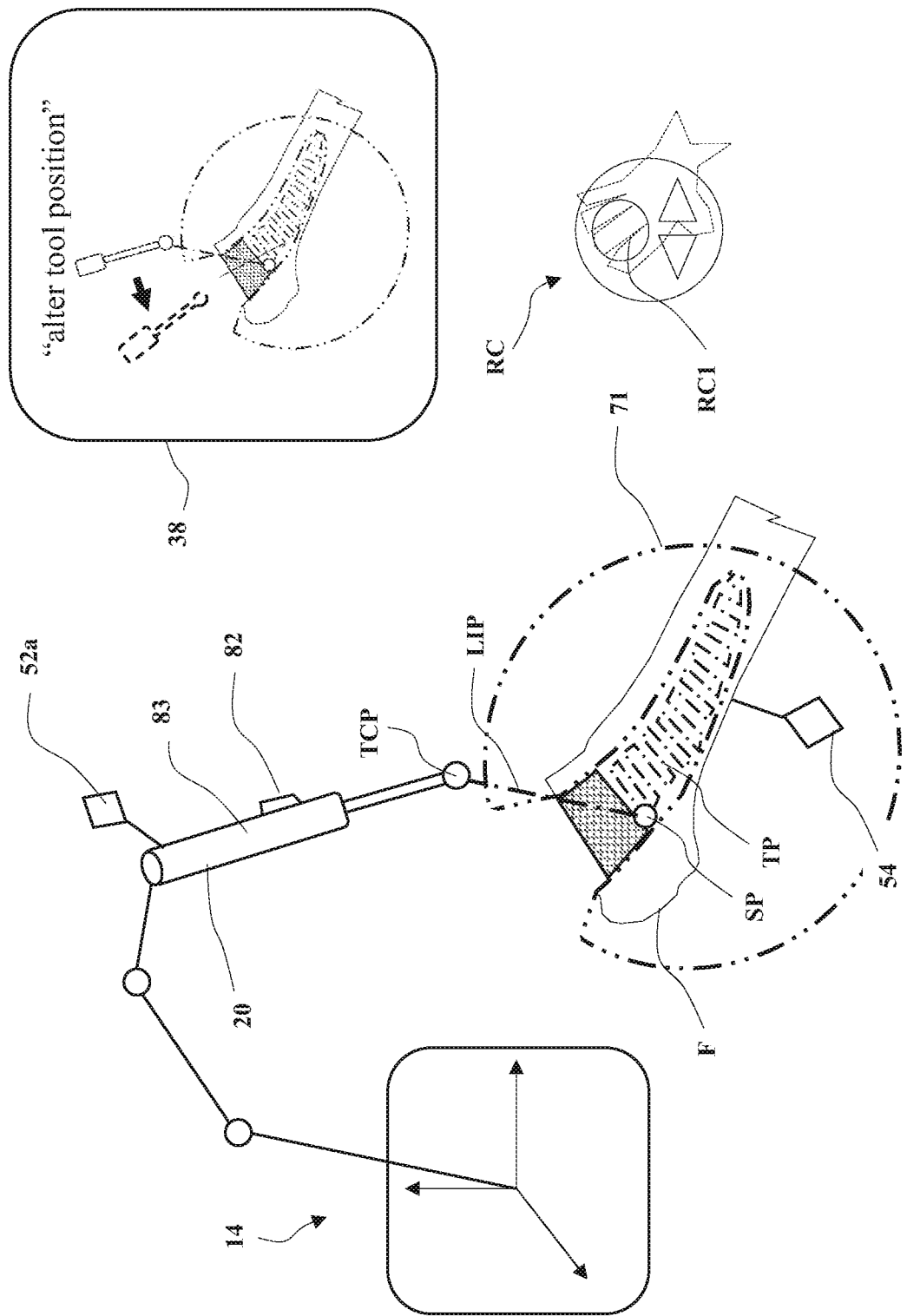

FIG. 18F illustrates the user now actuating the pendant input RC1 on the remote control RC to place the pendant input RC1 into the first input state to operate the system 10 in the semi-autonomous mode. More specifically, the user has released the tool input 82 to transition from the manual mode to the semi-autonomous mode. When the control system 60 transitions operation from the manual mode to the semi-autonomous mode, the control system 60 may perform a third type of collision check (e.g., in addition to performing the second type of collision check). More specifically, before the semi-autonomous mode is enabled, the path handler 88 defines a lead-in path LIP from the current pose of the tool 20 to a starting point SP on the tool path TP. This straight-line path may sometimes intersect the virtual boundary 71 (as shown in FIG. 18F) even though the current pose of the tool 20 and the starting point SP are both in compliance with the virtual boundary 71. The third type of collision check determines whether the lead-in path LIP generated by the path handler 88 violates the virtual boundary 71 or not.

If the virtual boundary 71 is not violated, then the control system 60 is enabled to autonomously move the tool 20 along the lead-in path LIP to the tool path TP in the semi-autonomous mode. If the virtual boundary 71 is going to be violated if the tool 20 were moved along the lead-in path LIP, then the control system 60 responds by indicating the same to the user and providing guidance to the user on how to move the tool 20 to avoid such a violation, as shown by the instruction "alter tool position" as shown on the display 38 in FIG. 18F. The semi-autonomous mode remains disabled.

The third type of collision check may be performed similar to the first type of collision check. As mentioned, the path handler 88 generates the lead-in path LIP from a current position (or pose) of the tool 20 to the starting point of the tool path TP when the manipulator 14 transitions from the manual mode to the semi-autonomous mode. The boundary handler 90 determines whether movement of the tool 20 along the lead-in path LIP would maintain compliance with the virtual boundary 71 or would violate the virtual boundary 71.

VIII. Other Collision Checks

Figure 18G:
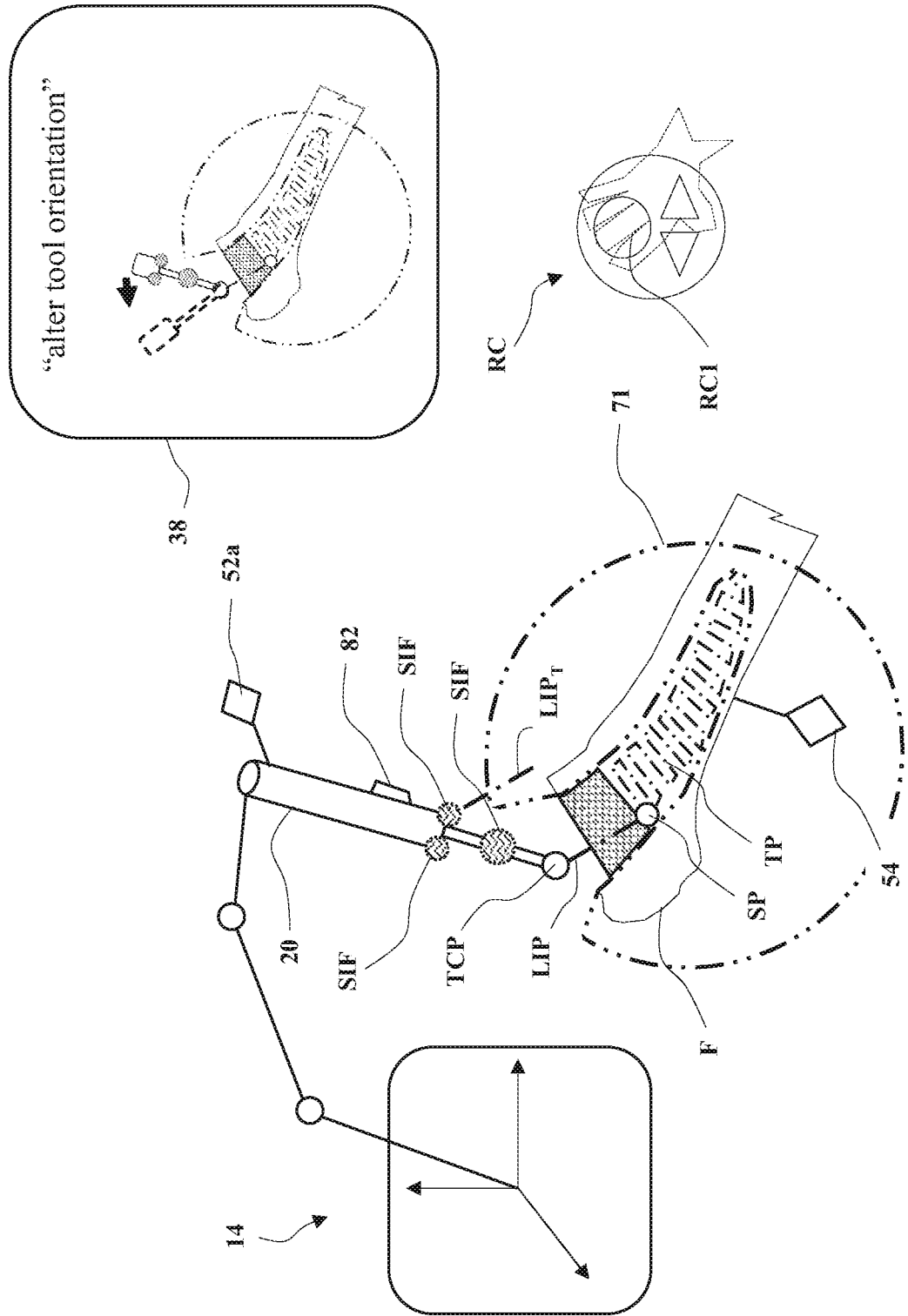

In some versions, illustrated in FIG. 18G, the boundary handler 90 is configured to determine whether movement of the tool 20 along the lead-in path LIP would maintain compliance with the virtual boundary 71 or would violate the virtual boundary 71 by modeling motion of a plurality of stereotactic interaction features SIFs associated with the tool 20 to determine if the stereotactic interaction features SIFs would maintain compliance with the virtual boundary 71 or would violate the virtual boundary 71. This may be performed by conducting similar collision checks for straight-line motion from the stereotactic interaction features SIFs. Such motion may be determined by transforming the lead-in path LIP and its corresponding orientation to each of the corresponding stereotactic interaction features SIFs (see $LIP_T$ in FIG. 18G). In some versions, the boundary handler 90 is configured to model more complex motion of the plurality of stereotactic interaction features SIFs in three or more degrees of freedom. The guide handler 94 generates feedback to the user in response to the boundary handler 90 determining that the tool 20 (e.g., any modeled points thereof) would violate the virtual boundary 71 if the tool 20 moved from the current position, along the lead-in path LIP, to the tool path TP.

The lead-in path LIP collision check may consider the enabled stereotactic interaction features SIFs and their shapes, which may be spheres and their locations configured for the tool 20, and make sure to sweep each of them through the range of motion each would encounter while the TCP traverses the proposed lead-in path LIP. Note that the lead-in path LIP could include alignment of position and/or orientation to the starting point SP (for the case of greater than 3-DOF autonomous machining), i.e., the resulting movement of each stereotactic interaction feature SIF during the lead-in is not necessarily a straight line. Accordingly, the control system 60 may: (i) model the motion of each stereotactic interaction feature SIF precisely and perform continuous collision detection according to the applicable translation/rotation trajectory, or as illustrated, (ii) approximate the stereotactic interaction feature SIF trajectory by sweeping the collision shape translationally-only between its start and end location. If the lead-in path collision check fails, the user is alerted prior to any motion of the tool 20 (i.e., the manipulator 14 stays in the hold mode, free mode, or manual mode), along with potentially enhanced visual information via the display 38 on how to resolve the situation.

Figure 19:
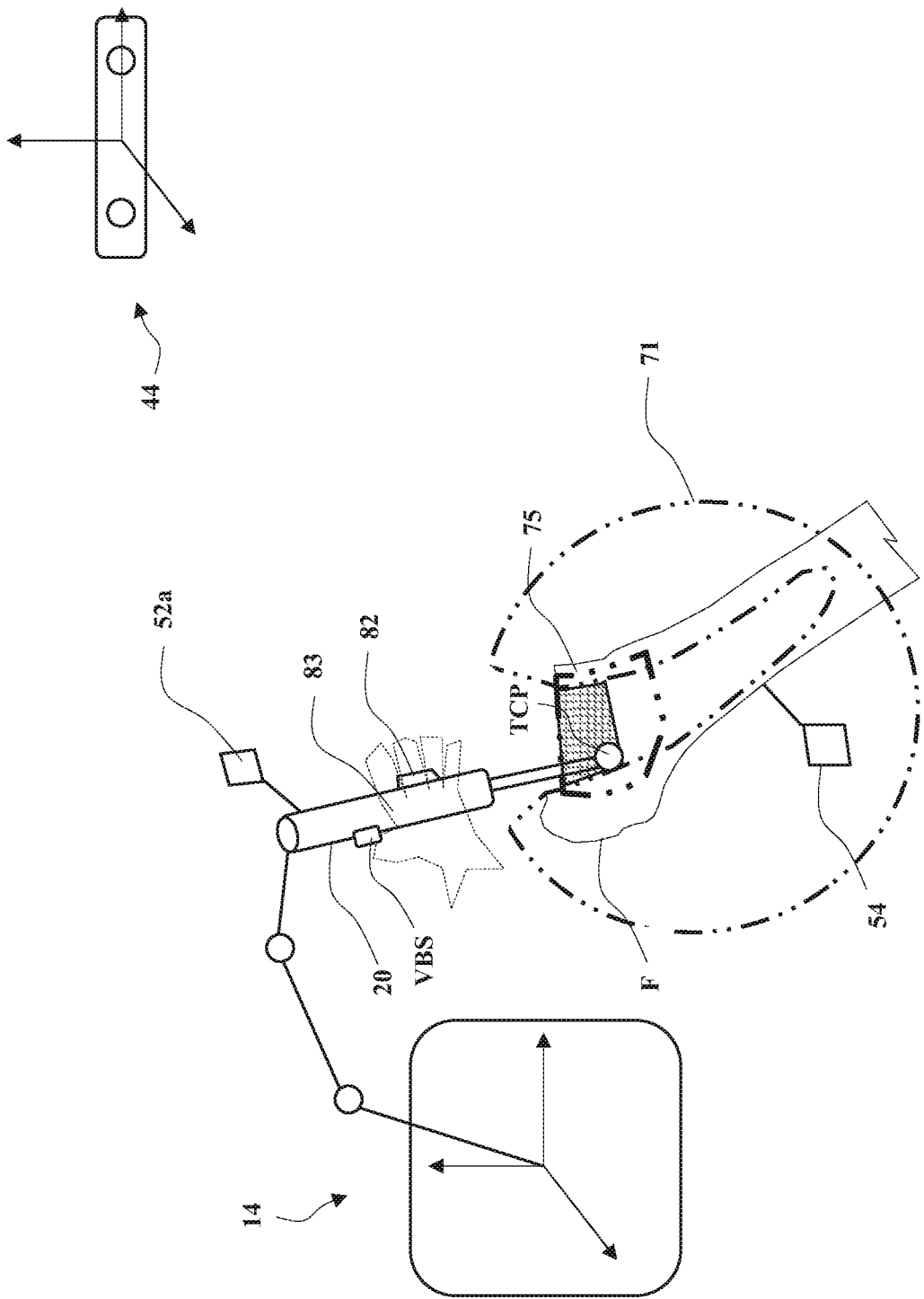
FIG. 19 illustrates switching between first and second virtual boundaries.

Referring to FIG. 19, the boundary handler 90 may be configured to perform a fourth type of collision check when the user desires to switch from the current virtual boundary (shown as a first virtual boundary 71) to a second virtual boundary 75 during operation in the manual mode or the semi-autonomous mode. If the user desires to change virtual boundaries in the middle of a surgical procedure, such as switching from the first virtual boundary 71 to the second virtual boundary 75, then the boundary handler 90 checks to ensure that the second virtual boundary 75 is not going to be violated should the switch occur (e.g., in the same manner that the first virtual boundary 71 is evaluated for violations as previously described, including taking into account any tolerance set for the second virtual boundary 75). If the second virtual boundary 75 will be violated, then the control system 60 continues operation with the first virtual boundary 71 being enabled and the second virtual boundary 75 disabled. However, if the second virtual boundary 75 will not be violated, then the control system 60 activates the second virtual boundary 75 and deactivates the first virtual boundary 71.

A virtual boundary selector VBS may be utilized by the user to indicate a desire to switch to the second virtual boundary 75. The virtual boundary selector VBS enables the user to select the second virtual boundary 75, which may also be associated with the target site, such that the control system 60 thereafter controls operation of the manipulator 14 and movement of the tool 20 to maintain compliance of the tool 20 with the second virtual boundary 75 in the same manner as the control system 60 employed to maintain compliance with the first virtual boundary 71. The virtual boundary selector VBS may include a user input located on the manipulator 14, the tool 20, the remote control RC, etc. The user input of the virtual boundary selector VBS may be any suitable form of input device, including those previously described herein. The virtual boundary selector VBS may enable a user to toggle between the first and second virtual boundaries 71, 75, toggle sequentially from among a plurality of virtual boundaries, or select from a list of virtual boundaries.

The control system 60 enables the user to select the second virtual boundary 75 with the virtual boundary selector VBS while the control system 60 continues to control operation of the manipulator 14 and movement of the tool 20 to maintain compliance of the tool 20 with the first virtual boundary 71. The boundary handler 90 determines, in response to the user selecting the second virtual boundary 75, whether the tool 20 is in compliance with the second virtual boundary 75 or is in violation of the second virtual boundary 75, and the boundary handler 90 activates the second virtual boundary 75 and deactivates the first virtual boundary 71 if the boundary handler 90 determines that the tool 20 is in compliance with the second virtual boundary 75 so that the control system 60 transitions controlling operation of the manipulator 14 and movement of the tool 20 from being based on the first virtual boundary 71 to being based on the second virtual boundary 75. The boundary handler 90 is configured to maintain the first virtual boundary 71 as being active if the boundary handler 90 determines that the tool 20 is in violation of the second virtual boundary 75 in response to the user selecting the second virtual boundary 75 via the virtual boundary selector VBS.

The control system 60 generates user feedback to the user in response to the boundary handler 90 determining that the tool 20 is in violation of the second virtual boundary 75 when the user actuates the virtual boundary selector VBS to select the second virtual boundary 75. The control system 60 is configured to enable the user to select the second virtual boundary 75 with the virtual boundary selector VBS while the tool input 82 or the pendant input RC1 is in the first input state. Moreover, the control system 60 continues operation of the tool drive when the user selects the second virtual boundary 75 with the virtual boundary selector VBS. In some versions, the user may also be able to select the second virtual boundary 75 with the virtual boundary selector VBS while the tool input 82 and the pendant input RC1 are in the second input state.

In some versions, the user is able to select the second virtual boundary 75 with the virtual boundary selector VBS on-the-fly, meaning that the manual mode or the semi-autonomous mode is active (e.g., one of the tool input 82 or the pendant input RC1 is engaged in the first input state) and the manipulator 14 and the tool 20 are moving. If the fourth type of collision check indicates a violation of the second virtual boundary 75, the user/manipulator 14 is not halted or forced to stop operating/moving the tool 20 since a valid boundary constraint remained active (e.g., for the first virtual boundary 71).

In some examples, the first and second virtual boundaries 71, 75 may be considered standard and extended boundaries for a total knee procedure, or other surgical procedure. The standard boundary may have limited dimensions (e.g., height, width, and/or depth) based on implant size and the extended boundary may have one or more dimensions greater in magnitude than the standard boundary (e.g., greater width) to allow the user to access more tissue (e.g., bone) with the tool 20. The control system 60 may default operation to the standard boundary. Based on user input via the virtual boundary selector VBS, if needed, the user can switch to the extended boundary that allows a larger amount of tissue to be reached. Once the user has finished machining the areas in which the user needed the larger (e.g., wider) boundary, the user may desire to switch back to the standard boundary to apply for the rest of the cut. Using the fourth type of collision check, the user can only return from the extended boundary to the standard boundary if the tool 20 is within the region allowed for the standard boundary. If not, the user interface (e.g., the display) indicates the violation and the failed switch back to the standard boundary and the user can retry later by actuating the virtual boundary selector VBS again.

The control system 60 limits relative movement between the tool 20 and the second virtual boundary 75 when the tool input 82 or the pendant input RC1 is in the first input state and the second virtual boundary 75 is active by generating second boundary constraints for the second virtual boundary 75 with the boundary handler 90. The constraint solver 84 may calculate the constraint force $F_c$ to maintain the tool in compliance with the first virtual boundary 71 based on the first boundary constraints or in compliance with the second virtual boundary 75 based on the second boundary constraints when the user has successfully selected the second virtual boundary 75 with the virtual boundary selector VBS.

Note that the collision check/activate/de-activate steps for transitioning from the first virtual boundary 71 to the second virtual boundary 75 may be done atomically (i.e., in the same time step), to avoid race conditions of movement between the collision check and activation or time gaps during which neither or both virtual boundaries 71, 75 are active. The virtual boundaries 71, 75 may also be referred to as collision scenes. If the collision check fails, the collision scene is not updated from the first collision scene to the second collision scene. Since the active collision scene is not de-activated unless the collision check passes, the control system 60 is able to maintain its operation as of just prior to the transition request. User feedback may be given to notify the user of the failed transition, e.g., audible feedback, user message on the displays 38, haptic feedback, etc. While it could be done automatically, it is typically desired to let the user decide when/if to re-attempt the transition from 'active' to 'new' collision scene, at which time the sequence above is repeated.

In some situations, when the user's attempt to switch to the second virtual boundary 75 fails and the first virtual boundary 71 remains active, an assistance mode may be activated to help place the tool 20 into compliance with the second virtual boundary 75. In the assistance mode, the same control described for the recovery mode could be employed to help place the tool 20 into compliance with the second virtual boundary 75, except that the manual mode or the semi-autonomous mode remain active by virtue of the first virtual boundary 71 still being used to generate boundary constraints to maintain compliance with the first virtual boundary 71.

The assistance mode may include the control system 60: (i) generating visual cues on the display or elsewhere to guide the user into causing movement of the tool 20 that places the tool 20 into compliance with the second virtual boundary 75; (ii) generating guide constraints with the guide handler 94 to guide the user into compliance with the second virtual boundary 75; (iii) generating an assistance tool path to autonomously move the tool 20 into compliance with the second virtual boundary 75; (iv) moving the second virtual boundary 75 from its starting location such that the tool 20 is in compliance with it and then gradually moving the second virtual boundary 75 back to its starting location to gently pull the tool 20 along with it; and/or (v) generating assistance constraints associated with the second virtual boundary 75 that have tuning parameters lower than the tuning parameters of the original boundary constraints for the second virtual boundary 75 such that the tool 20 can more gradually transition to being in compliance with the second virtual boundary 75 (i.e., the second virtual boundary 75 is effectively altered to be less stiff). Other methods for guiding the tool 20 into compliance with the second virtual boundary 75 are also contemplated. In some cases, one or more of these methods may be considered by the control system 60 and executed if certain conditions are met. The control system 60 may check to see how close the tool 20 is to the second virtual boundary 75, and then select the appropriate method. For instance, if the tool 20 is within 1-2 mm of the second virtual boundary 75, then activating the second virtual boundary 75 with temporarily looser tuning parameters may be enabled, or temporarily shifting the second virtual boundary 75 may be appropriate. Once the tool 20 complies with the second virtual boundary 75, the control system 60 may switch control to the second virtual boundary 75 manually or automatically. Other implementations include backtracking along the tool axis, e.g., for TKA or THA acetabular preparation for the rim osteophyte.

The remote control RC and/or other input devices on the various user interfaces UI may be employed to switch between, activate, and/or deactivate the various modes of operation of the manipulator 14. The control system 60 may be configured to automatically switch modes in certain situations. The control system 60 may also first prompt the user before operating in the manual mode or the semi-autonomous mode if these modes are initially disabled when selected, because the tool 20 is found to be in violation of the virtual boundary 71 by the boundary handler 90. The control system 60 may also prompt the user before operating in the guided-haptic mode. Such prompting may include providing selectable prompts on one or more of the displays 38 to continue in the manual mode, the semi-autonomous mode, or the guided-haptic mode. The user may select to continue in the manual mode, semi-autonomous mode, guided-haptic mode, etc. via any suitable input device on any user interface UI, including on the remote control RC.

The current state of the tool 20 relative to the virtual boundaries 71, tool path TP, target state, and/or relative to the target site may be output by the navigation system 32 and represented on the displays 38 via graphical representations of the tool 20, virtual boundaries 71, tool path TP, target state, and/or the target site, e.g., the femur F, tibia T, pelvis PEL, vertebral body, or other anatomy. These graphical representations may update in real-time so that the user is able to visualize movement of the tool 20 relative to the virtual boundaries 71, tool path TP, target states, anatomy, etc. For example, the graphical representations of the tool 20 and anatomy may move on the displays 38 in real-time with actual movement of the tool 20 by the manipulator 14 and actual movement of the anatomy.

The various modes described herein may be employed in various types of surgical systems. For example, the manipulator may comprise a tele-manipulated robotic arm that is controlled via a user interface that is remotely located relative to the tele-manipulated robotic arm to control the tele-manipulated robotic arm. The user interface may comprise a separate manipulator such as a 6-DOF control unit that is manually manipulated by a user, e.g., a separate manipulator with active joints to provide haptic feedback to the user.

IX. Stereotactic Interaction Features

As described above, stereotactic interaction features SIFs may be utilized by the system for collision detection. Described in this section are various configurations or implementations by which the SIFs may be implemented or utilized. The following configurations or implementations of the SIFs may be utilized with any of the above described techniques or components, which are incorporated fully by reference in this section. Alternatively or additionally, the following configurations or implementations of the SIFs may be utilized independent of any of the above described techniques, and for other general purposes, such as, but not limited to: robotic control, collision avoidance, user experience, or the like.

The stereotactic interaction features SIFs can be attributed to any object which can interact with a virtual boundary 71. Optionally, the SIFs can be attributed to any component a pose of which can be controlled (manually, automatically, or kinematically). For example, the SIFs can be attributed to any part of the robotic surgical system, the tool 20, the end effector 22, the energy applicator 24 or TCP, the manipulator 14, any links 18 or joints J of the manipulator 14, the base 16, or any other part of the kinematic chain that forms the manipulator 14. The SIFs can be attributed to other objects or surgical components in the operation room, such as hand-held tools, the surgical table, head-mounted devices, hand-held display devices or tablets, trackers, retractors, the patient, the personnel or staff, or the like. The positions of the SIFs can be known because any of the objects can be tracked using any suitable method, including but not limited to the localization techniques described above. The objects to which the SIFs are attributed may be selected based on input into the program and/or automatically generated, for example, based on factors such as the surgical plan, type or step of operation, surgeon preferences, and the like.

Figure 20:
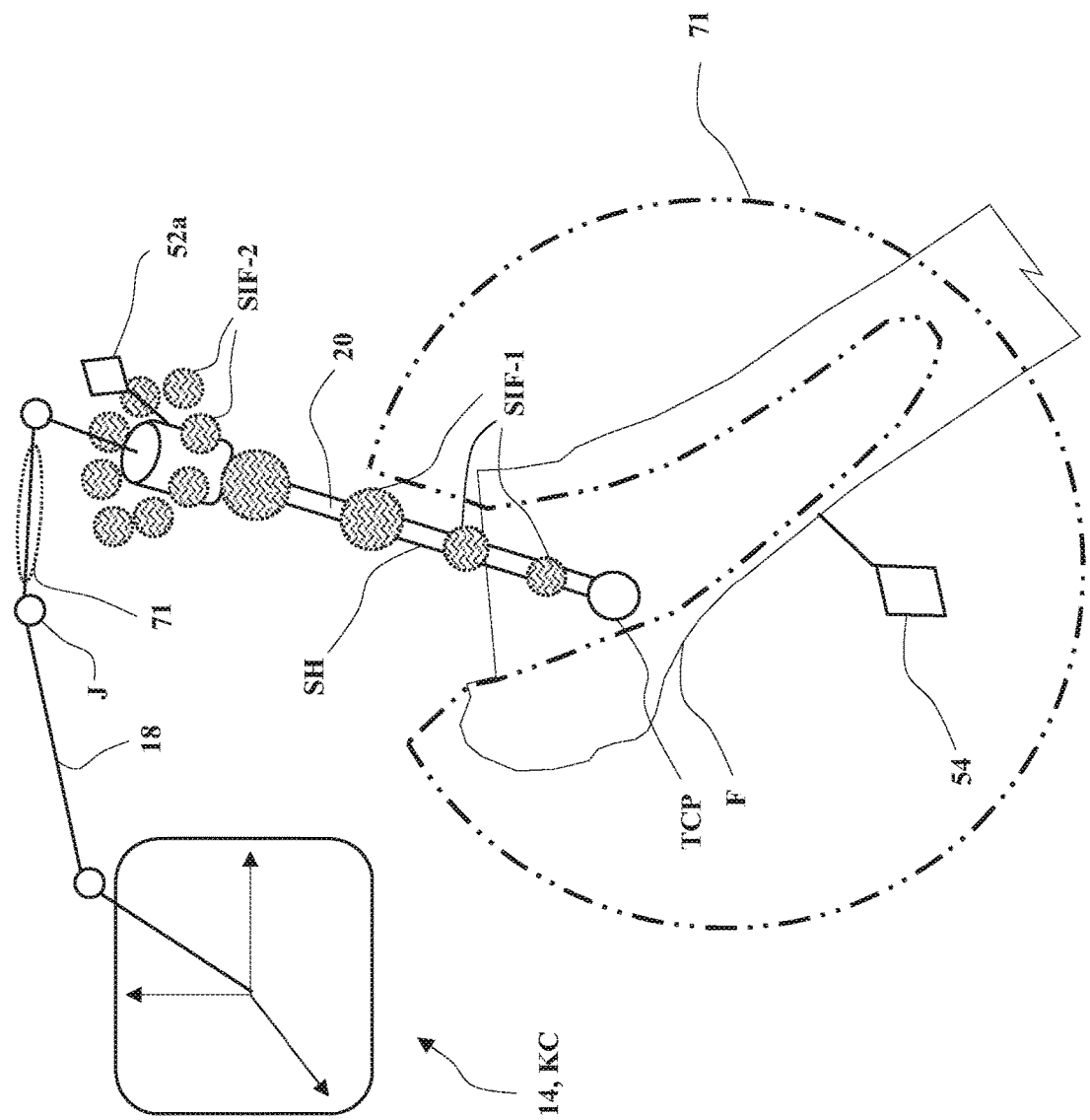
FIG. 20 illustrates multiple stereotactic interaction features associated with a component of the robotic surgical system.

Furthermore, the virtual boundary 71 described in this section can be attributed to any object other than the anatomy. For example, the virtual boundary 71 can be attributed to any part of the robotic surgical system, the tool 20, the end effector 22, the energy applicator 24 or TCP, the manipulator 14, any links 18 or joints J of the manipulator 14, the base 16, or any other part of the kinematic chain that forms the manipulator 14. The virtual boundary 71 can be attributed to other objects or surgical components in the operation room, such as imaging devices (c-arms, gantries, CT scanners, etc.), hand-held tools, the surgical table, head-mounted devices, hand-held display devices or tablets, trackers, retractors, the patient, the personnel or staff, or the like. The virtual boundary 71 can have any suitable shape or configuration depending on the object to which it is attributed. For example, if the virtual boundary 71 is attributed to a link 18 of the manipulator 14, the virtual boundary 71 may take the shape of a volume surrounding the link 18, as shown in FIG. 20, for example. Other configurations are contemplated. The location of the virtual boundary 71 can be known because any of the objects can be tracked using any suitable method, including but not limited to the localization techniques described above. The objects to which the virtual boundaries 71 are attributed may be selected based on input into the program and/or automatically generated, for example, based on factors such as the surgical plan, type or step of operation, surgeon preferences, and the like.

The SIFs can be defined, located, customized, and implemented using the control system 60 described in the previous sections, including the software program 78 and boundary handler 90. The boundary handler 90 may detect a collision of between any number of SIFs and the virtual boundary 71 using any suitable method. In response to a collision or anticipated collision between any one or more SIFs and the virtual boundary 71, the control system can adjust the pose of the respective object, and/or generate an alert or notification. Such response from the control system is provided to reactively or proactively prevent, avoid, mitigate, or reduce the collision.

Any number of SIFs can be attributed any number of objects. In the example of FIG. 20, multiple SIFs are attributed to the tool 20, which in this case is an elongated cutting bur for milling a femur F for THA. Of course, this example is for illustrative purposes and is not intended to limit the scope of how the SIFs can be utilized. The number of SIFs attributed may be defined based on input into the program and/or automatically generated, for example, based on factors such as the surgical plan, type or step of operation, surgeon preferences, and the like.

In some implementations, the SIFs can be attributed to locations that are directly located at the object to which the SIF is attributed. For example, in FIG. 20, several SIFs, identified as SIF-1, are attributed directly to the shaft SH of the tool 20. These SIF-1s are spaced apart from one another along the shaft SH and directly on the shaft SH. In this example, the SIF-1s are provided to avoid collision between the shaft SH and the virtual boundary 71 attributed to the interior surface of the canal of the femur F. For instance, as the TCP follows the tool path during milling, the tool 20 may be routinely reoriented, which in turn causes a reorientation of the shaft SH. Having multiple SIF-1s along the shaft SH reduces the likelihood of a physical collision between the shaft SH and the anatomy in response to such reorientations.

In other implementations, the SIFs can be attributed to locations that are spaced apart from the object to which the SIF is attributed. For example, in FIG. 20, several SIFs, identified as SIF-2, are attributed to a proximal end of the tool 20. These SIF-2s are spaced apart from the tool 20 by a specified distance. The spacing of the SIF-2s in this example may be appropriate because the tool 20 is more likely to experience greater orientational movement (e.g., angular motion) near the proximal end as compared with near the TCP in response to reorientations. Hence, the spacing of the SIF-2s from the tool 20 provide an added cushion, or earlier response to collision or anticipated collision. In this example, the SIF-2s are arranged to form a ring of SIFs at the proximal end. The configuration or arrangement of the SIFs can be derived directly from the geometry of the object, e.g., a 2D cross-section of the shaft SH or tool 20. The SIFs can be located directly abutting one another or spaced apart from one another.

The spacing of SIFs relative to the respective object to which they attributed can be defined based on input into the program and/or automatically generated, for example, based on factors such as the surgical plan, type or step of operation, surgeon preferences, and the like.

In other implementations, the SIFs can be configured with any suitable geometry. For example, the SIFs can be points, areas, or volumes. The SIFs can have any suitable shape. In the example of FIG. 20, the SIFs have spherical shape. However, other 2D shapes or volumes are contemplated, such as, but not limited to: planes, hyperboloids, paraboloids, cylinders, cubes, pyramids, cones, cuboid, ellipsoid, prism, or any type of polyhedron. For any type of geometric configuration, the SIFs can also be configured with any suitable size. For instance, in FIG. 20, the spherical SIF-1s increase in volume as the SIF approaches the proximal end of the tool 20. Again, this may be implemented to provide an earlier response to collision or anticipated collision. The geometric configuration or size of SIFs can be defined based on input into the program and/or automatically generated, for example, based on factors such as the surgical plan, type or step of operation, surgeon preferences, and the like.

In one implementation, the SIFs are not infinitely rigid, but instead each of the SIFs may have tuning (stiffness) parameters to adjust the stiffness of SIF relative to virtual constraints, e.g., by incorporating spring and damping parameters into the constraints. Such parameters may include a constraint force mixing parameter (C) and an error reduction parameter ($\epsilon$). The spring and damping parameters may be adjusted before or during operation. The tuning parameters for the SIFs may be different for different objects, conditions, locations, or geometric configurations. The SIFs may comprise a first SIF that has a first value for a tuning parameter and a second SIF that has a second value for the tuning parameter, the first value being greater than the second value so that the resulting virtual forces and/or torques embodied in the constraint force $F_c$ are adapted to effect movement of the tool 20 more strongly as a result of the first SIF as compared to the second SIF. The values of the tuning parameters may be greater (e.g., stiffer) for position constraints than for orientation constraints, or vice versa.

The tuning parameters for the SIFs may also be set to: remain constant; rise/fall exponentially with constraint distance; vary linearly with constraint distance; vary with constraint direction; take gravitational effects into account; and the like. The tuning parameters can also be scaled depending on the constraint force $F_c$ that is ultimately computed based on the virtual constraints, such as by increasing/decreasing the stiffness depending on the magnitude of the constraint force $F_c$, or any components thereof. The tuning parameters of the SIFs and their values, their correlation to a particular relationship, and the manner in which they may be scaled, may be stored in one or more look-up tables in any suitable memory in the control system 60 for later retrieval.

In one implementation, a first tuning parameter can be defined for the first SIF and define a second tuning parameter can be defined for a second SIF. The first tuning parameter and the second tuning parameter have different values. In one example, the first and second differently tuned SIFs are located on different components of a kinematic chain KC of the robotic manipulator 14. The differently tuned SIFs can also be located at different positions on the same component of the kinematic chain KC. The kinematic chain KC is formed by the manipulator 14, including any rigidly attached components such as the base 16, the plurality of links 18 and joints J, the tool 20 including the shaft SH (if applicable) and the energy applicator 24. The end effector 22 can also be part of the kinematic chain KC. Furthermore, any mounting system or sterile interface coupled between the manipulator 14 and end effector 22 can be part of the kinematic chain KC. One example of the mounting system and/or sterile interface mechanism that can be part of the kinematic chain is described in United States Patent Application Publication No. US 2020/0170724A1, entitled "Mounting System With Sterile Barrier Assembly For Use In Coupling Surgical Components", the entire contents of which are incorporated by reference herein. As used herein, the term "kinematic chain" is an assembly of rigid bodies connected by joints, wherein the rigidity of the bodies enable constrained motion such that kinematics of the rigid bodies can be determined and related to other rigid bodies in the chain using a mathematical model. In the example of FIG. 20, the kinematic chain further forms a "mechanism" because at least one link being mechanically grounded.

In the example of FIG. 20, the differently tuned first and second SIFs can be located on the tool 20 and/or shaft SH. In this case, the tuning parameter of the SIF-2s may be stiffer (e.g., greater damping or greater spring constant) than that of the SIF-1s due to potential for undesired orientational motion of the shaft SH being greater near the proximal end of the tool 20. Greater stiffness of the SIF-2s may cause the manipulator 14 to command a less disruptive corrective motion near proximal end of the tool 20. In other examples, the SIF-2s can be less stiff than the SIF-1s. This tuning configuration can be implemented to provide smoother transitions when there is collision between the energy applicator/tool and the virtual boundary 71. While this implementation can initially lead to greater penetration of the virtual boundary 71 by the shaft SH or tool 20, other behavior of the robotic manipulator can be changed before, during or immediately after penetration to account for such greater penetration resulting from the collision. Furthermore, having different tuning parameters for the SIFs can reduce the probability that collision with the boundary 71 can cause an error condition causing operation of the manipulator 14 to halt. Such tuning parameter configurations can apply to any number of SIFs for purposes of mitigating undesired object motion or for any other purpose related to robotic control and/or user experience.

Additionally, multiple tuning parameters can be associated with any single SIF. For example, the tuning parameters for one SIF may change with respect to time, detection of a condition, distance of the SIF to the respective object, distance of the SIF to the virtual boundary 71, or the like. In another example, the one SIF may be sizeable enough to simultaneously include multiple tuning parameters. For instance, one portion/surface/volume of the SIF may be configured to be more or less stiff than another portion/surface/volume of the same SIF.

Any characteristics of the SIFs described above can dynamically change intraoperatively during the procedure, or during pauses in operation of the robotic system. For example, the control system may determine a SIF change event in response to some control event or environmental condition. Such conditions may be expected or unexpected and can be detected by the control system using localization data, kinematic data, or any combination thereof. In response, the control system can dynamically change the location, geometric configuration, spacing, stiffness, of one or more SIFs. This dynamic changing feature can be managed based on input into the program and/or automatically managed, for example, based on factors such as the surgical plan, type or step of operation, surgeon preferences, and the like.

Any of the described features, characteristics, properties, and/or behaviors of the SIFs can be referred to as a parameter of the SIF. Any of the above implementations or parameters of the SIFs can be utilized individually, or in any combination thereof.

Several embodiments have been described in the foregoing description. However, the embodiments discussed herein are not intended to be exhaustive or limit the invention to any particular form. The terminology, which has been used, is intended to be in the nature of words of description rather than of limitation. Many modifications and variations are possible in light of the above teachings and the invention may be practiced otherwise than as specifically described.

The invention claimed is:

1. A surgical system comprising:
    a tool;
    a manipulator to support the tool; and
    a control system to control operation of the manipulator and movement of the tool based on a relationship between the tool and a virtual boundary associated with a target site, the control system including:
        a user input having a first input state and a second input state,
        wherein the control system is configured to enable autonomous, boundary-complying movement of the tool when the user input is in the first input state so that the tool maintains compliance with the virtual boundary,
        wherein the control system is configured to disable autonomous, boundary-complying movement of the tool when the user input is in the second input state; and
        a boundary handler to determine, in response to the user input transitioning from the second input state to the first input state, whether the tool is in violation of the virtual boundary.

2. The surgical system of claim 1, wherein the control system is configured to initiate a recovery mode in response to the tool being in violation of the virtual boundary when the user input transitions from the second input state to the first input state, and autonomous, boundary-complying movement of the tool remains disabled in the recovery mode when the user input is in the first input state.

3. The surgical system of claim 1, wherein the tool includes a tool drive and the control system is configured to disable operation of the tool drive in response to the tool being in violation of the virtual boundary when the user input transitions from the second input state to the first input state.

4. The surgical system of claim 2, wherein:
the control system is configured to guide a user into placing the tool into compliance with the virtual boundary in the recovery mode by generating user feedback that includes one or more of audible feedback, visual feedback, and haptic feedback; and
the control system is configured to cease generating the user feedback when the tool is placed into compliance with the virtual boundary.

5. The surgical system of claim 4, wherein the control system is configured to limit relative movement between the tool and the virtual boundary when the user input is in the first input state by generating boundary constraints with the boundary handler, wherein the control system comprises:
a constraint solver to calculate a constraint force adapted to maintain the tool in compliance with the virtual boundary based on the boundary constraints; and
a virtual simulator to simulate dynamics of the tool in a virtual simulation based on the constraint force, and to output a commanded pose,
the control system being configured to command the manipulator to move the tool based on the commanded pose.

6. The surgical system of claim 5, wherein the boundary handler is operable between a boundary-enabled state in which boundary constraints are being transmitted from the boundary handler to the constraint solver to thereby enable autonomous, boundary-complying movement of the tool when the virtual boundary moves relative to the tool in a manner that would otherwise cause the tool to violate the virtual boundary and a boundary-disabled state in which boundary constraints are no longer being transmitted from the boundary handler to the constraint solver to thereby disable autonomous, boundary-complying movement of the tool such that the virtual boundary is movable relative to the tool in a manner that causes the tool to violate the virtual boundary, the boundary handler being configured to:
operate in the boundary-disabled state in response to the user input transitioning from the first input state to the second input state;
operate in the boundary-enabled state in response to the user input transitioning from the second input state to the first input state with the tool in compliance with the virtual boundary; and
operate in the boundary-disabled state in response to the user input transitioning from the second input state to the first input state with the tool in violation of the virtual boundary.

7. The surgical system of claim 6, wherein the control system is configured to provide haptic feedback to the user to guide the user into placing the tool into compliance with the virtual boundary by: activating one or more guide constraints to guide the tool into compliance with the virtual boundary, or by dampening movement of the tool.

8. The surgical system of claim 7, wherein the control system is configured to switch the boundary handler from the boundary-disabled state to the boundary-enabled state when the tool is placed into compliance with the virtual boundary.

9. The surgical system of claim 1, wherein the user input is configured such that the first input state indicates that a user is actively engaging the tool and the second input state indicates that the user has released the tool.

10. The surgical system of claim 1, wherein the user input is located on the tool and the user input is configured such that the user input is actuated to place the user input in the first input state and the user input is released to place the user input in the second input state, wherein the tool has a grip and the user input includes a presence detector to detect a hand of a user on the grip.

11. The surgical system of claim 1, wherein the control system comprises a pendant and the user input is located on the pendant, the user input being configured such that the user input is actuated to place the user input in the first input state and the user input is released to place the user input in the second input state.

12. The surgical system of claim 1, wherein the user input is further defined as a tool input located on the tool and the first and second input states are further defined as a tool input first state and a tool input second state, wherein the control system comprises a pendant and a pendant input located on the pendant, the pendant input having a pendant input first state and a pendant input second state.

13. The surgical system of claim 12, wherein the manipulator is operable in a manual mode in which the manipulator moves the tool in response to user forces and torques applied to the tool by a user when the tool input is in the tool input first state and the manipulator is operable in a semi-autonomous mode in which the manipulator moves the tool along a tool path when the pendant input is in the pendant input first state.

14. The surgical system of claim 13, wherein:
the boundary handler is configured to determine whether the tool is in compliance with the virtual boundary or is in violation of the virtual boundary in response to the control system switching operation of the manipulator from one of the manual and semi-autonomous modes to the other of the manual and semi-autonomous modes;
the control system comprises a path handler configured to generate a lead-in path from a current position of the tool to the tool path when the manipulator switches from the manual mode to the semi-autonomous mode; and the boundary handler is configured to determine whether movement of the tool along the lead-in path would maintain compliance with the virtual boundary or would violate the virtual boundary;
the boundary handler is configured to determine whether movement of the tool along the lead-in path would maintain compliance with the virtual boundary or would violate the virtual boundary by modeling motion of a plurality of stereotactic interaction features associated with the tool to determine if the stereotactic interaction features would maintain compliance with the virtual boundary or would violate the virtual boundary;
the boundary handler is configured to model motion of the plurality of stereotactic interaction features in three or more degrees of freedom; and
the control system comprises a guide handler configured to generate user feedback to the user in response to the boundary handler determining that the tool would violate the virtual boundary if the tool moved from the current position, along the lead-in path, to the tool path.

15. The surgical system of claim 14, wherein the control system is configured to:
define a first parameter for a first one of the plurality of stereotactic interaction features; and
define a second parameter for a second of the plurality of stereotactic interaction features, wherein the first parameter is different from the second parameter.

16. The surgical system of claim 1, wherein the control system is configured to disable autonomous, boundary-complying movement of the tool in response to one or more of the following:
- the tool coming to a stop;
- a predetermined time period elapsing following a transition of the user input from the first input state to the second input state;
- a linear velocity of the tool falling below one or more thresholds; or
- an angular velocity of the tool falling below one or more thresholds.

17. The surgical system of claim 1, wherein the control system is configured to determine whether the tool remains in compliance with the virtual boundary based on a tolerance defined for the virtual boundary.

18. The surgical system of claim 2, wherein the control system is configured to generate a recovery tool path in the recovery mode to move the tool into compliance with the virtual boundary.

19. The surgical system of claim 2, wherein the control system is configured to move the virtual boundary in the recovery mode from a starting location so that the tool returns to being in compliance with the virtual boundary and thereafter, moving the virtual boundary back to the starting location while enabling autonomous, boundary-complying movement of the tool.

20. A method of controlling operation of a manipulator supporting a tool based on a relationship between the tool and a virtual boundary associated with a target site, the method comprising the steps of:
- initiating autonomous, boundary-complying movement of the tool when a user input is in a first input state and in response to the virtual boundary moving relative to the tool, such that the tool maintains compliance with the virtual boundary;
- disabling autonomous, boundary-complying movement of the tool when the user input is in a second input state; and
- determining, in response to the user input transitioning from the second input state to the first input state, whether the tool is in violation of the virtual boundary.

21. The method of claim 20, comprising initiating a recovery mode in response to the tool being in violation of the virtual boundary when the user input transitions from the second input state to the first input state.

22. The method of claim 21, comprising:
- disabling operation of a tool drive of the tool in response to the tool being in violation of the virtual boundary when the user input transitions from the second input state to the first input state; and
- guiding a user into placing the tool into compliance with the virtual boundary in the recovery mode by generating user feedback that includes one or more of audible feedback, visual feedback, and haptic feedback.

23. The method of claim 20, comprising transmitting boundary constraints from a boundary handler to a constraint solver in a boundary-enabled state and ceasing to transmit boundary constraints from the boundary handler to the constraint solver in a boundary-disabled state.

24. The method of claim 23, comprising:
- operating in the boundary-disabled state in response to the user input transitioning from the first input state to the second input state;
- operating in the boundary-enabled state in response to the user input transitioning from the second input state to the first input state with the tool in compliance with the virtual boundary; and
- operating in the boundary-disabled state in response to the user input transitioning from the second input state to the first input state with the tool in violation of the virtual boundary.

25. The method of claim 23, comprising activating one or more guide constraints to provide haptic feedback to a user to guide the user into placing the tool into compliance with the virtual boundary.

26. The method of claim 23, comprising causing dampened movement of the tool to provide haptic feedback to a user to guide the user into placing the tool into compliance with the virtual boundary.

27. The method of claim 23, comprising switching from the boundary-disabled state to the boundary-enabled state when the tool is placed into compliance with the virtual boundary.

28. The method of claim 20, comprising operating the manipulator in a manual mode in which the manipulator moves the tool in response to user forces and torques applied to the tool by a user or in a semi-autonomous mode in which the manipulator moves the tool along a tool path.

29. The method of claim 28, comprising:
- determining whether the tool is in compliance with the virtual boundary or is in violation of the virtual boundary in response to switching operation of the manipulator from one of the manual and semi-autonomous modes to the other of the manual and semi-autonomous modes;
- generating a lead-in path from a current position of the tool to the tool path when the manipulator switches from the manual mode to the semi-autonomous mode;
- determining whether movement of the tool along the lead-in path would maintain compliance with the virtual boundary or would violate the virtual boundary by modeling motion of a plurality of stereotactic interaction features associated with the tool to determine if the stereotactic interaction features would maintain compliance with the virtual boundary or would violate the virtual boundary;
- modeling motion of the plurality of stereotactic interaction features in three or more degrees of freedom; and
- generating user feedback to the user in response to determining that the tool would violate the virtual boundary if the tool moved from the current position, along the lead-in path, to the tool path.

30. The method of claim 20, comprising disabling autonomous, boundary-complying movement of the tool in response to one or more of the following:
- the tool coming to a stop;
- a predetermined time period elapsing following a transition of the user input from the first input state to the second input state;
- a linear velocity of the tool falling below one or more thresholds; or
- an angular velocity of the tool falling below one or more thresholds.

31. The method of claim 21, comprising generating a recovery tool path in the recovery mode to move the tool into compliance with the virtual boundary.

32. The method of claim 21, comprising moving the virtual boundary in the recovery mode from a starting location so that the tool returns to being in compliance with the virtual boundary and thereafter, moving the virtual boundary back to the starting location while enabling autonomous, boundary-complying movement of the tool.

* * * * *